US008143237B2

(12) United States Patent
Gokaraju et al.

(10) Patent No.: US 8,143,237 B2
(45) Date of Patent: Mar. 27, 2012

(54) ANTI-CANCER DRUGS, AND USES RELATING FOR MALIGNANT MELANOMA AND OTHER CANCERS

(75) Inventors: Ganga Raju Gokaraju, Vijayawada (IN); Sudhakar Kasina, Mercer Island, WA (US); Rama Raju Gokaraju, Vijayawada (IN); Venkata Kanaka Ranga Raju Gokaraju, Vijayawada (IN); Venkateswarlu Somepalli, Vijayawada (IN); Trimurtulu Golakoti, Vijayawada (IN); Kiran Bhupathiraju, Vijayawada (IN); Sengupta Krishanu, Vijayawada (IN); Venkata Krishna Raju Alluri, Vijayawada (IN)

(73) Assignee: Kasina Laila Innova Pharmaceuticals Private Limited, Vijayawada, IN (US)

( * ) Notice: Subject to any disclaimer, the term of this patent is extended or adjusted under 35 U.S.C. 154(b) by 52 days.

(21) Appl. No.: 12/767,647

(22) Filed: Apr. 26, 2010

(65) Prior Publication Data

US 2010/0272678 A1    Oct. 28, 2010

(30) Foreign Application Priority Data

Apr. 27, 2009    (IN) .............................. 959/CHE/2009

(51) Int. Cl.
*C07D 517/04*    (2006.01)
*A61K 31/53*    (2006.01)
*A61K 31/655*    (2006.01)
*A61P 31/00*    (2006.01)

(52) U.S. Cl. ......... 514/151; 514/243; 534/551; 544/184
(58) Field of Classification Search ........................ None
See application file for complete search history.

(56) References Cited

U.S. PATENT DOCUMENTS
2007/0197493 A1    8/2007    Chang et al.

FOREIGN PATENT DOCUMENTS
WO    2008016664 A    2/2008

OTHER PUBLICATIONS

Golub et al., "Molecular Classification of Cancer: Class Discovery and Class Prediction by Gene Expression Monitoring", Science, 286, 531-537, 1999.*
Patel, V.J. et al., Schedule-dependent Activity of Temozolomide plus CPT-11 against a Human Central Nervous System Tumor-derived Xenograft1, Clinical Cancer Research, 2000, vol. 6, 4154-4157.
De Angulo et al., Early Lymphocyte Recovery as a Prognostic Indicator for High-risk Ewing Sarcoma, J Pediatr Hematol Oncol. vol. 29, No. 1, Jan. 2007.
Howe et al., Annual Report to the Nation on the Status of Cancer (1973 Through 1998), Featuring Cancers With Recent Increasing Trends, Journal of the National Cancer Institute, vol. 93, No. 11, Jun. 6, 2001.
Chapman et al., Phase III Multicenter Randomized Trial of the Dartmouth Regimen Versus Dacarbazine in Patients With Metastatic Melanoma, Journal of Clinical Oncology, vol. 17, No. 9 Sep. 1999: pp. 2745-2751.
Middleton et al., Randomized Phase III Study of Temozolomide Versus Dacarbazine in the Treatment of Patients With Advanced Metastatic Malignant Melanoma, Journal of Clinical Oncology, vol. 18, No. 1 Jan. 2000: pp. 158-166.
Middleton et al., A randomized phase III study comparing dacarbazine, BCNU, cisplatin and tamoxifen with dacarbazine and interferon in advanced melanoma, British Journal of Cancer (2000) 82(6), 1158-1162.
Lev et al., Dacarbazine Causes Transcriptional Up-Regulation of Interleukin 8 and Vascular Endothelial Growth Factor in Melanoma Cells: A Possible Escape Mechanism from Chemotherapy, Molecular Cancer Therapeutics, vol. 2, 753-763, Aug. 2003.
Lev et al., Exposure of Melanoma Cells to Dacarbazine Results in Enhanced Tumor Growth and Metastasis In Vivo, Journal of Clinical Oncology, vol. 22, pp. 2092-2100, Jun. 2004.
Sengupta et al., Thombospondin-1 Disrupts Estrogen-Induced Endothelial Cell Proliferation and Migration and Its Expression Is Suppressed by Estradiol, Molecular Cancer Research, vol. 2, 150-158, Mar. 2004.
Diana et al., Fibrin II Induces Endothelial Cell Capillary Tube Formation, The Journal of Cell Biology, vol. 130, No. 1, Jul. 1995 207-215.

(Continued)

*Primary Examiner* — Fiona T Powers
(74) *Attorney, Agent, or Firm* — Kramer & Amado, P.C.

(57) ABSTRACT

Selenopheno triazene analogs, their compositions, tautomeric forms, stereoisomers, polymorphs, hydrates, solvates, and pharmaceutically acceptable salts and mixtures thereof are useful for the treatment of metastatic malignant melanoma and other cancers. The selenopheno triazene analogs have the general formulae (I) or (II):

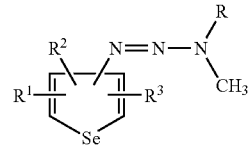

General Formula I

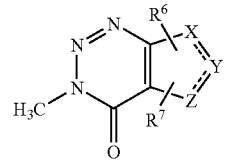

General Formula II wherein the substituents $R^1$, $R^2$, $R^3$, $R^6$, and $R^7$ are as described in the specification. Other cancers include which may be treated with these compounds include, but are not limited to, malignant melanoma, leukemia, lymphomas (Hodgkins and non-Hodgkins), sarcomas (Ewing's sarcoma), brain tumors, central nervous system (CNS) metastases, gliomas, carcinomas such as breast cancer, prostate cancer, lung cancer (small cell and non-small cell), colon cancer, pancreatic cancer, Head and Neck cancers and oropharyngeal squamous cell carcinoma.

31 Claims, 8 Drawing Sheets

OTHER PUBLICATIONS

Friedman et al., O6-Benzylguanine-mediated Enhancement of Chemotherapy, Molecular Cancer Therapeutics, vol. 1, 943-948, Sep. 2002.

Lowe et al., Antitumor Imidazotetrazines: Crystal Structure of 8-Carbomyl-3-methylimidazo [5,1]-1,2,3,5,-tetrazin-4(3H)-one (Temozolomide) and Structural Comparisons with the Related Drugs Mitozolomide and DTIC, Journal of Medicinal Chemistry, 1992, vol. 35, pp. 3377-3382.

International Search Report for issued for PCT/IN2010/000262 dated Sep. 27, 2010.

\* cited by examiner

ANTI-CANCER DRUGS, AND USES RELATING FOR MALIGNANT MELANOMA AND OTHER CANCERS

FIELD OF THE INVENTION

The present invention relates to Selenophene compounds and Selenophene triazene compounds, their geometrical isomeric forms, stereoisomers, configurational isomers, polymorphs, hydrates, solvates and pharmaceutically acceptable salts thereof.

The present invention further relates to a process for the preparation of the above said Selenophene compounds and Selenophene triazene compounds and their pharmaceutically acceptable compositions.

A goal of the present invention is to provide Selenopheno triazene compounds as active ingredient(s) either alone or in combination with other pharmaceutically acceptable drugs for the prevention and treatment of cancer and other vascular diseases.

The compounds of the present invention are also potent angiogenesis inhibitors and can be effectively used for pharmaceutical compositions that prevent angiogenesis related diseases including cancer and other vascular diseases.

The novel compounds and compositions are useful for the prevention, control and treatment of metastatic malignant melanoma and for carcinomas of the solid tumors, and all other cancers including but not limited to lymphomas, sarcomas and gliomas either alone or in combination with other pharmaceutically acceptable drugs or excipients.

BACKGROUND OF THE INVENTION

Melanoma, a malignant neoplasm, is derived from cells that are capable of forming melanin, arising most commonly in the skin of any part of the body and in the eye, or rarely, in the mucus membrane of the genitalia, anus, oral cavity, or other sites. It occurs mostly in adults and may originate de novo or from a pigmented nevus or lentigo maligna. In the early phases, the cutaneous form is characterized by a proliferation of cells at the dermal epidermal junction which soon invades adjacent tissues. The cells vary in amount and pigmentation of cytoplasm; the nuclei are relatively large and frequently bizarre in shape, with prominent acidophilic nucleoli; the mitotic figures tend to be numerous. Melanomas frequently metastasize widely; regional lymph nodes, skin, liver, lungs, and brain are likely to be involved.

In January 1985, the Environmental Protection Agency (EPA) predicted that depletion of the Earth's Ozone layer (approximately expected to diminish by 10% because of human activities), which guards against ultraviolet (UV) radiation from space, would cause an increase in the number of skin cancer cases worldwide (an estimated annual increase of two million cases by the year 2050), including melanomas. Also, exposure to higher levels of ultraviolet radiation may also promote cataracts and immune system dysfunction.

Public health efforts have focused on encouraging people to use sunscreen, avoid outdoor activities during peak exposure times, perform frequent self-checks of the skin, and visit dermatologists when irregularities are noted.

UV radiation represents a definitive risk factor for skin cancer, especially when exposure occurs in combination with certain underlying genetic traits, such as red hair and fair skin. Pigmentation of the skin results from the synthesis of melanin in the pigment-producing cells, the melanocytes, followed by distribution and transport of pigment granules to neighboring keratinocytes. It is commonly believed that melanin is crucial for absorption of free radicals that have been generated within the cytoplasm by UV and acts as a direct shield from UV and visible light radiation.

UV-induced pigmentation (sun tanning) requires induction of α-melanocyte-stimulating hormone (α-MSH) secretion by keratinocytes. α-MSH and other bioactive peptides are cleavage products of Pro-Opiomelanocortin (POMC). The p53 tumor suppressor gene is one of the most frequent targets for genetic alterations in cancer. The p53 is a transcriptional regulator of the POMC gene, which translates to proteins that cause the melanocytes to produce melanin, which wards off skin cancer by absorbing UV radiation. Direct mutational inactivation of p53 is observed in close to half of all human tumors. Malignant melanoma is a skin cancer which is, by far, one of the hardest cancers to treat today.

Dacarbazine (DTIC) is the only agent used to treat metastatic malignant melanoma. In addition, Dacarbazine is also indicated for Hodgkin's lymphoma as a secondary line therapy when used in combination with other effective drugs. Chemically, DTIC is 5-(3,3-dimethyl-1-trizeno)-imidazole-4-carboxamide with the following structural formula:

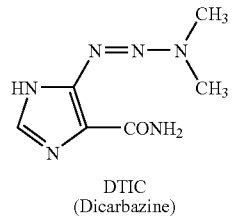

DTIC
(Dicarbazine)

Dacarbazine, however, requires bioactivation in vivo by the liver. One of the methyl groups of the dimethyltriazeno functionality is activated by liver microsomal enzymes and, in particular, by the Cytochrome P450, to oxidation, resulting in a hydroxymethyl group. Thus, the oxidative mono-demethylation of the dimethyltriazeno functionality affords monomethyltriazene. The monomethyltriazene metabolite, 3-methyl-(triazen-1-yl)-imidazole-4-carboxamide (MTIC) is further hydrolyzed to 5-amino-imidazole-4-carboxamide (AIC), which is known to be an intermediate in purine and nucleic acid biosynthesis and to methylhydrazine, which is believed to be the active alkylating species. The Cytochrome P450 enzymes play only a minor role in the metabolism of MTIC.

Temozolomide is also a similar imidazotetrazine alkylator that methylates DNA at nucleophilic site. Temozolomide as a bicyclic compound is orally bioavailable, more lipophilic, and spontaneously converted to MTIC, and also seems to generate less nausea. The $O^6$-methylguanine adducts causes a mismatch during DNA replication and the addition of a thymidine, instead of cytosine, to the newly formed DNA strand. Because of the excellent CNS biodistribution, temozolomide has been useful as a radiosensitizer in both primary brain tumors and CNS metastases. Temozolomide improves quality of life when used with radiation in patients with brain metastases. Unlike Dacarbazine, Temozolomide has activity against sarcoma. Thus the analogous bicyclic Temozolomide derivative having Selenium may be useful in sarcoma radiosensitization for primary control as well as for the treatment of metastases. Temozolomide is a radiosensitizer that is well tolerated and has modest side effects. The combination of Temozolomide and Irinotecan is more than additive against some cancers. The author(s) Patel, V. J. et al., *Clin. Cancer Res.*, 2000, 6, 4154-4157 report that their experience confirms a high response rate in relapsed Ewing's sarcoma and DSRCT that is possibly even higher than that reported in the literature. The Temozolomide plus Irinotecan combination is less immune suppressive than standard cyclophosphamide-containing regimens. This might be especially important in Ewing's sarcoma since the author(s) De Angulo, G. et al., *J. Pediatr. Hematol. Oncol.*, 2007, 29, 48-52 have shown that lymphocyte recovery (i.e., absolute lymphocyte count >500 on day 15 after the first cycle of chemotherapy) is associated with significantly higher survival in Ewing's sarcoma. Temozolomide or Dacarbazine has also been combined with other drugs including Gemcitabine and Doxorubicin liposomes. The disappearance of DTIC from the plasma is biphasic with an initial half life of 19 minutes and a terminal half life of five hours. In a patient with renal and hepatic dysfunctions, the half lives were lengthened to 55 minutes and 7.2 hours, respectively. The average cumulative excretion of unchanged DTIC in the urine is 40% of the injected dose in six hours. DTIC is subject to renal tubular secretion rather than Glomerular Filtration. At therapeutic concentrations, DTIC is not appreciably bound to human plasma protein.

In humans, DTIC is extensively degraded. Besides unchanged DTIC, AIC is a major metabolite of DTIC excreted in the urine. Although the exact mechanism of action of DTIC is not known, three hypotheses have been offered:

1. Inhibition of DNA synthesis by acting as a purine analog
2. Acting as an alkylating agent
3. Interaction with sulfhydryl (SH) groups Thus, the biochemical mechanism of action of the resulting MTIC reactive species whose cytotoxicity involved in generation of methyl carbonium ion in vivo is thought to be primarily due to alkylation of DNA. Alkylation (methylation) occurs mainly at the $O^6$ and $N^7$ positions of guanine.

Alternatively, DTIC, prior to its metabolism to the monomethyltriazene, is oxidized initially to monohydroxymethyl and finally to an aldehyde. The monomethyltriazene, in its aldehyde form prior to oxidative monodemethylation, is cyclized to the cyclic compound (as shown in Scheme 1) which interferes with the double helix DNA structure and blocks replication of the cancer cells.

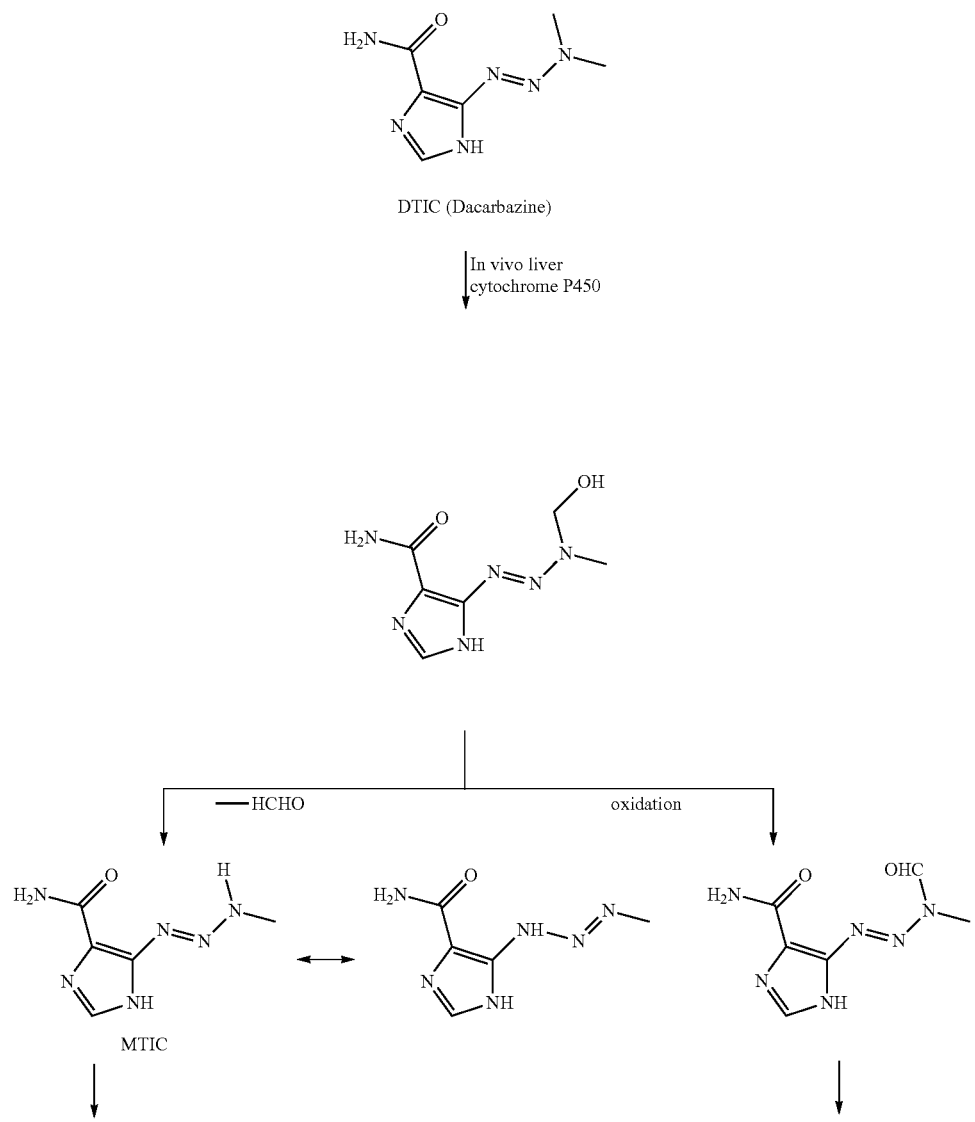

Scheme 1: Biochemical mechanism of action of Dacarbazine

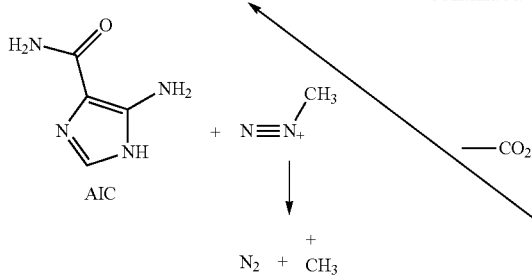

AIC

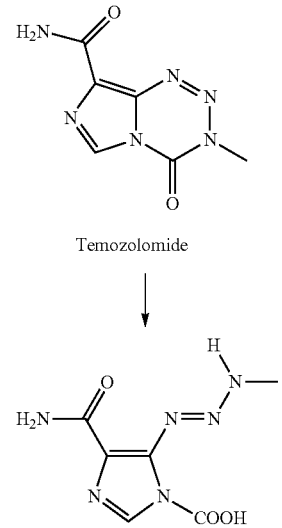

Temozolomide

The imidazole ring system of the Dacarbazine is hydrophilic in nature. Therefore, there is a need in the art for possibly effective binding to the melanin such that the cytotoxic functionality of the molecule is one hundred percent effective. Thus, the present inventors have aimed to provide novel compounds with increased lipophilicity thereby providing more target specificity. Thus, Selenophene, which has a five-membered aromatic heterocyclic ring system, with Selenium in the ring is lipophilic in nature and may have effective binding by increased avidity to the melanin; as a result, one would be able to get the same therapeutic effectiveness at a significantly lower dose, hence minimizing the toxicity. This would in turn afford high specificity with a larger window of the Therapeutic Index (TI). In general, for the treatment of cancer patients, a larger therapeutic index is preferred. This is because; one would like to start the therapeutic regimen with a very high Maximum Tolerated Dose (MTD) such that the cancer cells would be hit hard in the first chemotherapy itself. Otherwise, the surviving cancer cells would repair the DNA damage and subsequently metastasize to the other organs. In addition, the cancer cells that survived from the first treatment would become resistant to the second chemotherapy again, if needed. And besides, due to weakness of the immune system from the first chemotherapy, a suboptimal dose would be given in the second treatment that would contribute to toxicity.

As shown in Scheme-1, unlike DTIC, better interaction of the selenophene ring system with the SH groups on the surface of the tumor antigen results in increased efficacy. This is because of selenium (Se) being larger atom and hence a five membered heterocyclic aromatic selenophene ring system resemble a phenyl ring in space, would contribute it's loan pair of electrons to the rest of the ring for better interaction with sulfhydryls at the tumor site. In addition, due to its electronic configuration, the heterocyclic aromatic selenophene ring system may be superior over DTIC by way of inhibition of DNA synthesis by acting as a purine analog as well as acting as an alkylating agent. Also, unlike DTIC, while Amino Imidazole Carboxamide (AIC) is inactive by itself, the corresponding Amino Selenophene Carboxamide (ASC) would very well be active in vivo via de-localization of electrons from the ring selenium for increased efficacy. Both AIC and ASC are incorporate into DNA. Thus, the novel triazeno selenophene analogs have several additional advantages inherently built in within the structure over Dacarbazine for increased activity.

Therefore, in order for the dose regimen to be effective, possibly high melanin binding moieties such as selenophene system could offer a therapeutic treatment having all the three biochemical mechanisms of action superior to DTIC (Dacarbazine) with a possible positive outcome leading to complete responses. Thus, the present invention aims to fulfill this unmet medical need of selectively binding to the targeted melanoma cells and sparing the normal cells thereby increasing the target to non-target cell ratio and further providing other related advantages as described herein.

Angiogenesis, or neovascularization, is the process of generating new blood vessels derived as extensions from the existing vasculature. Angiogenesis plays an important role in the growth and spread of cancer. New blood vessels "feed" the cancer cells with oxygen and nutrients, allowing these cells to grow, invade nearby tissue, spread to other parts of the body, and form new colonies of cancer cells. Therefore, anti-angiogenesis or inhibition of angiogenesis has been considered as a potential therapeutic strategy for controlling tumor growth and metastatic spread of cancer cells.

The inventors of the present invention during their ongoing effort to invent novel compound(s), have surprisingly found that Selenopheno triazene compounds of general formulae (I) and (II) were potent antimelanoma agents, angiogenesis inhibitors and are effective for the prevention, control and treatment of melanoma, cancers and other vascular diseases.

SUMMARY OF THE INVENTION

The present invention provides novel Selenophene and selenopheno triazene compounds of general formulae (I) and (II), respectively.

In a preferred aspect, the present invention also provides selenopheno triazene compounds of the general formula (I):

General Formula I

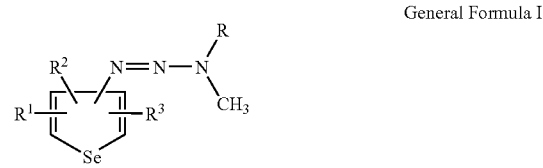

Wherein,

R is selected from H, $CH_3$ and $CH_2OH$.

$R^1$, $R^2$ and $R^3$ are independently selected from H, N=N—N$(CH_3)_2$, N=N—$NHCH_3$, N=NN$(CH_3)CH_2OH$, $CONH_2$, $CONHR^4$, $CONR^4R^5$, $CONHNH_2$, $CONHNHR^4$, $CONHNR^4R^5$, $COOCH_3$, $COOCH_2CH_3$, COOH, COSH, CN, C≡CH, $SO_2NH_2$, $SO_2NHR^4$, $SO_2NR^4R^5$, $NO_2$, $CF_3$, Cl, Br, F, $CCl_3$, $CH_3$, OH, $OCH_3$, SH, $SCH_3$, $NH_2$, $NHCH_3$, $N(CH_3)_2$, alkyl, alkenyl etc. electron withdrawing and electron donating functional groups, wherein $R^4$ and $R^5$ are independently selected from H, $CH_3$, $C_1$-$C_{10}$ alkyl, alkenyl, alkylol, alkoxy, alkylamine, etc.; alternatively, any two of $R^1$, $R^2$ and $R^3$ can be joined together to form alicyclic, aromatic, heterocyclic systems. In certain embodiments, any two of $R^1$, $R^2$ and $R^3$ can be joined together to form cyclohexyl, cyclopentyl, phenyl or pyridyl rings.

In another aspect, the present invention provides selenopheno triazene compounds of the general formula (II).

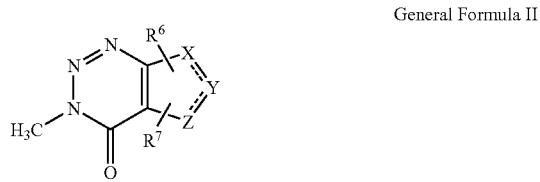

General Formula II

Wherein,

X, Y and Z are independently selected from C and Se such that the resulting five membered aromatic heterocyclic moieties involving the bicyclic system are un-substituted and substituted Selenophenes, such that the double bond is either in between X and Y or in between Y and Z;

$R^6$ and $R^7$ are independently selected from H, N=N—N$(CH_3)_2$, N=N—$NHCH_3$, N=N—$N(CH_3)CH_2OH$, $CONH_2$, $CONHR^8$, $CONR^8R^9$, $CONHNH_2$, $CONHNHR^8$, $CONHNR^8R^9$, $COOCH_3$, $COOCH_2CH_3$, COOH, COSH, CN, C≡CH, $SO_2NH_2$, $SO_2NHR^8$, $SO_2NR^8R^9$, $NO_2$, $CF_3$, Cl, Br, F, $CCl_3$, $CH_3$, OH, $OCH_3$, SH, $SCH_3$, $NH_2$, $NHCH_3$, $N(CH_3)_2$, alkyl, alkenyl, electron withdrawing functional groups, electron donating functional groups, etc.; and $R^8$ and $R^9$ are independently selected from H, $CH_3$, $C_1$-$C_{10}$ alkyl, alkenyl, alkylol, alkoxy, alkylamine, etc. Alternatively $R^6$ and, $R^7$ can be joined together to form alicyclic, aromatic, heterocyclic systems comprising cyclohexyl, cyclopentyl, phenyl and pyridyl.

In another aspect, the present invention provides pharmaceutically acceptable salts of the compounds of the general formulae (I) and (II), for example organic or inorganic salts.

In another aspect, the invention provides the optical enantiomers or diastereomers of the optically active compounds of general formulae (I) and (II).

In another aspect, the invention provides pharmaceutical compositions comprising:
a) at least one selenopheno triazene compound selected from the above general formula (I) and derivatives thereof;
b) at least one selenopheno triazene compound selected from the above general formula (II) and derivatives thereof; or
c) a mixture of at least one selenopheno triazene compound selected from the above general formula (I) and at least one selenopheno triazene compound selected from the above general formula (II).

The pharmaceutical compositions including a compound selected from the above general formula (I) and/or a compound selected from the above general formula (II) optionally further include at least one pharmaceutically acceptable excipient, carrier, or diluent. The pharmaceutical compositions may optionally include, in addition to a compound selected from the above general formula (I) and/or a compound selected from the above general formula (II), one or more pharmaceutical drugs.

In another aspect, the present invention provides a method of binding selenopheno triazene compound(s) to melanin or killing a cancer cell for a therapeutic purpose. The method includes the step of administering to a subject in need thereof a therapeutically effective amount of the said compound(s) of general formula (I) or (II) or their pharmaceutical composition(s).

In another aspect, the invented compound(s) are useful in the management of metastatic malignant melanoma and for carcinomas of solid tumors and all other cancers.

In another aspect, the invention further provides a method of inhibiting angiogenesis and for ameliorating the angiogenesis modulators which include but not limited to VEGF, PDGF, TGF-beta and FGF in warm blooded animals in need thereof comprising administering a therapeutically effective amount of selenophene and/or selenopheno triazene compounds of general formulae (I) and (II), respectively, or their pharmaceutical composition(s).

In another aspect, the present invention provides a method for remodeling of the vasculatures by modifying the proliferation, migration, invasion of endothelial cells and vascular smooth muscle cells in warm blooded animals in need thereof.

The present invention further provides a method for inhibiting metastatic tumor growth and its spread in warm blooded animals in need thereof.

DETAILED DESCRIPTION OF THE INVENTION

Figure 1:
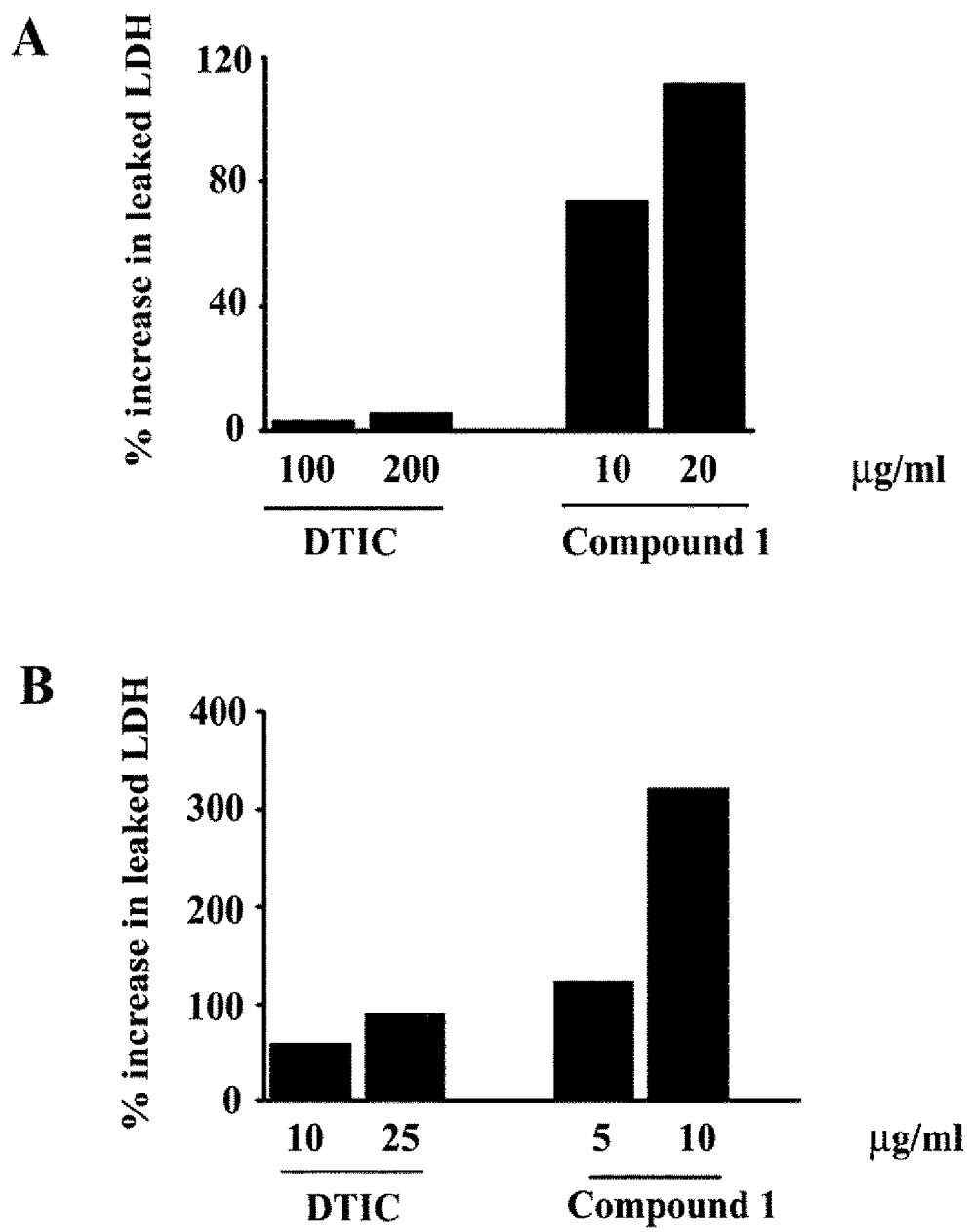
FIG. 1: Bar diagrams show percent increase in leaked Lactate dehydrogenase (LDH) from B16 F0 mouse melanoma cells (A), and in A375 human melanoma cells (B), treated with various concentrations of DTIC and Compound 1 as indicated in the diagrams. Each bar indicates the percent increase in leaked LDH with respect to the vehicle control cultures (0.5% DMSO), calculated form a mean of quadruplicate wells.

For the purpose of this invention, the following phrases or words are used to refer compounds of general formula (I) and (II):

The expression "Selenopheno triazene compounds", "Selenopheno triazene analog(s)", "triazene analog(s)", "triazene selenophene analog(s)", "selenophene analog(s)", "selenopheno analog(s)", "inventive analog(s)", "targeted analog(s) or "derivative(s) thereof" are used in the following text interchangeably.

The expression "analog(s)" and "derivative(s)" are used in the following text interchangeably.

The phrase "composition of the present invention" means and includes compounds of formula (I) or (II) along with at least one pharmaceutical carrier/excipient.

The expression "pharmaceutically acceptable" is meant the excipient(s), carrier(s), diluent(s), and/or salt(s) compatible with the other ingredients of the formulation, and not deleterious to the recipient thereof.

The invention will now be described in detail in connection with certain preferred and optional embodiments, so that various aspects thereof may be more fully understood and appreciated.

The incidence and mortality of melanoma continues to rise faster than that of any other cancer in all over the world including the United States (Howe, H. L. et al., J. Natl. Cancer Inst. (Bethesda), 93: 824-842, 2001). Overall, melanoma accounts for 1-3% of all malignant tumors and is increasing in incidence by 6-7% every year. In patients with advanced disease, 5-year life expectancy is less than 10%, with a median survival of 6-8.5 months. Melanoma metastases affect skin, lymph nodes, lung, liver, brain, bone, and sometimes other organs such as the pancreas. Different therapeutic approaches for metastatic melanoma have been evaluated, including chemotherapy and biological therapies, both as single treatments and in combination. However, Dacarbazine (DTIC) is being widely used as the primary choice of chemotherapy for treating malignant melanoma and is approved by the US Food and Drug Administration for this purpose (Chapman, P. B. et al., J. Clin. Oncol., 17: 2745-2751, 1999). However, response rates for single-agent DTIC are disappointing, ranging from only 10 to 25%, with complete responses seen in less than 5% of patients (Middleton, M. R. et al., J. Clin. Oncol., 18: 158-166, 2000; Middleton, M. R. et al., Br. J. Cancer, 82: 1158-1162, 2000). Previous investigations demonstrated that Dacarbazine can result in overexpression of angiogenic factors such as interleukin-8 (IL-8) and vascular endothelial growth factor (VEGF) (Lev D C et al., Mol Cancer Ther; 2:753-763, 2003; Lev D C et al., J. Clin. Oncol. 22: 2092-2100, 2004). Thus, the proangiogenic properties of Dacarbazine might provide the basis of lower chemotherapeutic efficacy of Dacarbazine against melanoma.

Therefore there is an unmet medical need to develop new therapies which address these problems.

The present invention utilizes selenophene as a back bone in place of imidazole in DTIC to significantly increase its activity for possible cure in the early diagnosis and to significantly increase efficacy in the treatment of late stage malignancy.

Figure 2:
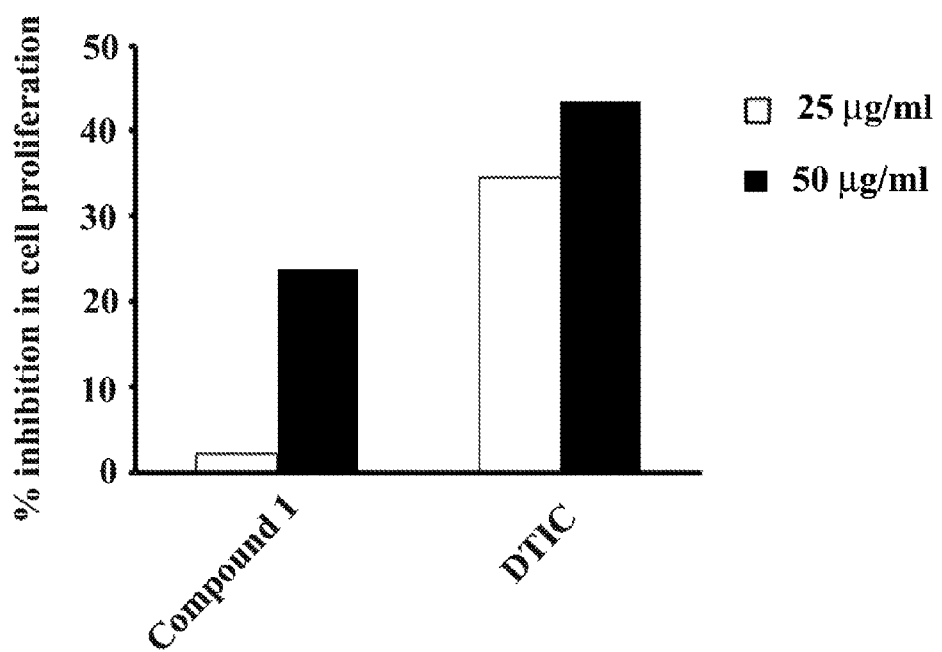
FIG. 2: Bar diagram represents percentage of growth inhibition of Hs.531.sk normal human skin cells by compound 1 and DTIC at 25 µg/ml and 50 µg/ml.
Figure 7:
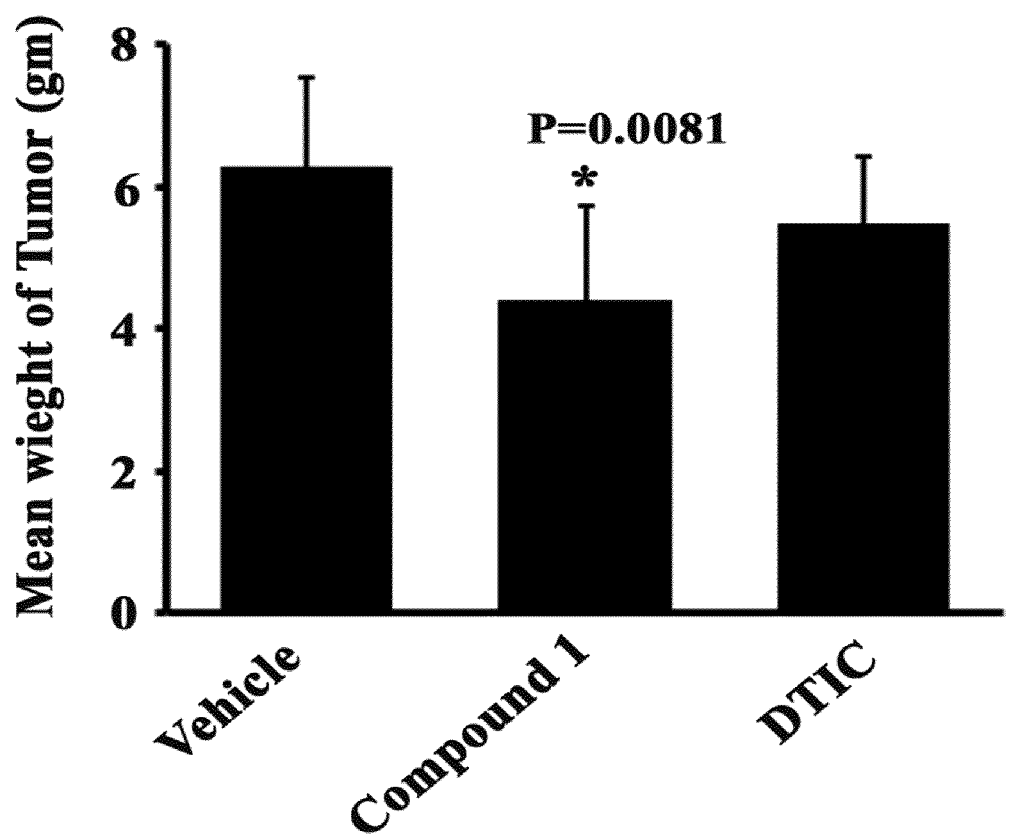
FIG. 7: Bar diagram shows comparative efficacies of Compound 1 and DTIC against B16F0 tumor growth in C57B6J mice. Each bar shows average tumor weight in gram (n=8) ±SD. Bar A indicates 10% DMSO treated vehicle control group; Bar B indicates 25 mg/kg of Compound 1 treated group; and Bar C indicates 75 mg/kg of DTIC treated group. *indicates statistical significance (p<0.05) vs. control (Student t-test).
Figure 8:
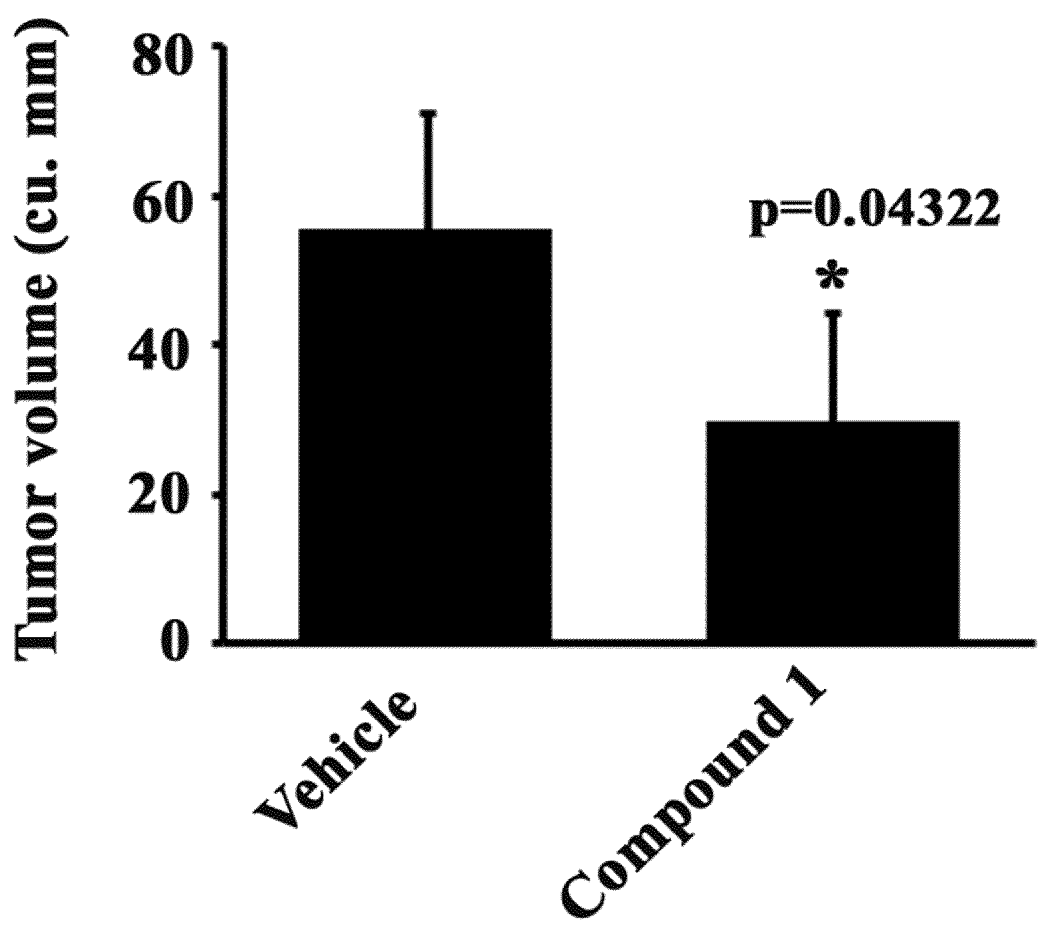
FIG. 8: Bar diagram shows anti-melanoma efficacy of Compound 1 in A375 human melanoma xenograft model of nu/nu BALB/c nude mice. Each bar shows average tumor volume in cubic millimeter (n=5)±SD. Bars represent average tumor volumes in 10% DMSO treated vehicle control group and 25 mg/kg of Compound 1 treated group, respectively. *indicates statistical significance (p<0.05) vs. control (Student t-test).

As a part of developing novel anti-tumor compounds, several selenophene analogs of general formulae (I) and (II) have been prepared and tested for their efficacy against several tumor cell lines. It was found very surprisingly that the triazene selenophene analog (Compound 1) of the general formula (I) showed nine times better potency in vitro compared to DTIC in the inhibition of A375 human melanoma cell line. The selenophene analog (Compound 1) showed an $IC_{50}$ value of 9.81 µg/ml compared to 70.1 µg/ml exhibited by DTIC. Its efficacy was further confirmed by in vivo experiments (FIGS. 7 and 8). The selenophene analog (Compound 1) showed 31.2% inhibition in the tumor growth compared to 17% inhibition showed by DTIC in mouse melanoma xenograft model of C57B6J mice (FIG. 7). In addition, in comparison with DTIC, the compound 1 showed significantly lesser cytotoxic effect in normal human skin epithelial cells (FIG. 2). This observation suggests that Compound 1 is able to inhibit efficiently the melanoma tumor cell growth without or minimally affecting the normal human cells. Hence, the novel analog (Compound 1) is significantly better than the marketed drug DTIC, in terms of efficacy and safety.

Figure 6:
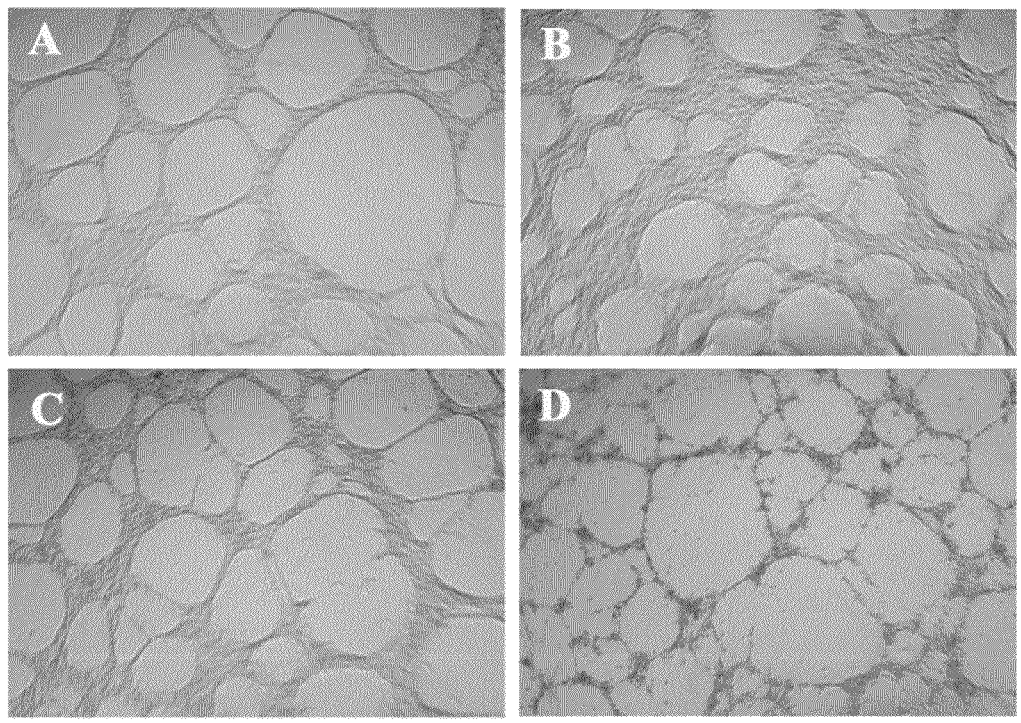
FIG. 6: Pictures show inhibition of capillary-like tube formation by Compound 1. Human umbilical vein endothelial cells (HUVECs) were laid on Cultrex coated plates in presence of either DTIC (100 µg/ml) or Compound 1 (5 and 10 µg/ml) (C, D) and allowed to form endothelial capillary tubes for 16 h at 37° C. Picture panels A-D represent, capillary-like tube formation in 0.1% DMSO treated vehicle control wells, DTIC treated culture and 5 and 10 µg/ml of Compound 1 treated cultures, respectively. The bars (A to D) in the bar graph represent the average number of branching points under different culture conditions, respectively as indicated in the picture panels.
Figure 6:
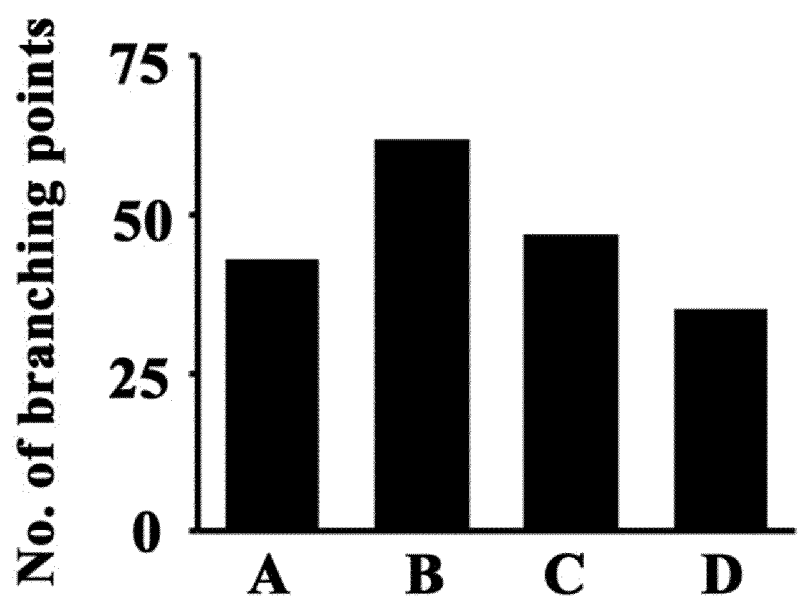

Compound 1 exhibited anti-angiogenic properties in endothelial capillary formation assay, whereas, DTIC could not inhibit the endothelial capillary formation in vitro (FIG. 6). In addition, Compound 1 inhibited endothelial cell migration, which suggests that this novel analog also might help in inhibiting tissue remodeling during the angiogenesis process required for tumor growth. Moreover, Compound 1 also significantly inhibited the invasion of malignant melanoma tumor cells (FIG. 4), whereas, DTIC failed to inhibit the tumor cell invasion. Together, these findings further suggest the superiority of Compound 1 over the marketed Drug DTIC in the treatment of malignant melanoma.

Other analogs (Compounds 2-16) also showed significantly higher efficacy compared to DTIC in B16F0 mouse melanoma cell line as summarized in Table 1.

Even though selected compounds have been used to demonstrate the present invention, the invention encompasses all compounds of the general formulae (I) and (II) and their derivatives.

In one preferred embodiment, invention provides selenopheno triazene compounds represented by the following general formula (I) and (II):

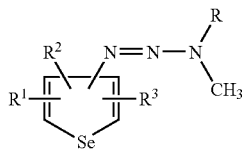

General Formula I

Wherein,
R is selected from H, $CH_3$ and $CH_2OH$;
$R^1$, $R^2$ and $R^3$ are independently selected from H, N=N—N$(CH_3)_2$, N=N—NHCH$_3$, N=N—N(CH$_3$)CH$_2$OH, CONH$_2$, CONHR$^4$, CONHR$^4$R$^5$, CONHNH$_2$, CONHNHR$^4$, CONHNR$^4$R$^5$, COOCH$_3$, COOCH$_2$CH$_3$, COOH, COSH, CN, C≡CH, SO$_2$NH$_2$, SO$_2$NHR$^4$, SO$_2$NR$^4$R$^5$, NO$_2$, CF$_3$, Cl, Br, F, CCl$_3$, CH$_3$, OH, OCH$_3$, SH, SCH$_3$, NH$_2$, NHCH$_3$, N(CH$_3$)$_2$, alkyl, alkenyl groups etc. electron withdrawing and electron donating functional groups, wherein $R^4$ and $R^5$ are independently selected from H, CH$_3$, $C_1$-$C_{10}$ alkyl, alkenyl, alkylol, alkoxy, alkylamine etc.

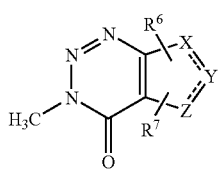

General Formula II wherein,
the notation ≡≡≡ represents a single bond or a double bond;
X, Y and Z are independently selected from C and Se such that the resulting bicyclic systems involving five membered aromatic heterocyclic moieties of un-substituted and substituted Selenophenes; such that the double bond is either in between X and Y or in between Y and Z.

$R^6$ and $R^7$ are either:
a) independently selected from H, N=N—N(CH$_3$)$_2$, N=N—NHCH$_3$, N=N—N(CH$_3$)CH$_2$OH, CONH$_2$, CONHR$^8$, CONR$^8$R$^9$, CONHNH$_2$, CONHNHR$^8$, CONHNR$^8$R$^9$, COOCH$_3$, COOCH$_2$CH$_3$, COOH, COSH, CN, C≡CH, SO$_2$NH$_2$, SO$_2$NHR$^8$, SO$_2$NR$^8$R$^9$, NO$_2$, CF$_3$, Cl, Br, F, CCl$_3$, CH$_3$, OH, OCH$_3$, SH, SCH$_3$, NH$_2$, NHCH$_3$, N(CH$_3$)$_2$, alkyl, alkenyl, electron withdrawing functional groups, and electron donating functional groups; or
b) joined together to form alicyclic, aromatic, ring heterocyclic systems; and
$R^8$ and $R^9$ are independently selected from H, CH$_3$, $C_1$-$C_{10}$ alkyl, alkenyl, alkylol, alkoxy, alkylamine.

Alkyl groups in general formulae (I) and (II) encompass, but are not limited to, methyl, ethyl, propyl, butyl, isopropyl, isobutyl, tertiary butyl, pentyl, hexyl, heptyl, octyl and other $C_1$ to $C_{30}$ alkyl groups; alkenyl groups in general refer to ethene, propene, butene, pentene and higher alkenyl groups, including $C_6$ to $C_{30}$ alkenyl groups with one or more double bonds; alkylol groups in general refer to hydroxymethyl, hydroxyethyl, hydroxypropyl and other hydroxyalkyl groups; alkoxy groups in general refer to methoxy, ethoxy, propoxy, butoxy, pentoxy and other higher alkoxy groups, include $C_6$ to $C_{30}$ carbon atoms; alkylamine groups refer to aminomethyl, aminoethyl, aminopropyl and other higher alkylamines having $C_4$ to $C_{30}$ carbon atoms.

Alternatively, any two of $R^1$, $R^2$ and $R^3$ in general formula (I) can be joined together to form alicyclic, aromatic, heterocyclic systems including but not limited to cyclopentyl, cyclohexyl, phenyl and pyridyl.

Alternatively, $R^6$ and $R^7$ in general formula (II) can be joined together to form alicyclic, aromatic, or heterocyclic systems including but not limited to cyclopentyl, cyclohexyl, phenyl and pyridyl.

The present invention relates to novel selenopheno triazene compounds of the general formulae (I) and (II). The compounds of the general formulae (I) and (II) are disclosed together because of their metabolic relationship. For example, a compound of general formula (I) upon in vivo activation by liver microsomal enzymes (cytochrome P450) followed by oxidative demethylation, affords its monomethyltriazene derivative. Likewise, analogous compound of general formula (II) upon in vivo hydrolysis affords similar monomethyltriazene derivative. Therefore, due to their metabolic relationship in vivo, the compounds of general formulae (I) and (II) constitute a single invention. However, the compounds of general formulae (I) and (II) are disclosed separately for convenience.

In another embodiment, the present invention relates to the geometrical isomeric forms, stereoisomers, configurational isomers, polymorphs, hydrates, solvates and pharmaceutically acceptable salts thereof of general formulae (I) and (II).

In another preferred embodiment the invention provides the synthesis of following selenopheno triazene compounds of general formulae (I) or (II), the preparation of which is described in examples 1-16:

1. 4-[(dimethylamino)diazenyl]-5-methylselenophene-2-carboxamide (compound 1).
2. 3-[(dimethylamino)diazenyl]selenophene-2,5-dicarboxamide (compound 2).
3. 3-[(dimethylamino)diazenyl]-5-phenylselenophene-2-carboxamide (compound 3).
4. 3-[(dimethylamino)diazenyl]-5-(tert-butyl)selenophene-2-carboxamide (compound 4).
5. 3-[(dimethylamino)diazenyl]-4,5,6,7-tetrahydrobenzo[1,2-b]selenophene-2-carboxamide (compound 5).
6. 3-[(dimethylamino)diazenyl]selenopheno[2,3-b]pyridine-2-carboxamide (compound 6).
7. 3-[(dimethylamino)diazenyl]-5-phenylselenophene-2-carboxylic acid (compound 7).
8. 3-[(dimethylamino)diazenyl]-5-(tert-butyl)selenophene-2-carboxylic acid (compound 8).
9. 3-[(dimethylamino)diazenyl]-4,5,6,7-tetrahydrobenzo[1,2-b]selenophene-2-carboxylic acid (compound 9).
10. 3-[(dimethylamino)diazenyl]selenopheno[2,3-b]pyridine-2-carboxylic acid (compound 10).
11. 3-[(dimethylamino)diazenyl]-5-(tert-butyl)selenophene-2-carbonitrile (compound 11).
12. 3-methyl-6-phenylselenopheno[3,2-d]1,2,3-triazin-4-one (compound 12).
13. 6-(tert-butyl)-3-methylselenopheno[3,2-d]1,2,3-triazin-4-one (compound 13).
14. 3-methyl-6,7,8,9-tetrahydrobenzo[1,2-b]1,2,3-triazino[4,5-d]selenophen-4-one (compound 14).
15. 3-methyl-1,2,3-triazino[4',5'-5,4]selenopheno[2,3-b]pyridine-4-one (compound 15).
16. 3-methylbenzo[b]1,2,3-triazino[4,5-d]selenophen-4-one (compound 16).

In another aspect, the invention provides the synthesis of preferred compounds as well as their intermediates obtained during the process of synthesis, as described in examples 1-16.

In another aspect, pharmaceutically acceptable acid(s) and base addition salts of compounds of general formulae (I) and (II) comprise wide variety of organic and inorganic acids and bases and include but not limited to the physiologically acceptable salts which are often used in pharmaceutical industry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfate, sulfonate, benzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, tartrate and the like.

The pharmaceutically acceptable salts generally have enhanced aqueous solubility characteristics compared to the compound's native form from which they are derived, and thus are often more amenable to formulation as liquids or emulsions, and can have enhanced bioavailability.

In another aspect, the invention further provides a process for the preparation of the above said selenophene compounds and analogs of general formulae (I) and (II) and their pharmaceutically acceptable compositions.

The synthesis of selenopheno triazene analogs of formula (I), specifically the synthesis of 4-[(dimethylamino)diazenyl]-5-methylselenophene-2-carboxamide (compound 1) is achieved by the steps shown in scheme A.

Scheme-A

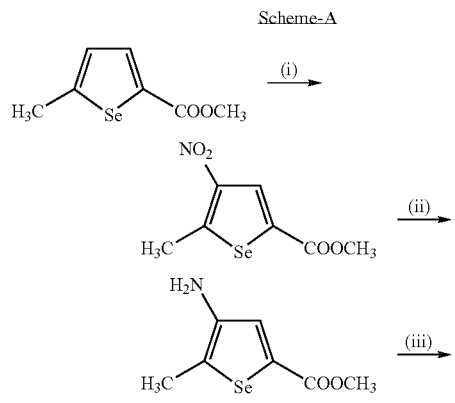

-continued

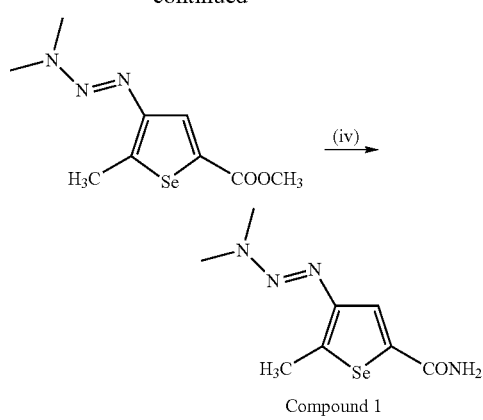

Compound 1

Reagents & conditions: (i) HNO₃, Ac₂O, room temperature (rt) (ii) Fe, HCl, MeOH, reflux, 1 h (iii) HCl, NaNO₂, K₂CO₃/dimethylamine, 0° C. (iv) Aq. NH₃, rt, 40 h.

Nitration of methyl 5-methylselenophene-2-carboxylate provided methyl 5-methyl-4-nitroselenophene-2-carboxylate. The nitro functionality is reduced to amines using suitable reducing agents, for example, iron powder or any other nitro reducing agents in good yield. Diazotization of methylamino-5-methylselenophene-2-carboxylate with sodium nitrite followed by treatment with potassium carbonate/dimethylamine provides methyl 4-[(dimethylamino)diazenyl]-5-methylselenophene-2-carboxylate. Treatment of the ester with ammonia gave the required 4-[(dimethylamino)diazenyl]-5-methylselenophene-2-carboxamide (compound 1).

The synthesis of selenopheno triazene analogs of formula (I), specifically the synthesis of 3-[(dimethylamino)diazenyl]selenophene-2,5-dicarboxamide (compound 2) is achieved by the steps shown in scheme B.

Scheme-B

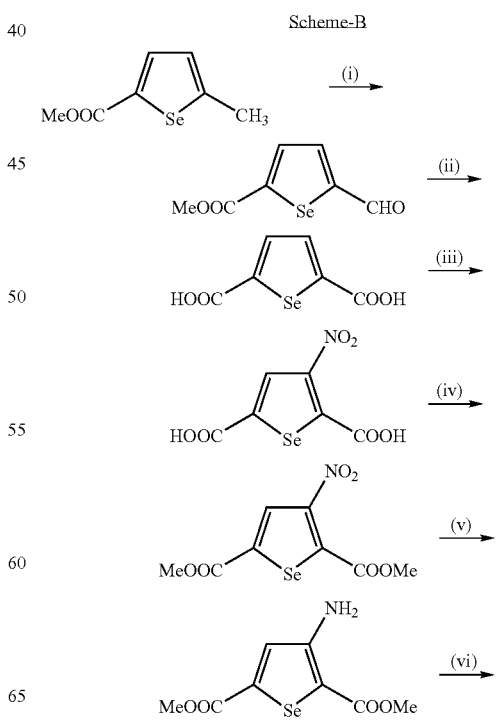

-continued

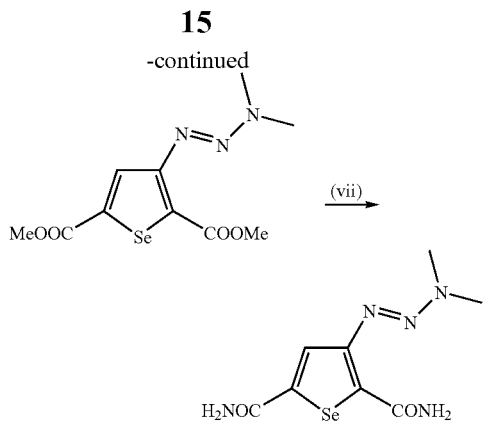

Compound 2

Reagents & conditions: (i) SeO₂, AcOH, reflux, 8 h (ii) AgNO₃, NaOH, rt, 1 h (iii) HNO₃, H₂SO₄, 0° C.-rt, 2 h (iv) MeOH, SOCl₂, reflux, 2 h (v) Fe, HCl, MeOH, reflux, 3 h (vi) HCl, NaNO₂, K₂CO₃/dimethylamine, 0° C., 2 h (vii) Aq. NH₃, rt, 24 h.

Oxidation of methyl 5-methylselenophene-2-carboxylate with selenium dioxide provided methyl 5-formylselenophene-2-carboxylate, which on further oxidation with silver nitrate gave selenophene-2,5-dicarboxylic acid. Nitration of selenophene-2,5-dicarboxylic acid and esterfication provided methyl 5-(methoxycarbonyl)-3-nitroselenophene-2-carboxylate in good yield. The nitro functionality is reduced to amines using suitable reducing agents, for example, iron powder or any other nitro reducing agents in good yield. Diazotization of methyl-amino-5-(methoxycarbonyl)selenophene-2-carboxylate with sodium nitrite followed by treatment with potassium carbonate/dimethylamine provides methyl 3-[(dimethylamino)diazenyl]-5-(methoxycarbonyl)selenophene-2-carboxylate. Treatment of the ester with ammonia gave the required 3-[(dimethylamino)diazenyl]selenophene-2,5-dicarboxamide (compound 2).

The synthesis of selenopheno triazene analogs of formula (I), specifically for compound 3 and compound 4, is achieved by the steps shown in scheme C.

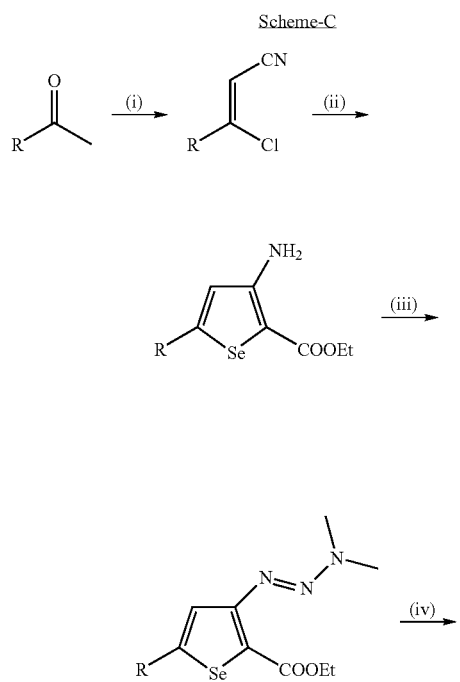

Scheme-C

-continued

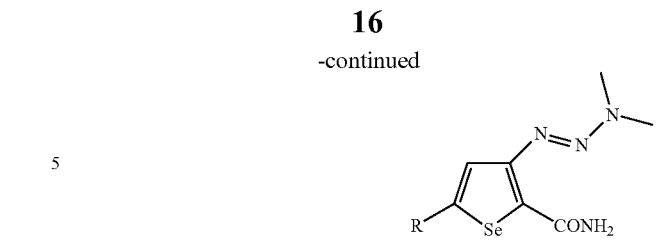

Compound 3: R = Ph
Compound 4: R = tert-butyl

Reagents & conditions: (i) POCl₃, DMF, 0° C., NH₂OH•HCl, 145-155° C., 30 min (ii) Na₂Se, DMF, ClCH₂COOEt, NaOMe, MeOH, 60-70° C., 5 h (iii) HCl, NaNO₂, K₂CO₃/dimethylamine, 0° C., 2 h (iv) Aq. NH₃, PEG-400, rt, 48 h.

The 3-chloro-3-substituted prop-2-enenitrile is prepared starting from the corresponding ketone with DMF-phosphorous oxychloride followed by hydroxylamine hydrochloride. The obtained products are reacted with sodium selenide, ethyl chloroacetate in presence of a base to provide 3-substituted ethyl-amino-selenophene-2-carboxylates in good yields. Diazotization of the amino compounds with sodium nitrite followed by treatment with potassium carbonate/dimethylamine provides triazine compounds. Treatment of the esters with ammonia in presence of PEG-400 gave the required 3-[(dimethylamino)diazenyl]-5-phenylselenophene-2-carboxamide (compound 3) and 3-[(dimethylamino)diazenyl]-5-(tert-butyl)selenophene-2-carboxamide (compound 4).

The synthesis of selenopheno triazene analogs of formula (I), specifically the synthesis of 3-[(dimethylamino)-diazenyl]-4,5,6,7-tetrahydrobenzo[1,2-b]selenophene-2-carboxamide (compound 5), is achieved by the steps shown in scheme D.

Scheme-D

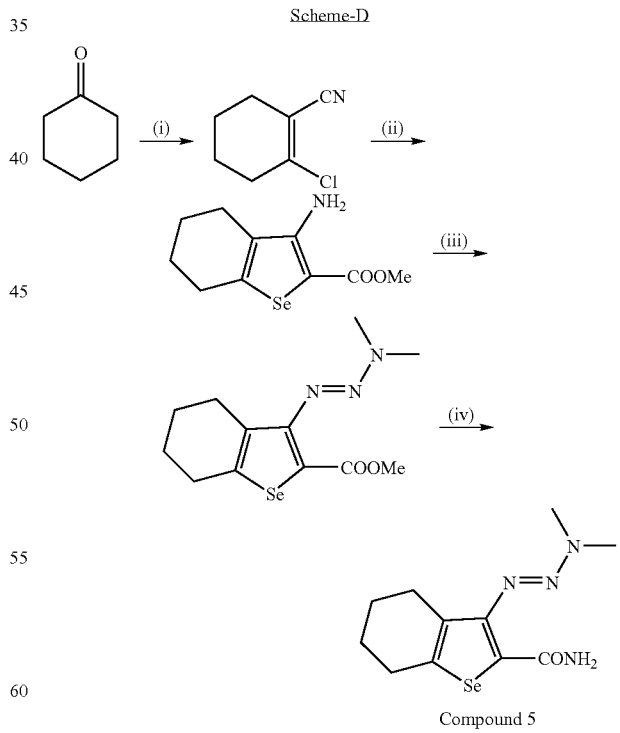

Compound 5

Reagents & conditions: (i) POCl₃, DMF, 0° C., NH₂OH•HCl, 145-155° C., 30 min (ii) Na₂Se, DMF, ClCH₂COOEt, NaOMe, MeOH, 60-70° C., 5 h (iii) HCl, NaNO₂, K₂CO₃/dimethylamine, 0° C., 1 h (iv) Aq. NH₃, PEG-400, rt, 66 h.

The 3-chlorocyclohex-1-enecarbonitrile is prepared starting from the cyclohexanone with DMF-phosphorous oxychloride and hydroxylamine hydrochloride, which is reacted with sodium selenide to provide ethyl-amino-4,5,6,7-tetrahydrobenzo[2,1-d]selenophene-2-carboxylate in good yield. Diazotization of ethyl-amino-4,5,6,7-tetrahydrobenzo[2,1-d]selenophene-2-carboxylate with sodium nitrite followed by treatment with potassium carbonate/dimethylamine provides methyl 3-[(dimethylamino)diazenyl]-4,5,67-tetrahydrobenzo[2,1-d]selenophene-2-carboxylate. Treatment of the ester with ammonia gave the required 3-[(dimethylamino)diazenyl]-4,5,6,7-tetrahydrobenzo[1,2-b]selenophene-2-carboxamide (compound 5).

The synthesis of selenopheno triazene analogs of formula (I), specifically the synthesis of 3-[(dimethylamino)-diazenyl]selenopheno[2,3-b]pyridine-2-carboxamide (compound 6) is achieved by the steps shown in scheme E.

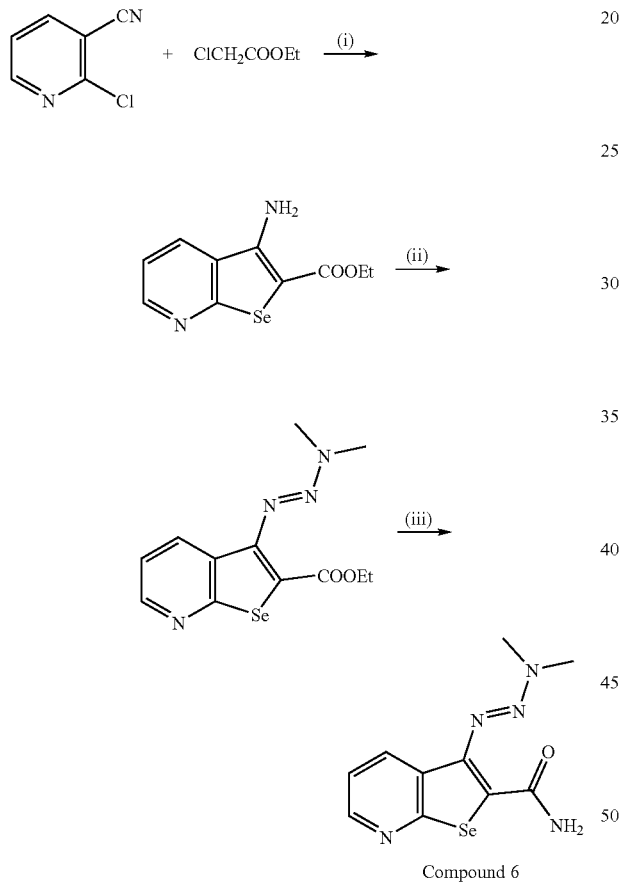

Compound 6

Reagents & conditions: (i) Na₂Se, DMF, NaOMe, MeOH, 60-70° C., 5 h (ii) HCl, NaNO₂, K₂CO₃/dimethylamine, 0° C., 1 h (iii) Aq. NH₃, rt, 16 h.

The ethyl-aminoselenopheno[2,3-b]pyridine-2-carboxylate is prepared starting from the 2-chloropyridine, sodium selenide and ethyl chloroacetate, which on diazotization with sodium nitrite followed by treatment with dimethylamine provides ethyl 3-[(dimethylamino)diazenyl]selenopheno[2,3-b]pyridine-2-carboxylate. Treatment of the ester with ammonia gave the required 3-[(dimethylamino)diazenyl]selenopheno[2,3-b]pyridine-2-carboxamide (compound 6).

The synthesis of selenopheno triazene analogs of formula (I), specifically the synthesis of compound 7 and compound 8 are achieved by the steps shown in scheme F.

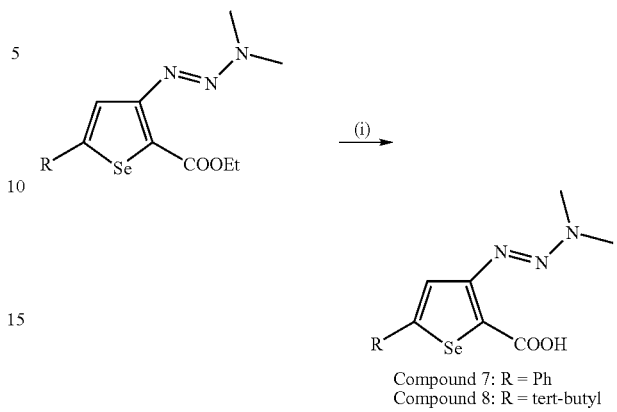

Compound 7: R = Ph
Compound 8: R = tert-butyl

Reagents & conditions: (i) MeOH, NaOH, rt, 16 h.

The hydrolysis of the corresponding (dimethylamino)diazenyl]selenophene esters with sodium hydroxide gave the required 3-[(dimethylamino)diazenyl]-5-phenylselenophene-2-carboxylic acid (compound 7) and 3-[(dimethylamino)diazenyl]-5-(tert-butyl)selenophene-2-carboxylic acid (compound 8).

The synthesis of selenopheno triazene analogs of formula (I), specifically the synthesis of 3-[(dimethylamino)-diazenyl]-4,5,6,7-tetrahydrobenzo[1,2-b]selenophene-2-carboxylic (compound 9) is achieved by the steps shown in scheme G.

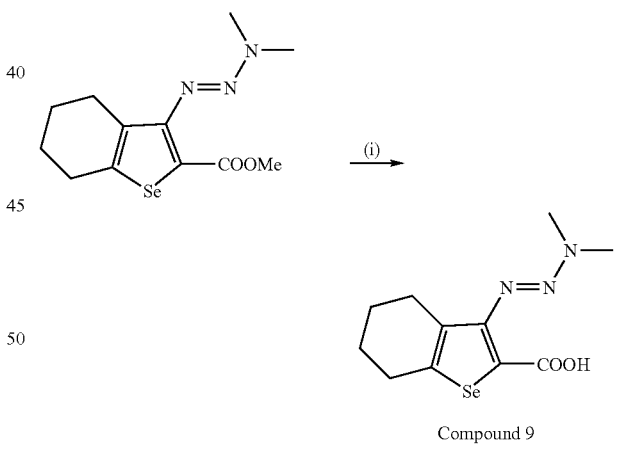

Compound 9

Reagents & conditions: (i) MeOH, NaOH, rt, 5 h

The hydrolysis of methyl 3-[(dimethylamino)diazenyl]-4,5,6,7-tetrahydrobenzo[2,1-d]selenophene-2-carboxylate with sodium hydroxide gave the required 3-[(dimethylamino)diazenyl]-4,5,6,7-tetrahydrobenzo[1,2-b]selenophene-2-carboxylic acid (compound 9).

The synthesis of selenopheno triazene analogs of formula (I), specifically the synthesis of 3-[(dimethylamino)-diazenyl]selenopheno[2,3-b]pyridine-2-carboxylic acid (compound 10) is achieved by the steps shown in scheme H.

Scheme-H

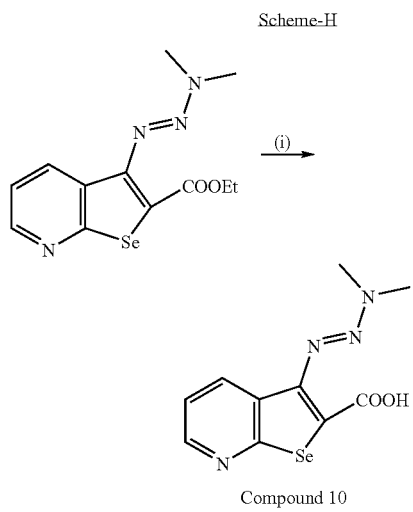

Compound 10

Reagents & conditions: (i) MeOH, NaOH, rt, 2 h.

The hydrolysis of ethyl 3-[(dimethylamino)diazenyl]selenopheno[2,3-b]pyridine-2-carboxylate with sodium hydroxide gave the required 3-[(dimethylamino)diazenyl]selenopheno[2,3-b]pyridine-2-carboxylic acid (compound 10).

The synthesis of selenopheno triazene analogs of formula (I), specifically the synthesis of compound 11 is achieved by the steps shown in scheme I.

Scheme-I

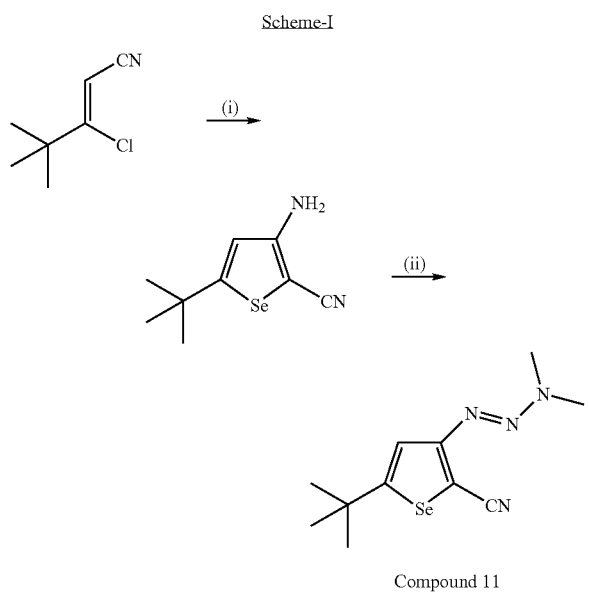

Compound 11

Reagents & conditions: (i) Na$_2$Se, DMF, ClCH$_2$CN, NaOMe, MeOH, 60-70° C., 5 h (ii) HBF$_4$, NaNO$_2$, K$_2$CO$_3$/dimethylamine, 0° C., 2 h.

The 3-amino-5-(tert-butyl)selenophene-2-carbonitrile is prepared starting from the 3-chloro-4,4-dimethylpent-2-enenitrile, sodium selenide and chloroacetonitrile, which on diazotization with sodium nitrite followed by treatment with dimethylamine gave the required 3-[(dimethylamino)diazenyl]-5-(tert-butyl)selenophene-2-carbonitrile (compound 11).

The synthesis of selenopheno triazene analogs of formula (II), specifically the synthesis of compound 12 and compound 13 are achieved by the steps shown in scheme J.

Scheme-J

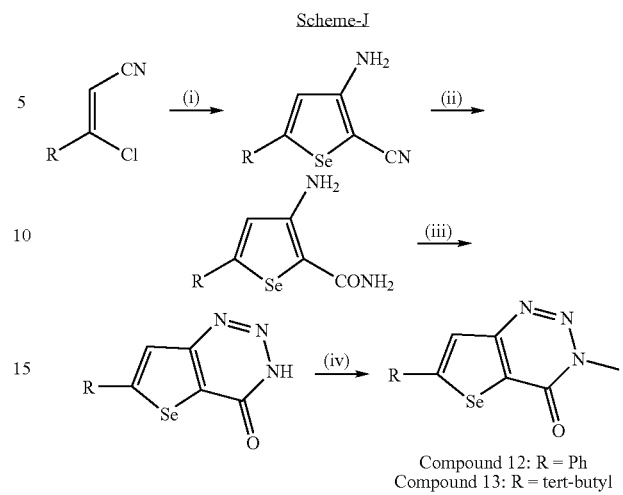

Compound 12: R = Ph
Compound 13: R = tert-butyl

Reagents & conditions: (i) Na$_2$Se, DMF, ClCH$_2$CN, NaOMe, MeOH, 60-70° C., 5 h (ii) aq. NaOH, EtOH, reflux, 45 min (iii) NaNO$_2$, H$_2$SO$_4$, 0° C., 1 h, rt, 1 h (iv) CH$_3$I, K$_2$CO$_3$, acetone, rt, 16 h.

The corresponding 5-substituted 3-amino-selenophene-2-carbonitriles are prepared starting from corresponding 3-substituted 3-chloro-prop-2-enenitrile, sodium selenide and chloroacetonitrile, which on treatment with aqueous sodium hydroxide gave the corresponding amides in good yield. Diazotization of the amines with sodium nitrite followed by treatment with iodomethane in presence of a base gave the required 3-methyl-6-phenylselenopheno[3,2-d]1,2,3-triazin-4-one (compound 12) and 6-(tert-butyl)-3-methylselenopheno[3,2-d]1,2,3-triazin-4-one (compound 13).

The synthesis of selenopheno triazene analogs of formula (II), specifically the synthesis of compound 14 is achieved by the steps shown in scheme K.

Scheme-K

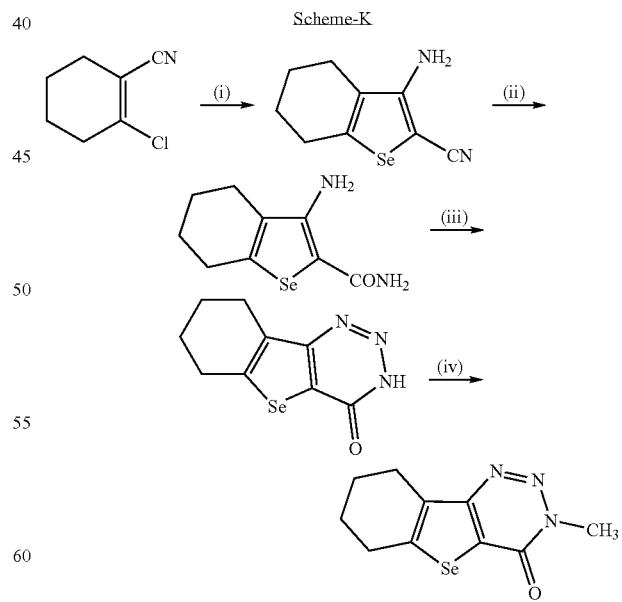

Compound 14

Reagents & conditions: (i) Na$_2$Se, DMF, ClCH$_2$CN, NaOMe, MeOH, 60° C., 3 h (ii) aq. NaOH, EtOH, reflux, 1 h (iii) NaNO$_2$, H$_2$SO$_4$, 0° C., 2 h (iv) CH$_3$I, K$_2$CO$_3$, acetone, PEG-400, rt, 16 h.

The 3-amino-4,5,6,7-tetrahydrobenzo[1,2-b]selenophene-2-carbonitrile is prepared starting from 2-chlorocyclohex-1-enecarbonitrile, sodium selenide and chloroacetonitrile, which on treatment with aqueous sodium hydroxide gave the corresponding amide in good yield. Diazotization of the amine with sodium nitrite followed by treatment with iodomethane in presence of a base gave the required 3-methyl-6,7,8,9-tetrahydrobenzo[1,2-b]1,2,3-triazino-[4,5-d]-selenophen-4-one (compound 14).

The synthesis of selenopheno triazene analogs of formula (II), specifically the synthesis of compound 15 and compound 16 are achieved by the steps shown in scheme L.

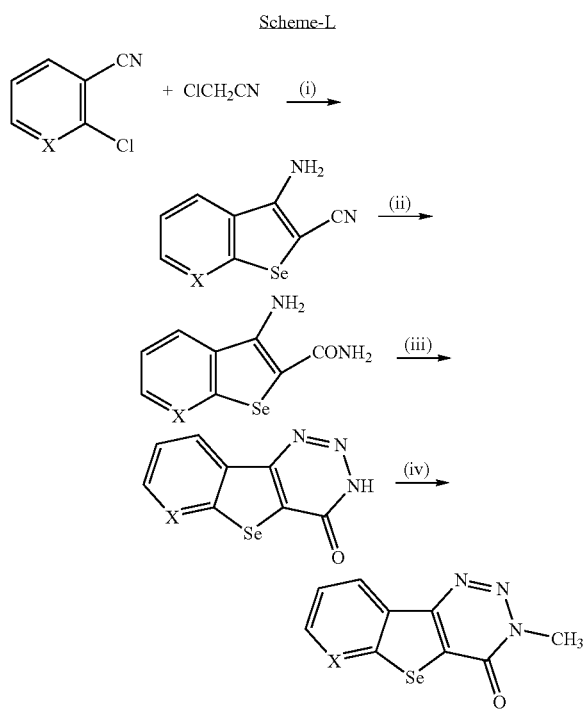

Compound 15 : X = N
Compound 16 : X = C

Reagents & conditions: (i) Na₂Se, DMF, NaOMe, MeOH, 60-70° C., 3 h (ii) aq. NaOH, EtOH, reflux, 45 min (iii) NaNO₂, H₂SO₄, 0° C., 2 h (iv) CH₃I, K₂CO₃, acetone, PEG-400, rt, 16 h.

The corresponding 3-amino-selenophenocarbonitriles are prepared starting from the 2-chloropyridine-3-carbonitrile or 2-chlorobenzonitrile, sodium selenide and chloroacetonitrile, which on treatment with aqueous sodium hydroxide gave the corresponding amides in good yield. Diazotization of the amines with sodium nitrite followed by treatment with iodomethane in presence of a base gave the required 3-methyl-1,2,3-triazino[4',5'-5,4]selenopheno[2,3-b]pyridine-4-one (compound 15) and 3-methylbenzo[b]1,2,3-triazino[4,5-d]selenophen-4-one (compound 16).

In another aspect, the invention provides pharmaceutical or veterinary compositions (hereinafter, referred to as a pharmaceutical composition) comprising selenopheno triazene analogs in combination with a pharmaceutically acceptable excipient(s) or carrier(s) or diluent(s).

In another aspect, the invention provides pharmaceutical or veterinary compositions comprising selenopheno triazene analogs in combination with a pharmaceutically acceptable excipient(s)/carrier(s)/diluent(s), further optionally comprising one or more pharmaceutically acceptable anti-cancer drugs.

In another aspect, the invention provides pharmaceutical or veterinary compositions comprising selenopheno triazene analogs in combination with a pharmaceutically acceptable excipient(s)/carrier(s)/diluent(s), further optionally comprising one or more pharmaceutically acceptable anti-angiogenic drugs.

In another aspect, the invention provides pharmaceutical or veterinary compositions (hereinafter, referred to as a pharmaceutical composition) comprising selenopheno triazene analogs that contains a melanin targeted analog as described above, in combination with a pharmaceutically acceptable excipient(s)/carrier(s)/diluent(s).

In another aspect, the invention provides novel compositions for use as pharmaceutical or veterinary compositions comprising selenopheno triazene analogs in combination with a pharmaceutically acceptable excipient(s)/carrier(s)/diluent(s), further optionally comprising one or more pharmaceutically acceptable drugs.

In another aspect, the pharmaceutically acceptable drugs can be one or more drugs selected from the list comprising anti-cancer drugs, anti-melanoma drugs, anti-metastatic melanoma drugs, anti-angiogenesis drugs, anti-inflammatory drugs, anti-obese drugs, anti-diabetic drugs, anti-metabolic disease drugs, biologic response modifying agents and other chemotherapy drugs.

In another aspect, the compositions of the methods described herein may comprise additional agents, such as adjuvants or antineoplastic agents. Antineoplastic agents include but are not limited to, RNAi reagents, tumor cells and antibodies. In various embodiments, the antineoplastic agent is selected from but not limited to:

5-fluorouracil or a pharmaceutically acceptable composition of 5-fluorouracil including but not limited to Adrucil®, Carac®, Efudex® and Fluoroplex®;

6-mercatopurine or a pharmaceutically acceptable 6-mercatopurine composition including but not limited to Purinethol®;

Actinomycin, aminoglutethimide or a pharmaceutically acceptable aminoglutethimide composition including but not limited to Cytadren®;

Anastrozole or a pharmaceutically acceptable Anastrozole composition including but not limited to Arimidex®;

bevacizumab or a pharmaceutically acceptable bevacizumab composition including but not limited to Avastin®;

Bleomycin;

Carboplatin;

Cactinomycin;

capecitabine or a pharmaceutically acceptable capecitabine composition including but not limited to Xeloda®;

cisplatin or a pharmaceutically acceptable cisplatin composition including but not limited to Platinol®;

clodronic acid or a pharmaceutically acceptable salt of clodronic acid or the pharmaceutically acceptable clodronic acid composition including but not limited to Bonefos® or Ostac®;

cyclophosphamide or a pharmaceutically acceptable cyclophosphamide composition including but not limited to Endoxan, Cytoxan®, Neosar®, Procytox®, and Revimmune®;

actinomycin D;

Docetaxel or a pharmaceutically acceptable Docetaxel composition including but not limited to Taxotere®;

Doxorubicin or a pharmaceutically acceptable Doxorubicin composition including but not limited to Adriamycin®;

Epirubicin or a pharmaceutically acceptable Epirubicin composition including but not limited to Ellence® and Pharmorubicin®);

Etoposide or a pharmaceutically acceptable Etoposide composition including but not limited to Eposin®, Etopophos®, Vepesid®, and VP-16®;

Exemestane or a pharmaceutically acceptable Exemestane composition including but not limited to Aromasin®;

Fluoxymesterone or a pharmaceutically acceptable Fluoxymesterone composition including but not limited to Halotestin®;

Letrozole or a pharmaceutically acceptable Letrozole composition including but not limited to Femara®;

Leucovorin calcium;

Megestrol or Megestrol acetate or a pharmaceutically acceptable Megestrol acetate composition including but not limited to Megace®;

Methotrexate,

Mitomycin or a pharmaceutically acceptable Mitomycin composition including but not limited to Mutamycin®;

Mitoxantrone or a pharmaceutically acceptable Mitoxantrone composition including but not limited to Novantrone®;

Paclitaxel or a pharmaceutically acceptable Paclitaxel composition including but not limited to Taxol®;

Pamidronate or a pharmaceutically acceptable Pamidronate composition including but not limited to Aredia®;

Prednisone;

tamoxifen or a pharmaceutically acceptable tamoxifen composition including but not limited to Nolvadex®, Istubal®, Tamofen®, Tamone®, Tamoplex®, and Valodex®;

Trastuzumab or a pharmaceutically acceptable Trastuzumab composition including but not limited to Herceptin®;

Thiotepa;

Vinblastine or a pharmaceutically acceptable Vinblastine composition including but not limited to Velbe®;

Vincristine or a pharmaceutically acceptable Vincristine composition including but not limited to Oncovin®; or Vinorelbine or a pharmaceutically acceptable Vinorelbine composition including but not limited to Navelbine®.

In another aspect, pharmaceutically acceptable or plant based angiostatic drugs that can be used for preparing compositions of the present invention include one or more pharmaceutical drugs selected from but not limited to angiostatin, endostatin, thalidomide, osteopontin, maspin, canstatin, proliferin related protein, restin and other related molecules.

In another aspect, the composition(s) comprise immunomodulatory agents, such as cytokines. Cytokines include but not limited to IFN-α, interleukins (IL-1, IL-2, IL-4, IL-9, IL-11, IL-12), monoclonal antibodies, interferons (interferon-γ), various types of colony stimulating factors (CSF, GM-CSF, G-CSF), TNF-α receptor blocker drugs and the like. In another embodiment, the composition(s) further comprise an immunomodulatory drug, such as cyclophosphamide. In other embodiments, the composition(s) comprise adjuvants.

In another aspect, the compound(s) or composition(s) of the present invention are useful for treating cancer in conjunction with one or more therapies including but not limited to anti-angiogenesis therapy, chemotherapy, cytokine therapy, radiotherapy, gene therapy, hormonal therapy, surgery, vaccination, biological therapy or a combination thereof.

In another aspect, the compound(s) or composition(s) of the present invention are useful for treating cancer wherein a cancer cell can originate from any part of the body, and not limited to any organ/tissue of a warm blooded animal such as brain, lung, adrenal glands, pituitary gland, breast, prostate, pancreas, ovaries, gastrointestinal tract, kidneys, liver, spleen, testicles, cervix, upper, lower, or middle esophagus either primary, secondary or tertiary tumors of all types.

In another aspect, the compound(s) or composition(s) of the present invention are useful for the amelioration of potentially useful apoptosis markers including but not limited to cleaved cytokeratin-18 (c-CK18), cleaved caspase-3 (c-cas-3), cleaved lamin A (c-lam-A), phosphorylated histone H2AX (γH2AX), cleaved poly(ADP ribose) polymerase (c-PARP), and translocation of apoptosis-inducing factor (AIF), Bcl-2-associated X protein (Bax), Claudin-18 (CLD-18), cytokeratin-18 (CK 18), Apo 2.7 and Apo-2 Ligand/(TNF)-related apoptosis-inducing ligand, and cell cycle regulatory proteins such as Cyclin dependent kinase-1 (CDK-1), CDK-4, CDK-6, phospho-Retinoblastoma (pRb), Cyclin D1 and p 16INK4A to control the cancer cell growth.

In another aspect, the novel compounds and compositions of the present invention are also potent angiogenesis inhibitors and can be effectively used alone or as a pharmaceutical composition(s) to prevent, treat and cure diseases including but not limited to cancer, cancer-related, cancer-associated, angiogenesis related and other vascular diseases.

In another aspect, the present invention relates to the use of novel selenopheno triazene analogs of general formulae (I) and (II), their geometrical isomeric forms, stereoisomers, configurational isomers, polymorphs, hydrates, solvates and pharmaceutically acceptable salts thereof for metastatic malignant melanoma and for carcinomas of the solid tumors, and all other cancers including but not limited to lymphomas, sarcomas, leukemias and gliomas either alone or in combination with other approved chemotherapeutic drugs.

In another aspect, the invention further provides a method of inhibiting angiogenesis and for ameliorating the angiogenesis modulators which include but not limited to Vascular endothelial Growth Factor (VEGF), Platelet Derived Growth Factor (PDGF), Tissue Growth Factor-beta (TGF-beta) and Fibroblast Growth Factor (FGF), Thrombospondin-1 (TSP-1), Angiopoietin-1 (Ang-1), Ang-2, Interleukin-8 (IL-8) etc., in warm blooded animals in need thereof comprising administering a therapeutically effective amount of selenopheno triazene analogs of general formula (I) or formula (II) or their pharmaceutical composition(s).

In another aspect, the present invention provides a method for remodeling of the vasculatures by modifying the proliferation, migration, invasion of endothelial cells and vascular smooth muscle cells in warm blooded animals in need thereof.

The invention provides a method of treating a mammal having, or at risk of, a vascular indication associated with TGF-beta deficiency. Another preferred embodiment is an agent that increases the level of TGF-beta which is capable of binding to the TGF-beta receptors.

In another aspect, the pharmaceutical compositions of the present invention may be in any form which allows for the composition to be administered to a subject. For example, the composition may be in the form of a solid, liquid or gas (aerosol). Typical routes of administration include, without limitation, topical, parenteral, sublingual, intraperitoneal (IP), intravenous (IV), oral (PO), intramuscular (IM), intracutaneous (IC), intradermal (ID), intrauterine, intratumoral (IT) and intrarectal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a subject. Compositions that will be administered take the form of one or more dosage units, where for example, a tablet may be a single dosage unit, and a container of triazene analog in topical form may hold a plurality of dosage units and using nanoparticles of different sizes in an emulsion to a warm blooded animal, in need thereof.

In another aspect, the pharmaceutical compositions of the present invention may be delivered in any form of dosage forms including but not limited to Liposome-based, Polymeric surfactant-based, Biodegradable block copolymers, Microencapsulation and Nanoparticles. Further, the Nanoparticles dosage forms comprise Polymer-lipid hybrid nanoparticle system, Carbon nanotubes, Liquid filled nanoparticles, Liposomes Encapsulating Chitosan Nanoparticles, Organically Modified Silica Nanoparticles, Fluorocarbon nanoparticles and Dendrimer nanotechnology.

In another aspect, the pharmaceutical compositions of the present invention can be useful for the preparation of medicaments for use in warm blooded animals in need thereof.

It will be evident to those of ordinary skill in the art that the optimal dosage of the active ingredient(s) in the pharmaceutical composition(s) will depend on a variety of factors. Relevant factors include, without limitation, the type of subject (e.g., human), the particular form of the active ingredient, the manner of administration and the composition(s) employed.

In another aspect, the pharmaceutical composition(s) of the present invention may include a compound of general formula (I) or (II) as described herein, in admixture with one or more carriers. The carrier(s) may be particulate, so that the compositions are, for example, in tablet or powder form. The carrier(s) may be liquid, with the compositions being, for example oral syrup or injectable liquid. In addition, the carrier(s) may be gaseous, so as to provide an aerosol composition useful in e.g., inhalatory administration.

In another aspect the invention provides the administration of the inventive compounds in any suitable form. When intended for oral administration, the composition is preferably in either solid or liquid form, where semi-solid, semi-liquid, suspension and gel forms are included within the forms considered herein as either solid or liquid.

In another aspect, a solid composition for oral administration can be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxy methyl cellulose, ethyl cellulose, microcrystalline cellulose, or gelatin; excipients such as starch, lactose or dextrins, disintegrating agents such as alginic acid, sodium alginate, primogel, corn starch and the like; lubricants such as magnesium stearate or sterotex; glidants such as colloidal silicon dioxide; sweetening agents such as sucrose or saccharin, a flavoring agent such as peppermint, methyl salicylate or orange flavoring, and a coloring agent.

In another aspect, the composition can be formulated as a capsule, e.g., a gelatin capsule, it may contain, in addition to materials of the above type, a liquid carrier such as polyethylene glycol or fatty oil. The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

In another aspect, the liquid pharmaceutical composition of the invention, whether they may be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylene diamine tetra acetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition comprising present inventive compounds of the general formula (I) or (II) are preferably sterile.

In another aspect, the composition may include various materials which modify the physical form of a solid or liquid dosage unit. For example the composition may include various materials which modify the physical form of a solid or liquid dosage unit. For example, the composition may include materials that form a coating shell around the active ingredients. The materials which form the coating shell are typically inert, and may be selected from, for example sugar, shellac, and other enteric coating agents. Alternatively, the active ingredients may be encased in a gelatin capsule.

In another aspect, the composition in solid or liquid form may include an agent which binds to the active melanin targeted analog component(s) or derivatives thereof and thereby assists in the delivery of the active components. Suitable agents which may act in this capacity comprise a monocyclic, bicyclic, tricyclic, polycyclic aromatic, heterocyclic hydrophobic ring system as backbone moieties.

In another aspect, the pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in any suitable form such as monophasic, biphasic or triphasic systems in order to deliver the active ingredient(s). Delivery of the aerosol includes the necessary container, activators, valves, sub-containers, spacers and the like, which together may form a kit. Preferred aerosols may be determined by one skilled in the art, without undue experimentation.

In another aspect, the invention concerns a method for treatment wherein an effective amount of a compound or composition(s) of the present invention is used to treat diseases of cells having melanoma and other cancers. These cells are typically mammalian cells. Methods of administering effective amounts of the analogs or derivatives are well known in the art and include the administration of inhalation, oral or parenteral forms. Such dosage forms includes, but are not limited to, parenteral solutions, tablets, capsules, sustained release implants and transdermal delivery systems; or inhalation dosage systems employing dry powder inhalers or pressurized multi-dose inhalation devices. The dosage amount and frequency are selected to create an effective level of the agent without harmful effects. It will generally have a dosage range of about 0.1 to 500 mg/kg/day for efficacy, and typically about 2 to 100 mg/kg/day where administered orally or intravenously and about 0.1 to 4 mg/kg/day where administered intranasally or by inhalation.

In another aspect, a liquid composition intended for either parenteral or oral administration should contain a therapeutically effective amount of the inventive compounds of the general formula (I) or (II). Typically, this amount is at least 0.01% of the composition. When intended for oral administration, this amount may be varied to be between 0.01 and 70% of the weight of the composition. Preferred oral compositions contain between 4% and about 50% of the active triazene compound. Preferred compositions and preparations according to the present invention are prepared so that a parenteral dosage unit contains between 0.01% and 1% by weight of inventive compound.

In another aspect, the pharmaceutical composition of the present invention may be intended for any suitable administration such as topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or ionophoresis device. Topical formulations may contain a concentration of the inventive compound from about 0.1 to about 10% w/v (weight per unit volume).

In another aspect, the composition of the present invention may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

In another aspect, the invention employs a method of administration wherein a composition intended to be administered by injection can be prepared by combining the selenopheno triazene analog or derivative thereof with water so as to form a solution. A surfactant may be added to facilitate the formation of a homogeneous solution or suspension. Surfactants are compounds that non-covalently interact with the triazene analog or derivative so as to facilitate dissolution or homogeneous suspension of the triazene analog or derivative in the aqueous delivery system.

In another aspect, the inventive selenopheno triazene analogs of general formulae (I) and (II) are used in the treatment of melanoma, Hodgkin's lymphoma, carcinomas, sarcomas, gliomas, and other cancers in warm blooded animals in need thereof.

In another embodiment, the present invention relates to the method of treating metastatic malignant melanoma and for carcinomas of the solid tumors, and all other cancers of solid, liquid or lymphatic origin including but not limited to lymphomas, sarcomas and gliomas comprising administering to a warm blooded animal in need thereof a therapeutically effective dose of at least one compound selected from the novel selenophene compounds of general formulae (I) and (II), their geometrical isomeric forms, stereoisomers, configurational isomers, polymorphs, hydrates, solvates and pharmaceutically acceptable salts thereof.

In another aspect, the present invention relates to the method of treating metastatic malignant melanoma and for carcinomas of the solid tumors, and all other cancers including but not limited to lymphomas, sarcomas and gliomas comprising administering to a warm blooded animal in need thereof a therapeutically effective dose of composition comprising at least one compound selected from the novel selenophene compounds of general formulae (I) and (II), their geometrical isomeric forms, stereoisomers, configurational isomers, polymorphs, hydrates, solvates and pharmaceutically acceptable salts thereof in combination with pharmaceutically acceptable excipient(s)/diluent(s)/carrier(s), further optionally containing one or more drug(s).

The present invention is provided by the examples given below, which are provided by the way of illustration only, and should not be considered to limit the scope of the invention. Variation and changes, which are obvious to one skilled in the art, are intended to be within the scope and nature of the invention, which are defined in the appended claims.

EXAMPLES

Example 1

Synthesis of 4-[(dimethylamino)diazenyl]-5-methylselenophene-2-carboxamide (compound 1)

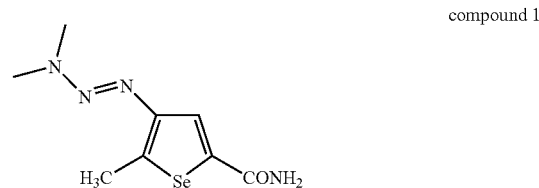

compound 1

Step a:

Methyl 5-methyl-4-nitroselenophene-2-carboxylate: To an ice cold (0-10° C.) solution of methyl 5-methylselenophene-2-carboxylate (5.4 g, 26.6 mmol) in acetic anhydride (15 mL) was added an ice cold mixture of nitric acid (5.5 mL, 61.1 mmol, 70%) and acetic anhydride (10 mL) for 10 min. The reaction mixture was slowly allowed to room temperature (rt) for 1 h and stirred at rt for 16 h. The mixture was poured into ice cold water and stirred for 10 min. The solution was extracted with chloroform (3×100 mL) and the combined organic layer was washed with water, brine and dried over sodium sulfate. The solution was filtered and evaporated the solvent. The residue was chromatographed over silica gel column using hexane-ethyl acetate (90:10) as eluents to give the product as an pale yellow color solid (2.3 g, 35%), mp 90-92° C. $^1$H NMR (400 MHz, CDCl$_3$): δ 8.54 (1H, s, H-3), 3.90 (3H, s, —COOCH$_3$), 2.90 (3H, s, —CH$_3$).

Step b:

Methyl-amino-5-methylselenophene-2-carboxylate: To a solution of methyl 5-methyl-4-nitroselenophene-2-carboxylate (2.3 g, 9.28 mmol) in a mixture of water (5 mL) and methanol (40 mL) was added conc. hydrochloric acid (1.0 mL). To the above solution was added iron powder (2.6 g, 46.4 mmol) followed by ammonium chloride (2.5 g, 46.4 mmol) at rt. The reaction mixture was refluxed for 1 h and was then allowed to cool to rt. The solution was filtered and basified with saturated sodium bicarbonate solution. The solution was extracted with ethyl acetate (4×100 mL) and the combined organic layer was dried over sodium sulfate and filtered. Solvent was evaporated and the residue was chromatographed over silica gel column using hexane-ethyl acetate (80:20) as eluent to give methyl 4-amino-5-methylselenophene-2-carboxylate (1.6 g, 79%), mp 66-68° C. $^1$H NMR (400 MHz, DMSO-d$_6$): δ 7.57 (1H, s, H-3), 4.72 (2H, br s, —NH$_2$), 3.73 (3H, s, —COOCH$_3$), 2.24 (3H, s, —CH$_3$).

Step c:

Methyl 4-[(dimethylamino)diazenyl]-5-methylselenophene-2-carboxylate: To a solution of methyl 4-amino-5-methylselenophene-2-carboxylate (1.2 g, 5.5 mmol) and conc. HCl (2.2 mL, 0.803 g, 22 mmol) in water (12.5 mL) was added sodium nitrite (0.42 g, 6.05 mmol) in portions for 5 min at 0° C. After stirring at 0-5° C. for 0.5 h, the reaction mixture was added to the solution of potassium carbonate (2.9 g, 20.9 mmol) and dimethylamine (2.23 mL, 40%, 19.8 mmol) in water (15.6 mL) at 0° C. The mixture was stirred at 0-10° C. for 1 h and poured into ice cooled water. The solution was extracted with chloroform (3×100 mL) and the combined chloroform layer was washed with water, brine and dried over sodium sulfate. The solution was filtered and evaporated the solvent. The residue was chromatographed over silica gel column using hexane-EtOAc (95:5) as eluents to give the product as a green color solid (550 mg, 36%), mp 80-82° C. IR (neat) $v_{max}$ 2949, 1708, 1242, 1175, 1150, 1071, 1054, 920, 876 cm$^{-1}$; $^1$H NMR (400 MHz, CDCl$_3$): δ 8.21 (1H, s, H-3), 3.84 (3H, s, —COOCH$_3$), 3.27 (6H, br s, —N(CH$_3$)$_2$), 2.62 (3H, s, Ar—CH$_3$); LC-MS (positive ion mode): m/z 276 (M+H)$^+$.

Step d:

4-[(Dimethylamino)diazenyl]-5-methylselenophene-2-carboxamide: To an ice cold (0-5° C.) solution of ammonium hydroxide (40 mL) was added a solution of methyl 4-[(dimethylamino)diazenyl]-5-methylselenophene-2-carboxylate (550 mg) in THF (10 mL) for 5 min and stirred at rt for 40 h. The solution was poured into ice cooled water and extracted with chloroform (3×100 mL). The combined organic layer was washed with water, brine and dried over sodium sulfate. The solution was filtered and evaporated the solvent. The residue was chromatographed over silica gel column using chloroform-methanol (96:4) as eluents to give the product as off-white solid (220 mg, 42%), mp 170-172° C. IR (neat) $v_{max}$ 3385, 3188, 2914, 1644, 1604, 1326, 1120, 1066 cm$^{-1}$; $^1$H NMR (400 MHz, CDCl$_3$): δ 7.87 (1H, s, H-3), 5.67 (2H, br s, —CONH$_2$), 3.28 (6H, br s, N(CH$_3$)$_2$), 2.63 (3H, s, Ar—CH$_3$); LC-MS (positive ion mode): m/z 261, 259 (M+H)$^+$.

Example 2

Synthesis of 3-[(dimethylamino)diazenyl]selenophene-2,5-dicarboxamide (compound 2)

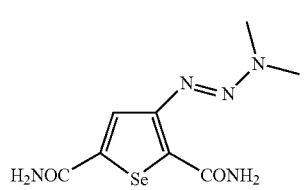

compound 2

Step a:

Methyl 5-formylselenophene-2-carboxylate: To a solution of methyl 5-methylselenophene-2-carboxylate (5.0 g, 24.6 mmol) in acetic acid (30 mL) was added selenium dioxide (10.84 g, 98.4 mmol) at rt and the mixture was refluxed for 8 h. The cooled reaction mixture was poured into ice cooled water and stirred for 15 min. The solution was extracted with chloroform (3×100 mL) and the combined organic layer was washed with water, brine and dried over sodium sulfate. The solution was filtered and evaporated the solvent. The residue was chromatographed over silica gel column using hexane-EtOAc (9:1) as eluents to give the product as pale yellow color solid (4.0 g, 75%), mp 63-65° C.; $^1$H NMR (400 MHz, CDCl$_3$): δ 9.84 (1H, s, —CHO), 8.11 (1H, d, J=4.0 Hz, H-3), 7.99 (1H, d, J=4.0 Hz, H-4), 3.92 (3H, s, —COOCH$_3$).

Step b:

Selenophene-2,5-dicarboxylic acid: A solution of silver nitrate (6.26 g, 36.86 mmol) in water (10 mL) was added to methyl 5-formylselenophene-2-carboxylate (4.0 g, 18.43 mmol) at 0° C. for 5 min. Then a solution of sodium hydroxide (3.05 g, 76.34 mmol) in water (10 mL) was added to the reaction mixture at the same temperature for 5 min and stirred the mixture at room temperature (rt) for 1 h. The cooled reaction mixture was poured into ice cooled water and acidified with dil. HCl. The solution was extracted with ethyl acetate (3×100 mL) and the combined organic layer was washed with water, brine and dried over sodium sulfate. The solution was filtered and evaporated the solvent to give the product as off-white color solid (3.2 g, 80%), mp 293-295° C. $^1$H NMR (400 MHz, DMSO-d$_6$): δ 13.48 (2H, br s, 2×—COOH), 7.82 (2H, s, H-3,4); LC-MS (negative ion mode): m/z 219, 217 (M−H)$^−$.

Step c:

3-Nitroselenophene-2,5-dicarboxylic acid: Nitric acid (5.65 mL, 125.55 mmol, 70%) was added slowly to a mixture of selenophene-2,5-dicarboxylic acid (11 g, 50.2 mmol) in sulfuric acid (21.87 mL, 401.77 mmol) at 0-5° C. for 15 min. The mixture was allowed to rt with stifling slowly for 2 h, poured into ice cold water and stirred for 30 min. The solution was extracted with ethyl acetate (3×200 mL) and the combined organic layer was washed with water, brine and dried over sodium sulfate. The solution was filtered and evaporated the solvent to give the product as pale yellow color solid (10 g, 76%, it is a mixture of 2 compounds).

Step d:

Methyl 5-(methoxycarbonyl)-3-nitroselenophene-2-carboxylate: To a solution of 3-nitroselenophene-2,5-dicarboxylic acid (10 g, 37.73 mmol; mixture of 2 compounds) in methanol (100 mL) was added thionyl chloride (10.9 mL, 150.92 mmol) drop wise under stirring at ice cold temperature. The reaction mixture was refluxed for 2 h and attained to rt. The mixture was poured into ice cooled water and stirred for 15 min. The solution was extracted with chloroform (3×200 mL) and the combined organic layer was washed with water, dil. sodium bicarbonate solution, brine, dried over sodium sulfate and filtered. Solvent was evaporated and the residue was chromatographed over silica gel column using hexane-ethyl acetate (95:5) as eluents to give the product as an pale yellow color oil (8.5 g, close mixture of two compounds). The oily product was stirred with hexane (10 mL) and decanted the hexane layer. The process was repeated for 3 more times to give the product as a yellow color solid (7.85 g; 71%). Small sample was recrystallized from hexane-chloroform for identification; IR (neat) $v_{max}$ 3426, 1729, 1537, 1248, 1079, 1020 cm$^{-1}$; $^1$H NMR (400 MHz, CDCl$_3$): δ 8.33 (1H, s, H-4), 3.95 (3H, s, —COOCH$_3$), 3.94 (3H, s, —COOCH$_3$); $^{13}$C NMR (100 MHz, CDCl$_3$): δ 161.5, 160.7, 148.6, 141.3, 141.2, 130.0, 53.7, 53.2.

Step e:

Methyl-amino-5-(methoxycarbonyl)selenophene-2-carboxylate: To a solution of methyl 5-(methoxycarbonyl)-3-nitroselenophene-2-carboxylate (8.0 g, 27.3 mmol) in a mixture of water (20 mL) and methanol (150 mL) was added conc. hydrochloric acid (2.75 mL, 27.3 mmol). To the above solution was added iron powder (7.64 g, 136.5 mmol) followed by ammonium chloride (7.3 g, 136.5 mmol) at rt. The reaction mixture was refluxed for 3 h and was then allowed to cool to rt. The solution was filtered and basified with saturated sodium bicarbonate solution. The solution was extracted with ethyl acetate (4×200 mL) and the combined organic layer was washed with brine, dried over sodium sulfate and filtered. Solvent was evaporated and the residue was chromatographed over silica gel column using hexane-ethyl acetate (95:5) as eluent to give the product as pale yellow color solid (5.8 g, 41%), mp 144-146° C. IR (neat) $v_{max}$. 3449, 3339, 1673, 1604, 1556, 1285, 1217, 1125, 1023 cm$^{-1}$; $^1$H NMR (400 MHz, CDCl$_3$): δ 7.55 (1H, s, H-4), 5.57 (2H, s, —NH$_2$), 3.86 (3H, s, —COOCH$_3$), 3.82 (3H, s, —COOCH$_3$); LC-MS (negative ion mode): m/z 264, 262 (M–H)$^-$.

Step f:

Methyl 3-[(dimethylamino)diazenyl]-5-(methoxycarbonyl)selenophene-2-carboxylate: To a solution of methylamino-5-(methoxycarbonyl)selenophene-2-carboxylate (0.6 g, 2.28 mmol) and conc. HCl (1.0 mL, 9.12 mmol) in water (5.7 mL) was added sodium nitrite (173 mg, 2.51 mmol) in portions for 5 min at 0° C. After stifling at 0-5° C. for 0.5 h, the reaction mixture was added to the solution of potassium carbonate (1.1 g, 8.66 mmol) and dimethylamine (1.0 mL, 40%, 8.21 mmol) in water (6.8 mL) at 0° C. The mixture was stirred at 0-5° C. for 2 h and poured into ice cold water. The solution was extracted with chloroform (3×100 mL) and the combined chloroform layer was washed with water, brine and dried over sodium sulfate. The solution was filtered and evaporated the solvent. The residue was chromatographed over silica gel column using hexane-EtOAc (90:10) as eluents to give the product as a orange color solid (250 g, 34%), mp 122-124° C. $^1$H NMR (400 MHz, CDCl$_3$): δ 8.29 (1H, s, H-4), 3.88 (3H, s, —COOCH$_3$), 3.87 (3H, s, —COOCH$_3$), 3.52 (3H, s, —N—CH$_3$), 3.28 (3H, s, —N—CH$_3$); LC-MS (positive ion mode): m/z 320, 318 (M+H)$^+$.

Step g:

3-[(Dimethylamino)diazenyl]-selenophene-2,5-dicarboxamide: To an ice cold (0-5° C.) solution of ammonium hydroxide (36 mL) was added a solution of methyl 3-[(dimethylamino)diazenyl]-5-(methoxycarbonyl)selenophene-2-carboxylate (650 mg) in THF (15 mL) for 5 min and stirred at rt for 24 h. The solution was poured into ice cooled water and extracted with chloroform (3×100 mL). The combined organic layer was washed with water, brine and dried over sodium sulfate. The solution was filtered and evaporated the solvent. The residue was chromatographed over silica gel column using chloroform-methanol (92:8) as eluents to give the product as off-white solid, which was recrystallized from chloroform-methanol (180 mg, 30%), mp 266-268° C. IR (KBr) $v_{max}$ 3436, 3347, 3173, 2920, 1645, 1609, 1336, 1198, 1108, 879, 801 cm$^{-1}$; $^1$H NMR (400 MHz, DMSO-d$_6$): δ 8.28 (1H, s, H-4), 8.13 (1H, br s, —CONH$_2$), 7.90 (1H, br s, —CONH$_2$), 7.80 (1H, br s, —CONH$_2$), 7.50 (1H, br s, —CONH$_2$), 3.57 (3H, s, —N—CH$_3$), 3.19 (3H, s, —N—CH$_3$); $^{13}$C NMR (100 MHz, DMSO-d$_6$): δ 163.9, 163.7, 150.7, 147.0, 135.1, 123.3, 43.5, 36.7; LC-MS (positive ion mode): m/z 288, 290 (M+H)$^+$.

Example 3

Synthesis of 3-[(dimethylamino)diazenyl]-5-phenylselenophene-2-carboxamide (compound 3)

compound 3

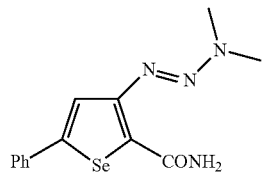

Step a:

3-Chloro-3-phenylprop-2-enenitrile: To an ice cold (0-5° C.) dimethylformamide (2.56 mL, 33.32 mmol) was added phosphorous oxychloride (1.56 mL, 16.66 mmol) dropwise with stirring for 15 min. To this cold mixture, acetophenone (1.0 g, 8.3 mmol) was added dropwise maintaining the temperature of the reaction mixture between 45-55° C. for 10 min. The reaction mixture was slowly allowed to rt and stand for 30 min. To the reaction mixture, 0.5 mL of a total solution of hydroxylamine hydrochloride (2.31 g, 33.32 mmol) in dry DMF (3.3 mL) was added and the mixture was stirred at 70-80° C. for 5 min. Then the remaining solution of hydroxylamine hydrochloride in DMF was added thereafter at such a rate that the temperature of the reaction mixture rise above 145-155° C. After completion of the addition, the reaction mixture was allowed to rt for 30 min and diluted with cold water (100 mL). The solution was extracted with chloroform (3×100 mL) and the chloroform layer was washed with water, brine and dried over sodium sulfate. The solution was filtered and evaporated the solvent. The residue was chromatographed over silica gel using hexane-ethyl acetate (98:2) as eluent to give the product as an oil (0.72 g, 53%). $^1$H NMR (400 MHz, CDCl$_3$): δ 7.64-7.67 (2H, m, Ar—H), 7.43-7.53 (3H, m, Ar—H), 6.02 (1H, s, =CH).

Step b:

Preparation of sodium selenide: Selenium (0.83 g) was added to a solution of sodium hydroxide (2.32 g) and sodium formaldehyde sulfoxylate (3.84 g) in water (11 mL). After stifling for 1 h at 50° C., the white precipitate was filtered under nitrogen atmosphere and rapidly used for the next step.

Ethyl 3-amino-5-phenylselenophene-2-carboxylate: To a suspension of sodium selenide (1.31 g, 10.4 mmol) in DMF (10.5 mL) was added a solution of 3-chloro-3-phenylprop-2-enenitrile (1.7 g, 10.4 mmol) in DMF (4 mL) at room temperature (rt) for 5 min and stirred the mixture at 60-70° C. for 2 h. Then ethyl chloroacetate (1.1 mL, 10.4 mmol) was added dropwise to the reaction mixture and again stirred at 60-70° C. for 2 h. Then, a solution of sodium methoxide (0.56 g, 10.4 mmol) in methanol (6.5 mL) was added dropwise and stifling was continued for 1 h at the same temperature. The mixture was allowed to rt and poured into cold water and stirred for 15 min. The solution was extracted with chloroform (3×100 mL) and the combined chloroform layer was washed with water, brine and dried over sodium sulfate. The solution was filtered and evaporated the solvent. The residue was chromatographed over silica gel using hexane-ethyl:acetate (90:10) as eluent to give the product as a pale yellow color solid (1.2 g, 40%), mp 88-90° C. IR (Neat) $v_{max}$ 3439, 3360, 3337, 2923, 1656, 1602, 1295, 1219, 1168, 1128, 1072, 771 cm$^{-1}$; $^1$H NMR (400 MHz, CDCl$_3$): δ 7.51-7.54 (2H, m, Ar—H), 7.34-7.40 (3H, m, Ar—H), 7.04 (1H, s, H-4), 5.60 (2H, br s, —NH$_2$), 4.28 (2H, q, J=7.0 Hz, —COOCH$_2$—), 1.35 (3H, t, J=7.0 Hz, —COOCH$_2$CH$_3$); LC-MS (positive ion mode): m/z 318, 316 (M+Na)$^+$.

Step c:

Ethyl 3-[(dimethylamino)diazenyl]-5-phenylselenophene-2-carboxylate: To a solution of ethyl 3-amino-5-phenylselenophene-2-carboxylate (0.6 g, 2.03 mmol) and conc. HCl (0.79 mL, 8.12 mmol) in water (4.7 mL) was added sodium nitrite (150 mg, 2.23 mmol) in portions for 5 min at 0° C. After stirring at 0-5° C. for 1 h, the reaction mixture was added to the solution of potassium carbonate (1.06 g, 7.7 mmol) and dimethylamine (0.82 mL, 40%, 7.3 mmol) in water (5.7 mL) at 0° C. The mixture was stirred at 0-5° C. for 2 h and poured into ice cold water. The solution was extracted with chloroform (3×100 mL) and the combined layer was washed with water, brine and dried over sodium sulfate. The solution was filtered and evaporated the solvent. The residue was chromatographed over silica gel column using hexane-EtOAc (90:10) as eluents to give the product as a dark red color solid (310 g, 44%), mp 82-84° C. $^1$H NMR (400 MHz, CDCl$_3$): δ 7.80 (1H, s, H-4), 7.58-7.60 (2H, m, Ar—H), 7.31-7.40 (3H, m, Ar—H), 4.33 (2H, q, J=7.0 Hz, —COOCH$_2$—), 3.53 (3H, s, —N—CH$_3$), 3.29 (3H, s, —N—CH$_3$), 1.37 (3H, t, J=7.0 Hz, —COOCH$_2$CH$_3$); LC-MS (positive ion mode): m/z 372, 374 (M+Na)$^+$.

Step d:

3-[(Dimethylamino)diazenyl]-5-phenylselenophene-2-carboxamide: To an ice cold (0-5° C.) solution of ammonium hydroxide (160 mL) was added a solution of ethyl 3-[(dimethylamino)diazenyl]-5-phenylselenophene-2-carboxylate (1.2 g) in THF (25 mL) for 5 min and a catalytic amount of PEG-400 was added and stirred at rt for 48 h. The solution was poured into ice cooled water and extracted with chloroform (3×100 mL). The combined organic layer was washed with water, brine and dried over sodium sulfate. The solution was filtered and evaporated the solvent. The residue was chromatographed over silica gel column using chloroform-methanol (94:6) as eluents to give the product as off-white solid, which was recrystallized from chloroform-hexane (270 mg, 31%), mp 222-224° C. IR (Neat) $v_{max}$ 3346, 2927, 2850, 1645, 1594, 1221, 1113, 1019, 875, 850 cm$^{-1}$; $^1$H NMR (400 MHz, CDCl$_3$): δ 8.25 (1H, s, —CONH$_2$), 7.87 (1H, s, H-4), 7.57-7.60 (2H, m, Ar—H), 7.30-7.40 (3H, m, Ar—H), 6.18 (1H, br s, —CONH$_2$), 3.58 (3H, s, —N—CH$_3$), 3.19 (3H, s, —N—CH$_3$); $^{13}$C NMR (100 MHz, DMSO-d$_6$): δ 165.6, 152.1, 151.9, 136.1, 131.1, 128.9, 128.5, 126.2, 118.1, 43.7, 36.6; LC-MS (positive ion mode): m/z 343, 345 (M+Na)$^+$.

Example 4

Synthesis of 3-[(dimethylamino)diazenyl]-5-(tert-butyl)selenophene-2-carboxamide (compound 4)

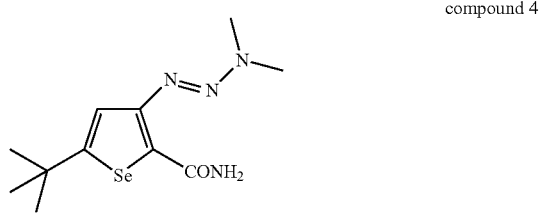

compound 4

Step a:

3-Chloro-4,4-dimethylpent-2-enenitrile: To an ice cold (0-5° C.) dimethylformamide (6.2 mL, 80 mmol) was added phosphorous oxychloride (3.75 mL, 40 mmol) dropwise with stirring for 15 min. To this cold mixture, tert-butyl methyl ketone (2.0 g, 20 mmol) was added dropwise maintaining the temperature of the reaction mixture between 45-55° C. for 10 min. The reaction mixture was slowly allowed to room temperature (rt) and stand for 30 min. To the reaction mixture, 1 mL of a total solution of hydroxylamine hydrochloride (5.56 g, 80 mmol) in dry DMF (8 mL) was added and the mixture was stirred at 70-80° C. for 5 min. Then the remaining solution of hydroxylamine hydrochloride in DMF was added thereafter at such a rate that the temperature of the reaction mixture rise above 145-155° C. After completion of the addition, the reaction mixture was allowed to rt for 30 min and diluted with cold water (200 mL). The solution was extracted with chloroform (3×100 mL) and the combined chloroform layer was washed with water, brine and dried over sodium sulfate. The solution was filtered and evaporated the solvent. The residue was chromatographed over silica gel using hexane-ethyl acetate (98:2) as eluent to give the product as a light green color oil (1.0 g, 35%). $^1$H NMR (400 MHz, CDCl$_3$): δ 5.56 (1H, s, =CH), 1.24 (9H, s, tert-butyl).

Step b:

Ethyl 3-amino-5-(tert-butyl)selenophene-2-carboxylate: To a suspension of sodium selenide (4.4 g, 34.84 mmol, prepared from 2.78 g of selenium as described above) in DMF (35 mL) was added a solution of 3-chloro-4,4-dimethylpent-2-enenitrile (5 g, 34.84 mmol) in DMF (10 mL) at rt for 5 min and stirred the mixture at 60-70° C. for 2 h. Then ethyl chloroacetate (3.71 mL, 34.84 mmol) was added dropwise to the reaction mixture and again stirred at 60-70° C. for 2 h. Then, a solution of sodium methoxide (1.88 g, 34.84 mmol) in methanol (25 mL) was added dropwise and stirring was continued for 1 h at the same temperature. The mixture was allowed to rt and poured into ice cold water and stirred for 15 min. The precipitated solid was filtered, washed with water and dried to give the product as a yellow color solid (6.2 g, 65%), mp 66-68° C. $^1$H NMR (400 MHz, CDCl$_3$): δ 6.59 (1H, s, H-4), 5.52 (2H, br s, —NH$_2$), 4.24 (2H, q, J=7.1 Hz, —COOCH$_2$CH$_3$), 1.33 (9H, s, tert-butyl), 1.31 (3H, t, J=7.1 Hz, —COOCH$_2$CH$_3$).

Step c:

Ethyl 3-[(dimethylamino)diazenyl]-5-(tert-butyl)selenophene-2-carboxylate: To a solution of ethyl-amino-5-(tert-butyl)selenophene-2-carboxylate (6 g, 21.8 mmol) and conc. HCl (8.38 mL, 87.2 mmol) in water (50 mL) was added sodium nitrite (1.65 g, 23.9 mmol) in portions for 5 min at 0° C. After stifling at 0-5° C. for 1 h, the reaction mixture was added to the solution of potassium carbonate (11.43 g, 82.8 mmol) and dimethylamine (9 mL, 40%, 78.48 mmol) in water (62 mL) at 0° C. The mixture was stirred at 0-5° C. for 2 h and poured into ice cold water. The solution was extracted with chloroform (3×200 mL) and the combined organic layer was washed with water, brine and dried over sodium sulfate. The solution was filtered and evaporated the solvent. The residue was chromatographed over silica gel column using hexane-EtOAc (90:10) as eluents to give the product, which was recrystallized from ethanol-water as a dark red color solid (2.4 g, 35%), mp 58-60° C. $^1$H NMR (400 MHz, CDCl$_3$): δ 7.31 (1H, s, H-4), 4.28 (2H, q, J=7.2 Hz, —COOCH$_2$CH$_3$), 3.48 (3H, br s, —NCH$_3$), 3.25 (3H, br s, —NCH$_3$), 1.37 (9H, s, tert-butyl), 1.34 (3H, t, J=7.2 Hz, —COOCH$_2$CH$_3$); LC-MS (positive ion mode): m/z 352, 354 (M+Na)$^+$.

Step d:

3-[(Dimethylamino)diazenyl]-5-(tert-butyl)selenophene-2-carboxamide: To an ice cold (0-5° C.) solution of ammonium hydroxide (200 mL) was added a solution of ethyl 3-[(dimethylamino)diazenyl]-5-(tert-butyl)selenophene-2-carboxylate (1.2 g) in THF (30 mL) for 5 min and a catalytic amount of PEG-400 was added and stirred at rt for 48 h. The solution was poured into ice cooled water and extracted with chloroform (3×100 mL). The combined organic layer was washed with water, brine and dried over sodium sulfate. The solution was filtered and evaporated the solvent. The residue was chromatographed over silica gel column using chloroform-methanol (94:6) as eluents to give the product as a pale brown color solid, which was recrystallized from chloroform-hexane (300 mg, 28%), mp 218-220° C. IR (Neat) $v_{max}$ 3337, 3156, 2958, 1631, 1602, 1326, 1250, 1219, 1177, 1113, 1006 cm$^{-1}$; $^1$H NMR (400 MHz, CDCl$_3$): δ 8.20 (1H, s, —CONH$_2$), 7.41 (1H, s, H-4), 6.01 (1H, br s, —CONH$_2$), 3.56 (3H, s, —NCH$_3$), 3.16 (3H, s, —NCH$_3$), 1.37 (9H, s, t-butyl); $^{13}$C NMR (100 MHz, DMSO-d$_6$): δ 168.0, 166.1, 151.1, 129.0, 116.9, 36.8, 32.4; LC-MS (positive ion mode): m/z 323, 325 (M+Na)$^+$.

Example 5

Synthesis of 3-[(dimethylamino)diazenyl]-4,5,6,7-tetrahydrobenzo[1,2-b]selenophene-2-carboxamide (compound 5)

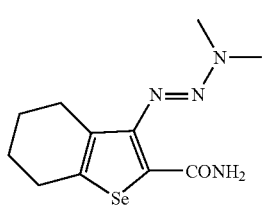

compound 5

Step a:

2-Chlorocyclohex-1-enecarbonitrile: To an ice cold (0-5° C.) solution of dry dimethylformamide (6.67 mL, 86.5 mmol) was added phosphorous oxychloride (7.66 mL, 81.6 mmol) dropwise with stirring for 15 min. To this cold mixture, cyclohexanone (5 g, 51 mmol) was added dropwise maintaining the temperature of the reaction mixture below 40° C. for 1 h. Hydroxylamine hydrochloride (20 g, 288 mmol) was added portion wise for 20 min. The addition of hydroxylamine hydrochloride was maintained at such a rate that the temperature of the reaction mixture rise above 145-155° C. After completion of the addition, the reaction mixture was allowed to room temperature (rt) for 30 min, diluted with cold water (0.5 L) and stirred for 30 min. The precipitated solid was filtered, washed with cold water and dried to give the product as a brown color solid (2.8 g, 39%), mp 38-40° C. $^1$H NMR (400 MHz, CDCl$_3$): δ 2.45-2.50 (2H, m, H-6), 2.33-2.37 (2H, m, H-3), 1.75-1.81 (2H, m, H-5), 1.66-1.72 (2H, m, H-4).

Step b:

Ethyl 3-amino-4,5,6,7-tetrahydrobenzo[2,1-d]selenophene-2-carboxylate: To a suspension of sodium selenide (4.7 g, 37.3 mmol, prepared from 3.0 g of selenium as described above) in DMF (37 mL) was added a solution of 2-chlorocyclohex-1-enecarbonitrile (5.24 g, 37.3 mmol) in DMF (18 mL) at rt for 5 min and stirred the mixture at 60° C. for 45 min. The reaction mixture was allowed to rt and added ethyl chloroacetate (3.16 mL, 37.3 mmol) dropwise for 5 min. The reaction mixture was stirred at 60° C. for 3 h. Then, a solution of sodium methoxide (2.0 g, 37.3 mmol) in methanol (37 mL) was added dropwise and stifling was continued for 2 h at the same temperature. The mixture was allowed to rt and poured into ice cold water and stirred for 15 min. The solution was extracted with chloroform (3×200 mL) and the combined chloroform layer was washed with water, brine and dried over sodium sulfate. The solution was filtered and evaporated the solvent. The residue was chromatographed over silica gel column using hexane-EtOAc (90:10) as eluents to give the product as a yellow color oil of a mixture of ethyl and methyl ester (2.4 g, 25%). $^1$H NMR (400 MHz, CDCl$_3$): δ 5.54 (2H, s, —NH$_2$), 4.24 (2H, q, J=7.1 Hz, —COOCH$_2$CH$_3$), 2.74-2.75 (2H, m, H-7), 2.27-2.28 (2H, m, H-4), 1.81-1.84 (4H, m, H-5,6), 1.31 (3H, t, J=7.1 Hz, —COOCH$_2$CH$_3$); LC-MS (positive ion mode): m/z 294, 296 (M+Na)$^+$.

Step c:

Methyl 3-[(dimethylamino)diazenyl]-4,5,6,7-tetrahydrobenzo[2,1-d]selenophene-2-carboxylate: To a solution of ethyl and methyl esters of 3-amino-4,5,6,7-tetrahydrobenzo[2,1-d]selenophene-2-carboxylate (400 mg, 1.54 mmol), conc. HCl (0.6 mL, 6.17 mmol) in water (3.5 mL) and acetone (3 mL) was added sodium nitrite (120 mg, 1.69 mmol) in portions for 5 min at 0° C. After stirring at 0-5° C. for 1 h, the reaction mixture was added to the solution of potassium carbonate (800 mg, 5.85 mmol) and dimethylamine (0.62 mL, 40%, 5.54 mmol) in water (4.3 mL) at 0° C. The mixture was stirred at 0-5° C. for 1 h and poured into ice cold water. The solution was extracted with chloroform (3×200 mL) and the combined organic layer was washed with water, brine and dried over sodium sulfate. The solution was filtered and evaporated the solvent. The residue was chromatographed over silica gel column using hexane-EtOAc (95:5) as eluents to give the product as brown oil (200 mg, 50%). It is a mixture of ethyl and methyl mixtures. $^1$H NMR (400 MHz, CDCl$_3$): δ 3.74 (3H, s, —COOCH$_3$), 3.34 (6H, br s, —N(CH$_3$)$_2$), 2.79 (2H, br s, H-4), 2.41 (2H, br s, H-7), 1.74-1.82 (4H, m, H-5,6); LC-MS (positive ion mode): m/z 336, 338 (M+Na)±.

Step d:

3-[(Dimethylamino)diazenyl]-4,5,6,7-tetrahydrobenzo[1,2-b]selenophene-2-carboxamide: To an ice cold (0-5° C.) solution of ammonium hydroxide (60 mL) was added a mixture of ethyl and methyl esters of 3-[(dimethylamino)diazenyl]-4,5,6,7-tetrahydrobenzo[2,1-d]selenophene-2-carboxylate (600 mg) in THF (6 mL) for 5 min. A catalytic amount of PEG-400 was added and stirred at rt for 66 h. The solution was poured into ice cooled water and extracted with chloroform (3×150 mL). The combined organic layer was washed with water, brine and dried over sodium sulfate. The solution was filtered and evaporated the solvent. The residue was chromatographed over silica gel column using chloroform-methanol (98:2) as eluents to give the product as a pale brown color solid (100 mg, 18%), which was recrystallized from chloroform-hexane (70 mg), mp 198-202° C. IR (Neat) ν$_{max}$ 3347, 3163, 2932, 2860, 1631, 1342, 1313, 1220, 1103, 1020, 878 cm$^{-1}$; $^1$H NMR (400 MHz, CDCl$_3$): δ 8.21 (1H, s, —CONH$_2$), 6.07 (1H, s, —CONH$_2$), 3.51 (3H, br s, —NCH$_3$), 3.14 (3H, br s, —NCH$_3$), 2.80-2.82 (2H, m, H-4), 2.64-2.65 (2H, m, H-7), 1.72-1.80 (4H, m, H-5,6); $^{13}$C NMR (100 MHz, CDCl$_3$): δ 165.9, 149.5, 145.9, 132.6, 129.5, 29.0, 28.6, 23.1, 22.7; LC-MS (positive ion mode): m/z 321, 323 (M+Na)$^+$.

Example 6

Synthesis of 3-[(dimethylamino)diazenyl]selenopheno[2,3-b]pyridine-2-carboxamide (compound 6)

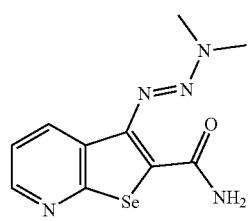

compound 6

Step a:

Ethyl 3-aminoselenopheno[2,3-b]pyridine-2-carboxylate: To a suspension of sodium selenide (0.9 g, 7.2 mmol, prepared from 0.75 g of selenium as described above) in DMF (7 mL) was added a solution of 2-chloropyridine-3-carbonitrile (1 g, 7.2 mmol) in DMF (3 mL) at rt for 5 min and stirred the mixture at 60-70° C. for 2 h. Then ethyl chloroacetate (0.78 mL, 7.22 mmol) was added dropwise to the reaction mixture and again stirred at 60-70° C. for 2 h. Then, a solution of sodium methoxide (0.39 g, 7.2 mmol) in methanol (7 mL) was added dropwise and stirring was continued for 1 h at the same temperature. The mixture was allowed to room temperature (rt) and poured into cold water and stirred for 15 min. The precipitated solid was filtered, washed with water and dried to give the product as a yellow color solid (1.5 g, 77%), mp 194-196° C. $^1$H NMR (400 MHz, CDCl$_3$): δ 8.65 (1H, dd, J=4.6, 1.4 Hz, H-6), 7.86 (1H, dd, J=8.2, 1.4 Hz, H-4), 7.33 (1H, dd, J=8.2, 4.6 Hz, H-5), 6.04 (2H, br s, —NH$_2$), 4.34 (2H, q, J=7.1 Hz, —COOCH$_2$CH$_3$), 1.38 (3H, t, J=7.1 Hz, —COOCH$_2$CH$_3$); LC-MS (positive ion mode): m/z 269, 271 (M+H)$^+$.

Step b:

Ethyl 3-[(dimethylamino)diazenyl]selenopheno[2,3-b]pyridine-2-carboxylate: A suspension of ethyl-aminoselenopheno[2,3-b]pyridine-2-carboxylate (1 g, 3.7 mmol) and aqueous fluoroboric acid (5.8 mL, 29.6 mmol, 45%) in water (40 mL) was heated to dissolve the compound. The mixture was again cooled to 0° C. and added sodium nitrite (300 mg, 4.4 mmol) in portions for 5 min at 0° C. After stifling at 0-5° C. for 30 min, the reaction mixture was added to the solution of potassium carbonate (3.8 g, 28 mmol) and dimethylamine (3 mL, 40%, 26.8 mmol) in water (60 mL) at 0° C. The mixture was stirred at 0-5° C. for 1 h and poured into ice cold water. The solution was extracted with chloroform (3×200 mL) and the combined organic layer was washed with water, brine and dried over sodium sulfate. The solution was filtered and evaporated the solvent. The residue was chromatographed over silica gel column using hexane-EtOAc (90:10) as eluents to give the product as orange color oil (170 g, 14%). $^1$H NMR (400 MHz, CDCl$_3$): δ 8.61 (1H, d, J=3.2 Hz, H-4), 8.30 (1H, d, J=8.0, H-6), 7.31 (1H, dd, J=8.2, 4.6 Hz, H-5), 4.33 (2H, q, J=7.0 Hz, —COOCH$_2$CH$_3$), 3.58 (3H, s, —NCH$_3$), 3.33 (3H, s, —NCH$_3$), 1.37 (3H, t, J=7.0 Hz, —COOCH$_2$CH$_3$); LC-MS (positive ion mode): m/z 325, 327 (M+H)$^+$.

Step c:

3-[(Dimethylamino)diazenyl]selenopheno[2,3-b]pyridine-2-carboxamide: To an ice cold (0-5° C.) solution of ammonium hydroxide (15 mL) was added a solution of ethyl 3-[(dimethylamino)diazenyl]selenopheno[2,3-b]pyridine-2-carboxylate (150 mg) in THF (5 mL) for 5 min and stirred at rt for 16 h. The solution was poured into ice cooled water and extracted with ethyl acetate (3×100 mL). The combined EtOAc layer was washed with water, brine and dried over sodium sulfate. The solution was filtered and evaporated the solvent. The residue was chromatographed over silica gel column using chloroform-methanol (95:5) as eluents to give the product as a light green color solid, which was recrystallized from chloroform-methanol-hexane (25 mg, 20%), mp 230-232° C. IR (Neat) ν$_{max}$ 3327, 3152, 2913, 1701, 1634, 1360, 1330, 1104, 1058, 1016, 878, 802 cm$^{-1}$; $^1$H NMR (400 MHz, DMSO-d$_6$): δ 8.80 (1H, d, J=8.4 Hz, H-6), 8.59 (1H, d, J=3.2 Hz, H-6), 8.18 (1H, s, —CONH$_2$), 7.99 (1H, s, —CONH$_2$), 7.46 (1H, dd, J=8.2, 4.6 Hz, H-5), 3.66 (3H, s, —NCH$_3$), 3.26 (3H, s, —NCH$_3$); $^{13}$C NMR (100 MHz, DMSO-d$_6$): δ 164.4, 161.1, 148.3, 142.5, 136.2, 131.5, 130.4, 120.6, 43.6, 36.5; LC-MS (positive ion mode): m/z 318, 320 (M+Na)$^+$.

Example 7

Synthesis of 3-[(dimethylamino)diazenyl]-5-phenylselenophene-2-carboxylic acid (compound 7)

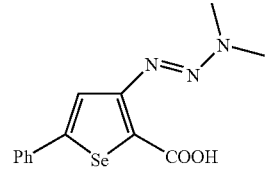

compound 7

To a solution of ethyl 3-[(dimethylamino)diazenyl]-5-phenylselenophene-2-carboxylate (200 mg, 0.56 mmol) prepared as described in Example 3 step c) in methanol (5 mL) was added a solution of sodium hydroxide (113 mg, 2.84 mmol) in water (3 mL) and stirred at rt for 16 h. The mixture was diluted with ice cold water and acidified with dil. HCl. The mixture was stirred for 30 min and the precipitated solid was filtered, washed with water and dried. The product was recrystallized from hexane-chloroform to give the product as a brown color solid (100 mg, 54%), mp 212-214° C. IR (neat) ν$_{max}$ 3566, 2924, 1700, 1253, 1180, 1113, 1070, 1011, 838, 766 cm$^-$; $^1$H NMR (400 MHz, CDCl$_3$): δ 12.27 (1H, s, —COOH), 7.79 (1H, s, H-4), 7.55-7.57 (2H, m, Ar—H), 7.34-7.39 (3H, m, Ar—H), 3.65 (3H, s, —N—CH$_3$), 3.25 (3H, s, —N—CH$_3$); $^{13}$C NMR (100 MHz, CDCl$_3$): δ 163.9, 155.2, 154.6, 135.5, 129.2, 129.1, 126.3, 124.9, 116.6, 44.4, 37.1; LC-MS (positive ion mode): m/z 346, 344 (M+Na)$^+$.

Example 8

Synthesis of 3-[(dimethylamino)diazenyl]-5-(tert-butyl)selenophene-2-carboxylic acid (compound 8)

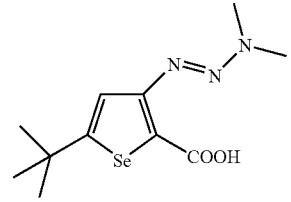

compound 8

To a solution of ethyl 3-[(dimethylamino)diazenyl]-5-(tert-butyl)selenophene-2-carboxylate (400 mg, 1.2 mmol) prepared as described in Example 4 step c) in methanol (10 mL) was added a solution of sodium hydroxide (240 mg, 6.04 mmol) in water (5 mL) and stirred at room temperature (rt) for 16 h. The mixture was diluted with ice cold water and acidified with dil. HCl. The mixture was stirred for 30 min and the precipitated solid was filtered, washed with water and dried. The product was recrystallized from hexane-chloroform to give the product as a pale brown color solid (160 mg, 45%), mp 120-122° C. IR (neat) ν$_{max}$ 2960, 2927, 1713, 1248, 1180, 1110, 1069, 1010, 844, 767 cm$^{-1}$; $^1$H NMR (400 MHz, CDCl$_3$): δ 12.23 (1H, s, —COOH), 7.38 (1H, s, H-4), 3.63

(3H, s, —NCH₃), 3.23 (3H, s, —NCH₃), 1.39 (9H, s, 3×—CH₃); $^{13}$C NMR (100 MHz, CDCl₃): δ 171.7, 164.1, 153.7, 123.2, 115.6, 44.2, 37.2, 36.9, 32.4; LC-MS (positive ion mode): m/z 324, 326 (M+Na)⁺.

Example 9

Synthesis of 3-[(dimethylamino)diazenyl]-4,5,6,7-tetrahydrobenzo[1,2-b]selenophene-2-carboxylic acid (compound 9)

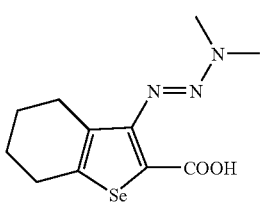

compound 9

To a solution of ethyl and methyl esters of 3-[(dimethylamino)diazenyl]-4,5,6,7-tetrahydrobenzo[2,1-d]selenophene-2-carboxylate (1.0 g, 3.1 mmol) prepared as described in Example 5 step c) in methanol (10 mL) was added a solution of sodium hydroxide (500 mg, 12.6 mmol) in water (2 mL) and stirred at rt for 5 h. The mixture was diluted with ice cold water and extracted with chloroform (2×50 mL) to remove impurities. The aqueous layer was acidified with dil. HCl and stirred for 30 min. The solution was extracted with chloroform (3×100 mL) and the combined organic layer was washed with water, brine and dried over sodium sulfate. The solution was filtered and evaporated the solvent (550 mg, 57%). The crude product was recrystallized from chloroform-diethyl ether to give the product as a dark brown color solid (330 mg), mp 100-102° C. IR (Neat) $v_{max}$ 3429, 2927, 2855, 1701, 1350, 1110, 1050, 1023, 880 cm⁻¹; $^{1}$H NMR (400 MHz, CDCl₃): δ 12.71 (1H, br s, —COOH), 3.59 (3H, s, —NCH₃), 3.20 (3H, s, —NCH₃), 2.83 (2H, t, J=5.4 Hz, H-4), 2.73 (2H, t, J=5.6 Hz, H-7), 1.75-1.81 (4H, m, H-5,6); $^{13}$C NMR (100 MHz, CDCl₃): δ 164.5, 151.3, 148.9, 131.5, 124.0, 44.1, 36.5, 28.8 (2C), 22.8, 22.4; LC-MS (positive ion mode): m/z 300, 302 (M+H)⁺.

Example 10

Synthesis of 3-[(dimethylamino)diazenyl]selenopheno[2,3-b]pyridine-2-carboxylic acid (compound 10)

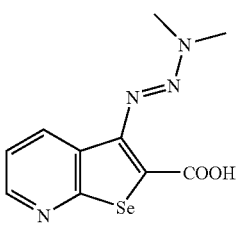

compound 10

To a solution of ethyl 3-[(dimethylamino)diazenyl]selenopheno[2,3-b]pyridine-2-carboxylate (170 mg, 0.52 mmol), prepared as described in Example 6 step b) in methanol (10 mL) was added a solution of sodium hydroxide (83 mg, 2.08 mmol) in water (2 mL) and stirred at room temperature (rt) for 2 h. The mixture was diluted with ice cold water and acidified with dil. HCl. The mixture was stirred for 30 min and extracted with ethyl acetate (3×100 mL). The combined organic layer was washed with water, brine and dried over sodium sulfate. The solution was filtered and evaporated the solvent. The residue was chromatographed over silica gel column using chloroform-methanol (95:5) as eluents to give the product, which was recrystallized from chloroform-methanol-hexane as a light brown color solid (30 mg, 20%), mp 172-174° C. IR (KBr) $v_{max}$ 3427, 3025, 2919, 1707, 1265, 1218, 1013, 863 cm⁻¹; $^{1}$H NMR (400 MHz, DMSO-d₆): δ 13.09 (1H, br s, —COOH), 8.65-8.69 (2H, m, H-4,6), 7.53 (1H, dd, J=8.2, 4.6 Hz, H-5), 3.67 (3H, s, —NCH₃), 3.29 (3H, s, —NCH₃); LC-MS (positive ion mode): m/z 319, 321 (M+Na)⁺.

Example 11

Synthesis of 3-[(dimethylamino)diazenyl]-5-(tert-butyl)selenophene-2-carbonitrile (compound 11)

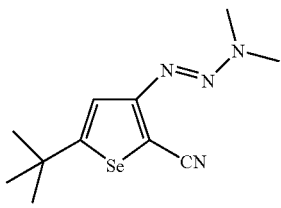

compound 11

To a solution of 3-amino-5-(tert-butyl)selenophene-2-carbonitrile (1 g, 4.3 mmol), prepared as described in Example 13 step a), fluoroboric acid (2.7 mL, 45% aqueous, 17.5 mmol), water (10 mL) and acetone (25 mL) was added sodium nitrite (0.33 g, 4.8 mmol) in portions for 5 min at 0° C. After stifling at 0-5° C. for 2.5 h, the reaction mixture was added to the solution of potassium carbonate (2.3 g, 16.64 mmol) and dimethylamine (3.5 mL, 40%, 15.76 mmol) in water (20 mL) at 0° C. The mixture was stirred at 0-5° C. for 2 h and poured into ice cold water. The solution was extracted with chloroform (3×200 mL) and the combined organic layer was washed with water, brine and dried over sodium sulfate. The solution was filtered and evaporated the solvent. The residue was chromatographed over silica gel column using hexane-EtOAc (95:5) as eluents to give the product, which was recrystallized from hexane-chloroform as a red color solid (15 mg, 12%), mp 58-60° C. IR (neat) $v_{max}$ 3437, 2200, 1633, 1339, 1219, 1178, 1094 cm⁻¹; $^{1}$H NMR (400 MHz, CDCl₃): δ 7.26 (1H, s, H-4), 3.52 (3H, s, —NCH₃), 3.22 (3H, s, —NCH₃), 1.38 (9H, s, tert-butyl); $^{13}$C NMR (100 MHz, CDCl$_3$): δ 171.0, 161.5, 117.3, 116.4, 95.2, 43.3, 37.3, 36.2, 32.4; LC-MS (positive ion mode): m/z 283, 285 (M+H)$^+$.

Example 12

Synthesis of 3-methyl-6-phenylselenopheno[3,2-d]1,2,3-triazin-4-one (compound 12)

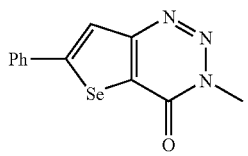
compound 12

Step a:

3-Amino-5-phenylselenophene-2-carbonitrile: To a suspension of sodium selenide (4.62 g, 36.7 mmol, prepared from 2.9 g of selenium as described above) in DMF (37 mL) was added a solution of 3-chloro-3-phenylprop-2-enenitrile (6.0 g, 36.7 mmol) in DMF (14 mL) at rt for 5 min and stirred the mixture at 60-70° C. for 2 h. Then chloroacetonitrile (2.32 mL, 36.7 mmol) was added dropwise to the reaction mixture and again stirred at 60-70° C. for 2 h. Then, a solution of sodium methoxide (2.0 g, 36.7 mmol) in dry methanol (23 mL) was added dropwise and stirring was continued for 1 h at the same temperature. The mixture was allowed to room temperature (rt) and poured into cold water and stirred for 15 min. The precipitated solid was filtered and washed with water. The solid was recrystallized from chloroform-hexane to give the product as a brown color solid (4.8 g, 53%), mp 162-164° C. (decomp). $^1$H NMR (400 MHz, CDCl$_3$): δ 7.46-7.49 (2H, m, Ar—H), 7.37-7.39 (3H, m, Ar—H), 7.01 (1H, s, H-4), 4.55 (2H, br s, —NH$_2$).

Step b:

3-Amino-5-phenylselenophene-2-carboxamide: To a suspension of 3-amino-5-phenylselenophene-2-carbonitrile (4.0 g) in aqueous sodium hydroxide solution (120 mL, 10%) was added ethanol (50 mL) and the mixture refluxed for 45 min. The mixture was allowed to rt and the crystals separated were filtered off, washed with cold water and dried to give the product as golden yellow color solid (2.8 g, 67%), mp 184-186° C. $^1$H NMR (400 MHz, CDCl$_3$): δ 7.50-7.53 (2H, m, Ar—H), 7.36-7.38 (3H, m, Ar—H), 7.04 (1H, s, H-4), 5.84 (2H, br s, —CONH$_2$), 5.12 (2H, br s, —NH$_2$).

Step c:

6-Phenyl-3H-selenopheno[3,2-c]1,2,3-triazin-4-one: To an ice cold solution (0° C.) of 3-amino-5-phenylselenophene-2-carboxamide (0.27 g, 1.01 mmol) in concentrated sulfuric acid (7 mL) was added a cold (0° C.) solution of sodium nitrite (77 mg, 1.11 mmol) in concentrated sulfuric acid (2.5 mL) for 10 min (while adding, the temperature should keep between −5-0° C.). After addition, the mixture was stirred at 0° C. for 1 h and at rt for 1 h. The reaction mixture was cooled and poured into crushed ice slowly with stirring for 15 min and stirred at the same temperature for 15 min. The solution was extracted with ethyl acetate (3×50 mL) and the combined layer was washed with water, brine and dried over sodium sulfate. The solution was filtered and evaporated the solvent. The residue was recrystallized from chloroform-methanol to give the product as a white color solid (150 mg, 53%), mp 182-184° C. (decomp). $^1$H NMR (400 MHz, DMSO-d$_6$): δ15.19 (1H, s, —NH), 8.44 (1H, s, H-7), 7.89-7.91 (2H, m, Ar—H), 7.52-7.54 (3H, m, Ar—H); LC-MS (positive ion mode): m/z 276, 278 (M+H)$^+$.

Step d:

3-Methyl-6-phenylselenopheno[3,2-d]1,2,3-triazin-4-one: To a solution of 6-phenyl-3H-selenopheno[3,2-c]1,2,3-triazin-4-one (0.6 g, 2.16 mmol) in acetone (25 mL) was added sequentially potassium carbonate (0.59 g, 4.33 mmol), iodomethane (0.16 mL, 2.6 mmol) and potassium iodide (catalytic) at rt and the mixture was stirred at rt for 16 h. The solution was filtered and the solids were washed with acetone. Acetone was evaporated under reduced pressure, diluted with ice cold water and stirred for 10 min. The solution was extracted with chloroform (4×75 mL) and the combined layer was washed with water, brine and dried over sodium sulfate. The solution was filtered and evaporated the solvent. The residue was chromatographed over silica gel column using chloroform-methanol (95:05) as eluents to give the product as an off-white solid (400 mg, 64%), which was recrystallized from chloroform-methanol (180 mg), mp 232-234° C. IR (neat) ν$_{max}$ 2923, 2857, 1672, 1220, 1019, 972 cm$^{-1}$; $^1$H NMR (400 MHz, CDCl$_3$): δ 7.98 (1H, s, H-7), 7.63-7.66 (2H, m, Ar—H), 7.45-7.50 (3H, m, Ar—H), 4.06 (3H, s, —NCH$_3$); $^{13}$C NMR (100 MHz, CDCl$_3$): δ 159.4, 158.0, 154.6, 134.3, 130.1, 129.7, 129.4, 126.9, 122.2, 37.5; LC-MS (positive ion mode): m/z 312, 314 (M+Na)$^+$.

Example 13

Synthesis of 6-(tert-butyl)-3-methylselenopheno[3,2-d]1,2,3-triazin-4-one (compound 13)

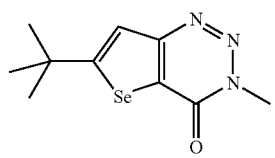
compound 13

Step a:

3-Amino-5-(tert-butyl)selenophene-2-carbonitrile: To a suspension of sodium selenide (4.39 g, 34.84 mmol, prepared from 2.78 g of selenium as described above) in DMF (35 mL) was added a solution of 3-chloro-4,4-dimethylpent-2-enenitrile (5.0 g, 34.84 mmol) in DMF (13 mL) at rt for 5 min and stirred the mixture at 60-70° C. for 2 h. Then chloroacetonitrile (2.2 mL, 34.84 mmol) was added dropwise to the reaction mixture and again stirred at 60-70° C. for 2 h. Then, a solution of sodium methoxide (1.88 g, 34.84 mmol) in dry methanol (22 mL) was added dropwise and stirring was continued for 1 h at the same temperature. The mixture was allowed to room temperature (rt) and poured into cold water and stirred for 30 min. The precipitated solid was filtered and washed with water. The solid was recrystallized from chloroform-hexane to give the product as a brown color solid (5.2 g, 65%), mp 110-112° C. $^1$H NMR (400 MHz, CDCl$_3$): δ 6.59 (1H, s, H-4), 4.46 (2H, br s, —NH$_2$), 1.33 (9H, s, tert-butyl); LC-MS (negative ion mode): m/z 225, 227 (M−H)$^-$.

Step b:

3-Amino-5-(tert-butyl)selenophene-2-carboxamide: To a suspension of 3-amino-5-(tert-butyl)selenophene-2-carbonitrile (5.0 g) in aqueous sodium hydroxide solution (80 mL, 10%) was added ethanol (50 mL) and the mixture refluxed for 1 h. Ethanol was distilled off under vacuum (appr. 25 mL) and the mixture was allowed to cool to 5-10° C. The separated crystals were filtered off, washed with cold water and dried to give the product as a off-white color solid (4.5 g, 84%), mp 160-162° C. $^1$H NMR (400 MHz, CDCl$_3$): δ 6.58 (1H, s, H-4), 5.75 (2H, br s, —CONH$_2$), 5.13 (2H, br s, —NH$_2$), 1.34 (9H, s, tert-butyl).

Step c:

6-(tert-Butyl)-3H-selenopheno[3,2-d]1,2,3-triazin-4-one: To an ice cold solution (0° C.) of 3-amino-5-(tert-butyl)selenophene-2-carboxamide (3.0 g, 12.2 mmol) in concentrated sulfuric acid (50 mL) was added a cold (0° C.) solution of sodium nitrite (0.92 g, 13.4 mmol) in concentrated sulfuric acid (10 mL) for 10 min (while adding, the temperature should keep between –5-0° C.). After addition, the mixture was stirred at 0° C. for 1 h and at rt for 1 h. The reaction mixture was cooled and poured into crushed ice slowly with stirring for 15 min and stirred at the same temperature for 15 min. The solid was filtered, washed with ice cold water and dried to give the product as a off-white color solid (2.4 g, 77%), mp 158-160° C. $^1$H NMR (400 MHz, CDCl$_3$): δ 7.67 (1H, s, H-7), 1.50 (9H, s, tert-butyl); LC-MS (negative ion mode): m/z 254, 256 (M–H)—.

Step d:

6-(tert-Butyl)-3-methylselenopheno[3,2-d]1,2,3-triazin-4-one: To a solution of 6-(tert-butyl)-3H-selenopheno[3,2-d]1,2,3-triazin-4-one (2.0 g, 7.78 mmol) in acetone (70 mL) was added sequentially potassium carbonate (2.14 g, 15.56 mmol), iodomethane (0.58 mL, 9.3 mmol) and potassium iodide (catalytic) at rt and the mixture was stirred at rt for 16 h. The solution was filtered and the solids were washed with acetone. Acetone was evaporated under reduced pressure and the residue was chromatographed over silica gel column using chloroform-methanol (95:05) as eluents to give the product as a off-white color solid (1.0 g, 47%), which was recrystallized from chloroform-methanol (700 mg, 34%), mp 98-100° C. IR (neat) ν$_{max}$ 2961, 1679, 1242, 1220, 1001, 969 cm$^{-1}$; $^1$H NMR (400 MHz, CDCl$_3$): δ 7.58 (1H, s, H-7), 4.04 (3H, s, —NCH$_3$), 1.48 (9H, s, tert-butyl); $^{13}$C NMR (100 MHz, CDCl$_3$): δ 176.0, 157.5, 154.7, 128.8, 121.5, 37.5, 37.3, 32.5; LC-MS (positive ion mode): m/z 292, 294 (M+Na)$^+$.

Example 14

Synthesis of 3-methyl-6,7,8,9-tetrahydrobenzo[1,2-b]1,2,3-triazino[4,5-d]selenophen-4-one (compound 14)

compound 14

Step a:

3-Amino-4,5,6,7-tetrahydrobenzo[1,2-b]selenophene-2-carbonitrile: To a suspension of sodium selenide (2.35 g, 18.65 mmol, prepared from 1.5 g of selenium as described above) in DMF (18 mL) was added a solution of 2-chlorocyclohex-1-enecarbonitrile (2.63 g, 18.65 mmol) in DMF (9 mL) at rt for 5 min and stirred the mixture at 60° C. for 45 min. Then chloroacetonitrile (1.18 mL, 18.65 mmol) was added dropwise to the reaction mixture and again stirred at 60° C. for 3 h. Then, a solution of sodium methoxide (1.0 g, 18.65 mmol) in dry methanol (18 mL) was added dropwise and stirring was continued for 2 h at the same temperature. The mixture was allowed to room temperature (rt) and poured into cold water and stirred for 30 min. The precipitated solid was filtered and washed with water to give the product as a dark brown color solid (2.4 g, 57%), mp 86-88° C. $^1$H NMR (400 MHz, CDCl$_3$): δ 4.39 (2H, br s, —NH$_2$), 2.73-2.74 (2H, m, H-7), 2.28-2.29 (2H, m, H-4), 1.83-1.84 (4H, m, H-5,6).

Step b:

3-Amino-4,5,6,7-tetrahydrobenzo[1,2-b]selenophene-2-carboxamide: To a suspension of 3-amino-4,5,6,7-tetrahydrobenzo[1,2-b]selenophene-2-carbonitrile (2.4 g) in ethanol (50 mL) was added aqueous sodium hydroxide solution (50 mL, 10%) at rt and the mixture was refluxed for 1 h. The cooled reaction mixture was poured into ice cooled water and stirred for 15 min. The precipitated solid filtered, washed with cold water and dried to give the product as a pale brown color solid (1.4 g, 54%), mp 152-154° C. $^1$H NMR (400 MHz, DMSO-d$_6$): δ 6.58 (1H, s, —CONH$_2$), 6.45 (1H, s, —CONH$_2$), 2.66 (2H, s, H-7), 2.24 (2H, s, H-4), 1.73 (4H, s, H-5,6); LC-MS (positive ion mode): m/z 265, 267 (M+Na)$^+$.

Step c:

6,7,8,9-Tetrahydro-3H-benzo[1,2-b]1,2,3-triazino[4,5-d]selenophen-4-one: To an ice cold (0° C.) solution of 3-amino-4,5,6,7-tetrahydrobenzo[1,2-b]selenophene-2-carboxamide (1.4 g, 5.73 mmol) in concentrated sulfuric acid (10 mL) was added a cold (0° C.) solution of sodium nitrite (0.43 g, 6.31 mmol) in concentrated sulfuric acid (3 mL) for 10 min (while adding, the temperature should keep between –5-0° C.). After addition, the mixture was stirred at 0° C. for 2 h. The reaction mixture was poured into crushed ice slowly with stirring for 15 min and stirred at the same temperature for 15 min. The solution was extracted with ethyl acetate (3×100 mL) and the combined EtOAc layer was washed with water, brine and dried over sodium sulfate. The solution was filtered and evaporated the solvent to give the product as a pale brown color solid (450 mg, 31%), mp 150-152° C. $^1$H NMR (400 MHz, DMSO-d$_6$): δ 15.13 (1H, br s, —NH), 3.01-3.04 (2H, m, H-9), 2.90-2.92 (2H, m, H-6), 1.89-1.96 (4H, m, H-7,8); LC-MS (negative ion mode): m/z 252, 254 (M–H)$^-$.

Step d:

3-Methyl-6,7,8,9-tetrahydrobenzo[1,2-b]1,2,3-triazino[4,5-d]selenophen-4-one: To a solution of 6,7,8,9-tetrahydro-3H-benzo[1,2-b]1,2,3-triazino[4,5-d]selenophen-4-one (450 mg, 1.76 mmol) in acetone (50 mL) was added sequentially potassium carbonate (480 mg, 3.52 mmol), iodomethane (0.13 mL, 2.11 mmol) and a catalytic amount of PEG-400 was added and stirred at rt and the mixture was stirred at rt for 16 h. The solution was filtered and the solids were washed with acetone. Acetone was evaporated under reduced pressure and the residue was chromatographed over silica gel column using hexane-ethyl acetate (90:10) as eluents to give the product as a pale yellow color solid (340 mg, 72%), which was recrystallized from chloroform-hexane (170 mg), mp 110-112° C. IR (neat) ν$_{max}$ 3438, 1668, 1220, 1018 cm$^{-1}$; $^1$H NMR (400 MHz, CDCl$_3$): δ 4.05 (3H, s, —NCH$_3$), 2.94-2.96 (4H, m, H-6,9), 1.91-1.97 (4H, m, H-7,8); $^{13}$C NMR (100

MHz, CDCl$_3$): δ 156.1, 155.1, 152.5, 133.9, 128.5, 37.4, 28.4, 24.8, 23.6, 21.4; LC-MS (positive ion mode): m/z 268, 270 (M+H)$^+$.

Example 15

Synthesis of 3-methyl-1,2,3-triazino[4',5'-5,4]selenopheno[2,3-b]pyridine-4-one (compound 15)

compound 15

Step a:

3-Aminoselenopheno[2,3-b]pyridine-2-carbonitrile: To a suspension of sodium selenide (0.9 g, 7.2 mmol, prepared from 0.75 g of selenium as described above) in DMF (7 mL) was added a solution of 2-chloropyridine-3-carbonitrile (1 g, 7.2 mmol) in DMF (3 mL) at rt for 5 min and stirred the mixture at 60-70° C. for 2 h. Then chloroacetonitrile (0.46 mL, 7.22 mmol) was added dropwise to the reaction mixture and again stirred at 60-70° C. for 2 h. Then, a solution of sodium methoxide (0.39 g, 7.2 mmol) in methanol (7 mL) was added dropwise and stifling was continued for 1 h at the same temperature. The mixture was allowed to room temperature (rt) and poured into cold water and stirred for 15 min. The precipitated solid was filtered, washed with water and dried to give the product as a yellow color solid (1.3 g, 81%), mp 208-210° C. 1H NMR (400 MHz, DMSO-d$_6$): δ 8.68 (1H, d, J=4.4 Hz, H-6), 8.47 (1H, d, J=8.4 Hz, H-4), 7.55 (1H, dd, J=8.0, 4.8 Hz, H-5), 7.24 (2H, s, —NH$_2$).

Step b:

3-Aminoselenopheno[2,3-b]pyridine-2-carboxamide: To a suspension of 3-aminoselenopheno[2,3-b]pyridine-2-carbonitrile (1.0 g) in aqueous sodium hydroxide solution (20 mL, 10%) was added ethanol (20 mL) and the mixture refluxed for 45 min. Ethanol was distilled off under vacuum (appr. 25 mL) and the mixture was allowed to cool to 5-10° C. The separated crystals and the solution was poured into ice cooled water and stirred for 15 min. The solid was filtered off, washed with cold water and dried to give the product as a pale yellow color solid (0.53 g, 50%), mp 256-260° C. $^1$H NMR (400 MHz, DMSO-d$_6$): δ 8.60 (1H, d, J=3.6 Hz, H-6), 8.37 (1H, d, J=7.6 Hz, H-4), 7.47 (1H, dd, J=8.0, 4.8 Hz, H-5), 7.32 (2H, s, —CONH$_2$), 7.09 (2H, s, —NH$_2$); LC-MS (negative ion mode): m/z 238, 241 (M−H)$^-$.

Step c:

3H-1,2,3-Triazino[4',5'-5,4]selenopheno[2,3-b]pyridin-4-one: To an ice cold (0° C.) solution of 3-aminoselenopheno[2,3-b]pyridine-2-carboxamide (0.5 g, 2.07 mmol) in concentrated sulfuric acid (5 mL) was added a cold (0° C.) solution of sodium nitrite (157 mg, 2.28 mmol) in concentrated sulfuric acid (2 mL) for 10 min (while adding, the temperature should keep between −5-0° C.). After addition, the mixture was stirred at 0° C. for 2 h. The reaction mixture was poured into crushed ice slowly with stirring for 15 min and stirred at the same temperature for 15 min. The solution was extracted with ethyl acetate (3×100 mL) and the combined organic layer was washed with water, brine and dried over sodium sulfate. The solution was filtered and evaporated the solvent to give the product as a reddish brown color solid (350 mg, 67%), mp 184-186° C. (decomposed). $^1$H NMR (400 MHz, DMSO-d$_6$): δ 15.61 (1H, s, —NH), 8.90 (1H, dd, J=4.6, 1.8 Hz, H-9), 8.83 (1H, dd, J=8.0, 1.6 Hz, H-7), 7.81 (1H, dd, J=8.0, 4.8 Hz, H-8); LC-MS (negative ion mode): m/z 249, 251 (M−H)$^-$.

Step d:

3-Methyl-1,2,3-triazino[4',5'-5,4]selenopheno[2,3-b]pyridine-4-one: To a solution of 3H-1,2,3-triazino[4',5'-5,4]selenopheno[2,3-b]pyridin-4-one (300 mg, 1.19 mmol) in acetone (40 mL) was added sequentially potassium carbonate (328 mg, 2.38 mmol), iodomethane (0.09 mL, 1.42 mmol) and a catalytic amount of PEG-400 was added and stirred at rt and the mixture was stirred at rt for 16 h. The solution was filtered and the solids were washed with acetone. Acetone was evaporated under reduced pressure and the residue was chromatographed over silica gel column using hexane-ethyl acetate (80:20) as eluents to give the product, which was recrystallized from chloroform-hexane as a off-white color solid (216 mg, 68%), mp 202-204° C. IR (neat) ν$_{max}$ 3406, 1665, 1241, 1105, 1054, 965, 852, 813, 757 cm$^{-1}$; $^1$H NMR (400 MHz, CDCl$_3$): δ 8.80 (1H, dd, J=4.6, 1.8 Hz, H-9), 8.76 (1H, dd, J=8.0, 2.0 Hz, H-7), 7.60 (1H, dd, J=8.0, 4.8 Hz, H-8), 4.15 (3H, s, —NCH$_3$); $^{13}$C NMR (100 MHz, CDCl$_3$): δ 165.4, 154.9, 151.3, 150.2, 133.5, 131.1, 130.1, 121.4, 38.0; LC-MS (positive ion mode): m/z 265, 267 (M+H)$^+$.

Example 16

Synthesis of 3-methylbenzo[b]1,2,3-triazino[4,5-d]selenophen-4-one (compound 16)

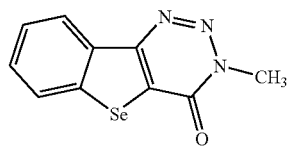

compound 16

Step a:

3-Aminobenzo[b]selenophene-2-carbonitrile: To a suspension of sodium selenide (9.14 g, 72.6 mmol, prepared from 5.8 g of selenium as described above) in DMF (72 mL) was added a solution of 2-chlorobenzonitrile (10 g, 72.6 mmol) in DMF (25 mL) at rt for 5 min and stirred the mixture at 100-110° C. for 24 h. Then chloroacetonitrile (5.48 mL, 72.6 mmol) was added dropwise to the reaction mixture and again stirred at 60-70° C. for 2 h. Then, a solution of sodium methoxide (3.9 g, 72.6 mmol) in dry methanol (24 mL) was added dropwise and stirring was continued for 2 h at the same temperature. The mixture was allowed to room temperature (rt) and poured into cold water and stirred for 30 min. The precipitated solid was filtered, washed with water and dried to give the product as an off-white color solid (7 g, 44%), mp 158-160° C. $^1$H NMR (400 MHz, CDCl$_3$): δ 7.76-7.79 (1H, m, H-7), 7.60-7.63 (1H, m, H-4), 7.41-7.52 (2H, m, H-5,6), 4.90 (2H, br s, —NH$_2$).

Step b:

3-Aminobenzo[b]selenophene-2-carboxamide: To a suspension of 3-aminobenzo[b]selenophene-2-carbonitrile (5.0 g) in aqueous sodium hydroxide solution (100 mL, 10%) was added ethanol (60 mL) and the mixture refluxed for 1 h. Ethanol was distilled off under vacuum (appr. 25 mL) and the mixture was allowed to cool to 5-10° C. The separated crystals were filtered off, washed with cold water and dried to give the product as a off-white color solid (3 g, 60%), mp 180-182° C. $^1$H NMR (400 MHz, DMSO-d$_6$): δ 7.99-8.01 (1H, m, H-7), 7.92-7.94 (1H, m, H-4), 7.40-7.42 (2H, m, H-5,6), 7.21 (2H, s, —CONH$_2$), 6.97 (2H, s, —NH$_2$); LC-MS (positive ion mode): m/z 261, 263 (M+Na)$^+$.

Step c:

3H-Benzo[b]1,2,3-triazino[4,5-d]selenophen-4-one: To an ice cold (0° C.) solution of 3-aminobenzo[b]selenophene-2-carboxamide (1.0 g, 4.16 mmol) in concentrated sulfuric acid (25 mL) was added a cold (0° C.) solution of sodium nitrite (0.316 g, 4.58 mmol) in concentrated sulfuric acid (10 mL) for 10 min (while adding, the temperature should keep between −5-0° C.). After addition, the mixture was stirred at 0° C. for 1 h and at rt for 2 h. The reaction mixture was cooled, poured into crushed ice slowly with stirring for 15 min and stirred at the same temperature for 15 min. The solution was extracted with ethyl acetate (3×200 mL) and the combined EtOAc layer was washed with water, brine and dried over sodium sulfate. The solution was filtered, evaporated the solvent to give the product as a yellow color solid (200 mg, 19%), mp 176-178° C. $^1$H NMR (400 MHz, DMSO-d$_6$): δ 15.48 (1H, s, —NH), 8.53-8.58 (1H, m, H-9), 8.41-8.46 (1H, m, H-6), 7.74-7.80 (2H, m, H-7,8).

Step d:

3-Methylbenzo[b]1, 2,3-triazino[4,5-d]selenophen-4-one: To a solution of 3H-benzo[b]1,2,3-triazino[4,5-d]selenophen-4-one (200 mg, 0.8 mmol) in acetone (50 mL) was added sequentially potassium carbonate (400 mg, 1.6 mmol), iodomethane (0.1 mL, 0.9 mmol) and a catalytic amount of PEG-400 was added at rt and the mixture was stirred at rt for 16 h. The solution was filtered and the solids were washed with acetone. Acetone was evaporated under reduced pressure and the residue was chromatographed over silica gel column using hexane-chloroform (70:30) as eluents to give the product as a off-white solid (120 mg, 47%), mp 190-192° C. IR (neat) $v_{max}$ 3431, 1673, 1220, 1021 cm$^{-1}$; $^1$H NMR (400 MHz, CDCl$_3$): δ 8.56-8.58 (1H, m, H-9), 7.98-8.01 (1H, m, H-6), 7.58-7.66 (2H, m, H-7,8), 4.13 (3H, s, —NCH$_3$); $^{13}$C NMR (100 MHz, CDCl$_3$): δ 155.5, 152.8, 142.3, 135.3, 130.4, 129.8, 126.4, 126.2, 126.0, 37.8; LC-MS (positive ion mode): m/z 286, 288 (M+Na)$^+$.

Example 17

Assessment of Anti-Melanoma Activity of Selenopheno Triazene Compounds of General Formula (I) and (II) by MTT Based Cell Proliferation Assay MTT [3-(4,5-dimethylthiazol-2-yl)-2,5-diphenyltetrazolium bromide] incorporation based cell proliferation assay was performed using standard procedure. The cytotoxic efficacies of the various selenopheno triazene compounds (compounds 1 to 16) was evaluated in both human malignant melanoma A375 cells and mouse malignant melanoma B16 F0 cells by MTT cell proliferation assay kit (Roche Applied Sciences, Germany). The assay was carried out according to the instruction provided by the vendor. Briefly, equal numbers of cells was plated in 96-well flat-bottomed plates and were incubated with both DTIC and the test compounds (compounds 1 to 16) at various concentrations for a period of three days. Vehicle control culture wells received only a maximum of 0.5% DMSO. Thereafter, 0.5 mg/ml of MTT reagent was added to each well and the microplate was incubated further for 4 h at 37° C. in presence of 5% CO$_2$. Finally, the cells were solubilized by adding solubilizing solution and allowed to incubate at 37° C. overnight. After complete solubilization of the formazan crystals, the absorbance was read at 540 nm in a microplate reader (BioRad, USA). The results (mean OD±SD) obtained from quadruplicate wells were used in calculation to determine the inhibition of cell proliferation (50% of inhibitory concentration, IC$_{50}$) of the test compounds (compounds 1 to 16) (Table 1).

MTT based cell proliferation assays indicate that among the test compounds (compounds 1 to 16), 4-[(dimethylamino) diazenyl]-5-methylselenophene-2-carboxamide (Compound 1) exhibited the best efficacy in inhibiting melanoma tumor cell growth in vitro (Table 1). In comparison with the marketed standard drug, Dacarbazine, Compound 1 has shown 5 times and 8 times more potent inhibition in mouse melanoma B16 cells and in human melanoma A375 cells, respectively.

TABLE 1

Anti-melanoma growth potential of compounds of general formula (I) and (II)

| | | Activity on Cell proliferation inhibition in | |
|---|---|---|---|
| Serial# | Name | B16F0 cells | A375 cells |
| 1 | Compound 1 | IC$_{50}$ 46.6 µg/ml | IC$_{50}$ 9.81 µg/ml |
| 2 | Compound 2 | N/A up to 100 µg/ml | N/A up to 10 µg/ml |
| 3 | Compound 3 | 30% at 100 µg/ml | 14% at 10 µg/ml |
| 4 | Compound 4 | 34% at 60 ug/ml | 0.5% at 10 µg/ml |
| 5 | Compound 5 | 0.41% at 60 ug/ml | N/A up to 10 µg/ml |
| 6 | Compound 6 | 4% at 60 µg/ml | N/A up to 10 µg/ml |
| 7 | Compound 7 | 5% at 100 µg/ml | N/A up to 10 µg/ml |
| 8 | Compound 8 | IC$_{50}$ 43.6 µg/ml | 24% at 10 µg/ml |
| 9 | Compound 9 | 32% at 60 µg/ml | N/A up to 10 µg/ml |
| 10 | Compound 10 | 12% at 60 µg/ml | N/A up to 10 µg/ml |
| 11 | Compound 11 | 48% at 60 µg/ml | N/A up to 10 µg/ml |
| 12 | Compound 12 | 27% at 100 ug/ml | N/A up to 10 µg/ml |
| 13 | Compound 13 | 33% at 60 µg/ml | N/A up to 10 µg/ml |
| 14 | Compound 14 | 17% at 60 µg/ml | N/A up to 10 µg/ml |
| 15 | Compound 15 | N/A up to 10 µg/ml | N/A up to 10 µg/ml |
| 16 | Compound 16 | 31% at 60 µg/ml | N/A up to 10 µg/ml |
| 17 | DTIC-STD | IC$_{50}$ 325.4 µg/ml | IC$_{50}$ 70.1 µg/ml |

Example 18

Growth Inhibitory Potential of Compound 1 in Some Other Tumor Cells of Different Tissue Origin Anti-tumor growth potential of Compound 1 and DTIC were evaluated in various human tumor cells such as A549 lung tumor cells, DU145 prostate tumor cells, HT29 colon cancer cells and MCF-7 (ER$^+$) breast tumor cells in vitro, by using MTT based cell proliferation assay as described earlier (example 17). The results (mean OD±SD) obtained from quadruplicate wells were used in calculation to determine the inhibition of cell proliferation (50% of inhibitory concentration, IC$_{50}$) of the test compounds (Table 2).

TABLE 2

Comparative anti-tumor growth potential of Compound 1 in some other human cancer cells of different tissue origin

| | | Anti-tumor growth potential (IC50) in | | | |
|---|---|---|---|---|---|
| Serial # | Compounds | A549 | DU145 | HT29 | MCF-7 |
| 1 | Compound 1 | 7.68 µg/ml | 8.97 µg/ml | 13.3 µg/ml | 7.03 µg/ml |
| 2 | DTIC | 95 µg/ml | 58.5 µg/ml | 141 µg/ml | 85.1 µg/ml |

Example 19

Cytotoxicity Potential of Compound 1

Cytotoxicity potential of DTIC and the Compound 1 was evaluated by measuring the leaked lactate dehydrogenase (LDH) into the tumor cells culture supernatant (LDH Cytotoxicity Detection Kie$^{Plus}$, Roche Applied Sciences, Germany). The leaked LDH is directly proportional to the cell damage done by the cytotoxic compounds. Briefly, equal number of human malignant melanoma A375 cells or mouse melanoma cells B16 F0 were treated with test compounds at various concentrations and incubated for 48 h. Vehicle control culture wells received only a maximum of 0.5% DMSO. The cell free culture supernatants were mixed with catalyst and dye solution and allowed to incubate for 15 min at room temperature. Finally, the reaction was stopped and the optical density was measured at 492 nm in a microplate reader (Bio-Rad, USA). The results (mean OD±SD) obtained from quadruplicate wells were used in calculation to determine the cytotoxicity potential (50% of inhibitory concentration, IC$_{50}$) of the test compounds. A bar diagram depicts the loss of cell viability of B16 F0 and A375 cells as indicated by percent increase of leaked LDH in DTIC and compound 1 treated versus drug concentration as depicted in FIGS. 1A and 1B, respectively.

Example 20

Tumor Selectivity

Next, to check whether the Compound 1 can selectively kill the melanoma cells without or minimally affecting the normal cells, we assessed the comparative efficacy of the Compound 1 and DTIC on cell growth inhibition of HS.531.sk normal human skin epithelial cells. The growth inhibitory effect of the test compound and DTIC was assessed by MTT proliferation assay as described earlier (Example 17). The comparative efficacies of Compound 1 and DTIC in inhibiting the normal skin epithelial cell growth are depicted in FIG. 2. At 25 µg/ml concentration, compound 1 and DTIC exhibited 2.33% and 34.58% growth inhibition of HS.531.sk normal human skin epithelial cells; and at 50 µg/ml concentration, these two anti-melanoma drugs showed 23.83% and 43.46% growth inhibitions in the normal skin epithelial cells, respectively. These data together clearly indicate that the compound 1 more selectively inhibits the human melanoma tumor cells growth with minimally affecting the growth of normal cells, compared to the marketed anti-melanoma drug DTIC.

Example 21

B16 F0 Mouse Melanoma Cell Colony Formation Assay

Figure 3:
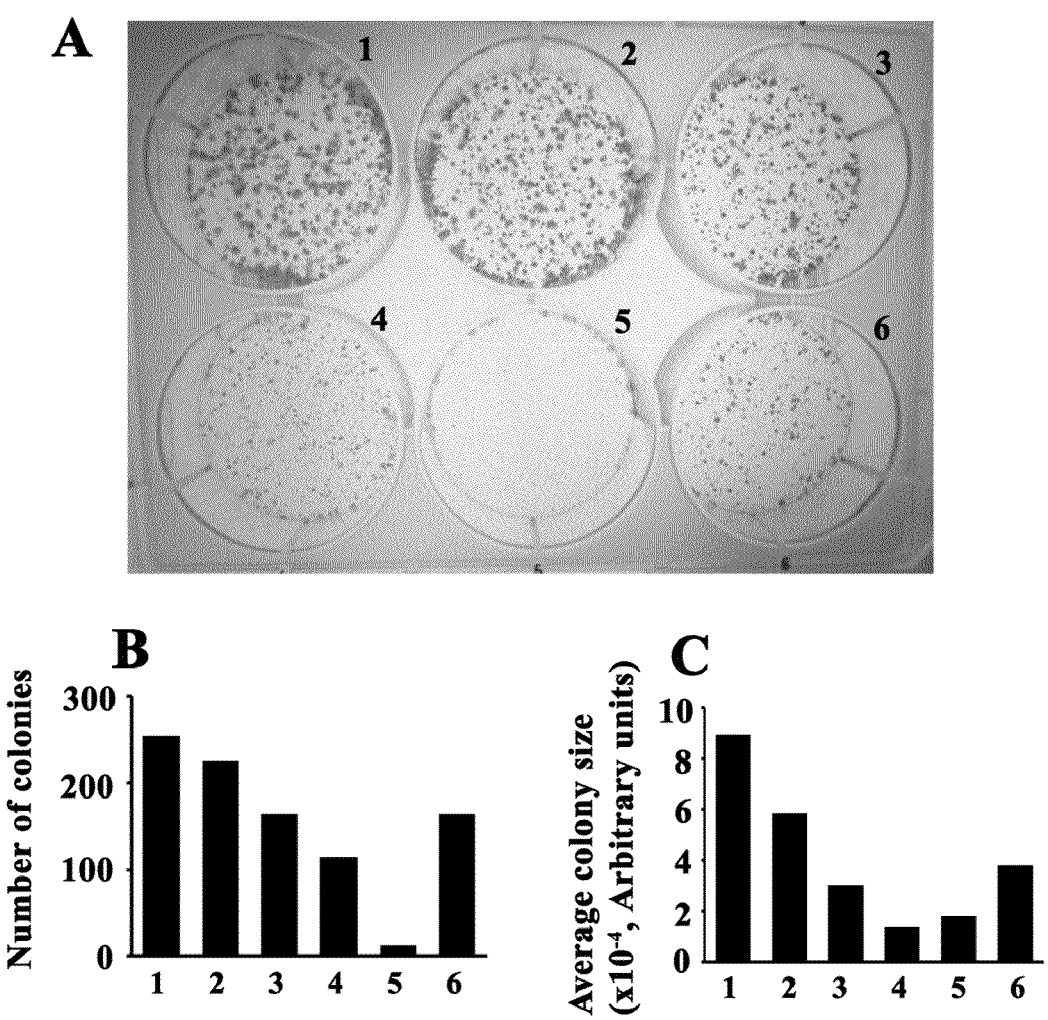
FIG. 3: Panel A represents images showing inhibition of B16F0 colony formation in presence of Compound 1 and DTIC in vitro. B16F0 cells were treated with 0.1% DMSO (1), or 1, 5, 10, 20 µg/ml of Compound 1 (2-5, respectively) or 100 µg/ml of DTIC (6). The average number of colonies and the average size of the colonies are presented in panels B and C, respectively.

Inhibitory efficacy in clone formation of the Compound 1 and DTIC was tested by following the procedure described earlier with some modifications. Briefly, B 16F0 cells were harvested and seeded into 6-well plates (100 cells/ml). The cells were allowed to grow for 4 days and thereafter, the cells were incubated with DMEM containing either 0.1% DMS 0 or 100 µg/ml DTIC or different concentrations (1, 5, 10 or 20 µg/ml) of Compound 1 for further 8 days. Fresh medium containing test agents was replaced at every 24 h. Finally, the wells were washed three times with PBS and fixed in methanol for 15 min. The cells were stained with Giemsa stain and observed under microscope. The image of the stained wells were captured digitally (Kodak Image Station 4000 mM, Carestream Health Inc., New Haven, Conn.) and number of colonies were counted and analyzed by using NIH Image J software. FIG. 3 shows inhibition of B16 colony growth in DTIC and Compound 1 treated wells. Compound 1 exhibited significant inhibition in B16 tumor cell colony growth compared with DTIC. At 100 µg/ml concentration, DTIC showed only 35.8% inhibition, in contrast, 11%, 35%, 54% and 94% reductions in number of colonies were achieved by 1, 5, 10 or 20 µg/ml of Compound 1, respectively.

Example 22

Compound 1 Inhibits Invasion of B16F0 Mouse Melanoma Cells

Figure 4:
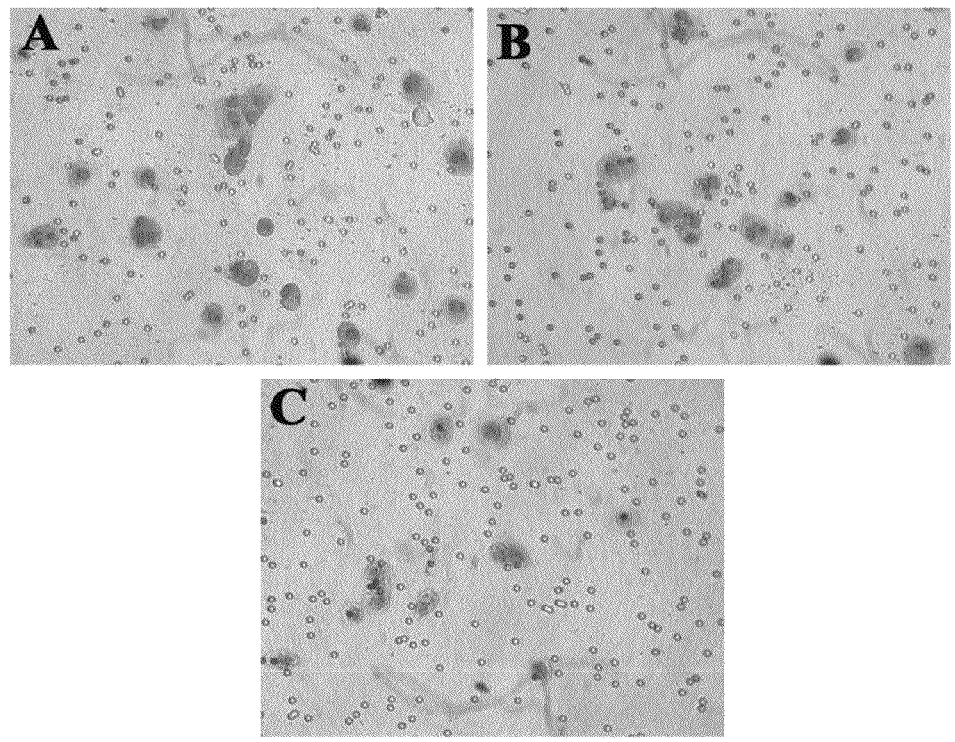
FIG. 4: Photomicrographs show invaded B 16F0 cells in vehicle control (A), 100 µg/ml of DTIC (B), and 20 µg/ml of Compound 1 (C) treated cultures. Bar diagram represents the average number±SD of invaded cells in respective cultures counted from 20 independent fields observed at 20× objective. *indicates significance (p<0.05) vs. vehicle control (Student T-test).
Figure 4:
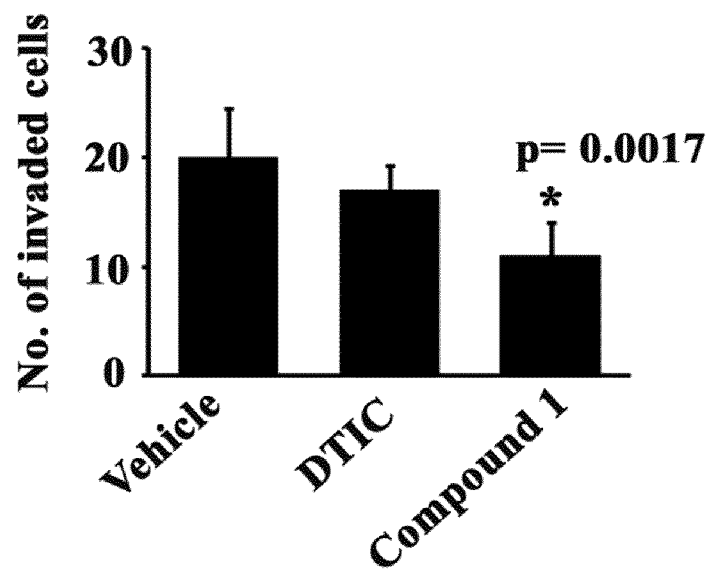

The inhibitory effects of DTIC and compound 1 on invasive ability of B16F0 were tested in cell invasion assay performed with by using Matrigel (BME-Cultrex®, R&D Systems, USA) coated cell culture inserts (Becton Dickinson, USA) with 8 µm-pore membrane. Equal number (fifty thousands) of B16F0 cells were applied in each insert well and allowed to attach for 2 h at 37° C. and in presence of 5% $CO_2$. Thereafter, the cellular invasion through the matrigel layer was performed in presence or absence of test compounds. Either 100 µg/ml of DTIC or 20 µg/ml of Compound 1 was applied in the lower chamber of the invasion assembly. 0.1% DMSO was applied in the vehicle control culture chambers. After 24 h treatment, the matrigel layer containing cells was removed with cotton plug and the invaded cells on the other side of the membrane were fixed with methanol for 5 min and then stained with Giemsa. The stained membrane was mounted on a glass slide and number invaded cells were counted in 20 random fields (20× objective) under a light microscope (Nikon Eclipse TS 100). In comparison with the vehicle treated control, Compound 1 significantly reduced (p=0.0017) B16 F0 malignant melanoma tumor cell invasion, whereas, DTIC could not significantly inhibit B16 melanoma cell invasion in in vitro (FIG. 4).

Example 23

Compound 1 Inhibits Migration of Human Endothelial Cells

Figure 5:
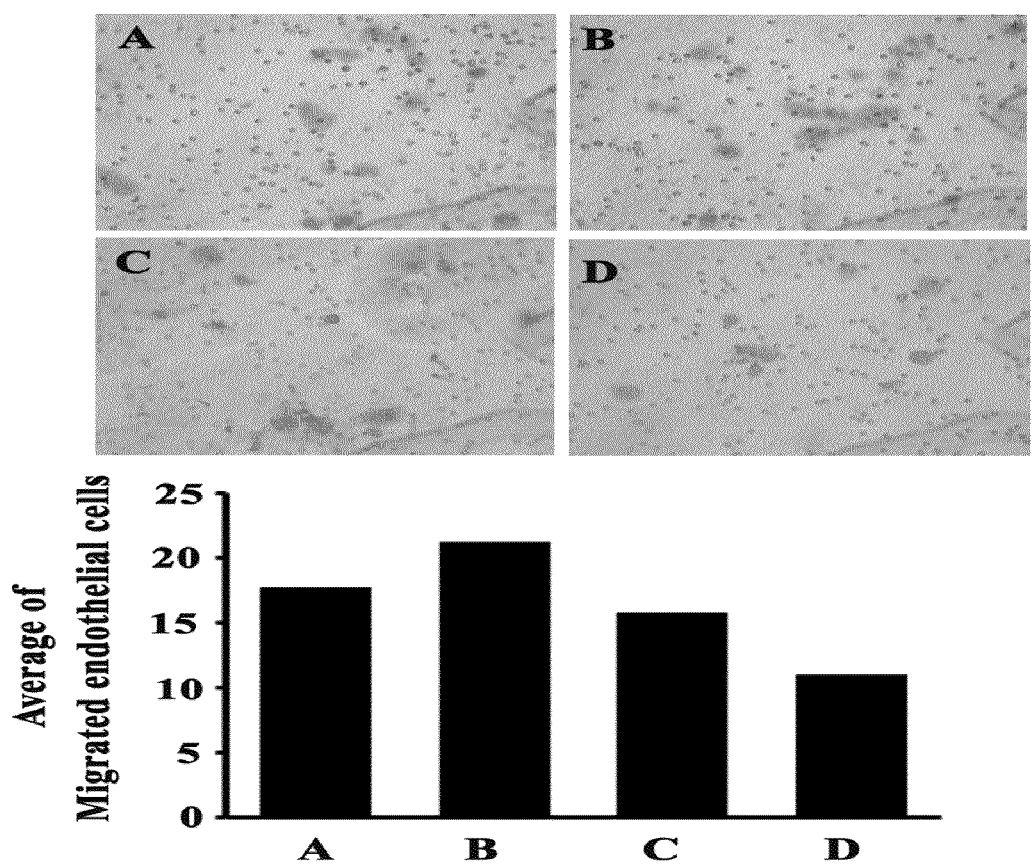
FIG. 5: Pictures show inhibitory effect of Compound 1 on human endothelial cell migration. Microphotographs illustrate the migration of HUVECs in the presence of either 100 µg/ml of DTIC (B) or Compound 1 at 5 µg/ml (C) or Compound 1 at 10 µg/ml (D), respectively. Panel A represents cellular migration in 0.1% DMSO treated vehicle control wells. The bar graph shows the average number of migrated cells under different culture conditions as indicated under each bar. Each bar represents mean of migrated cells calculated from at least twenty fields under 20× objective.

The methodology of endothelial cell migration assay was essentially the same as described earlier with some modifications (Sengupta, K et al., *Mol. Cancer. Res.* 2004; 2: 150-158.). FALCON™ Cell Culture inserts (Becton Dickinson, USA) with 8 µm-pores in their PET membrane was coated with 0.1 mg/ml of collagen. Human umbilical vein endothelial cells (HUVEC) were added to the cell culture inserts (Becton Dickinson) at a density of 5×10$^4$ cells/insert. Cells were allowed to migrate through the insert for 18 h in presence of different concentrations of either DTIC or Compound 1. The control culture containing migration assembly received only 0.1% DMSO. The cells which did not migrate were scrapped off by cotton plug and the migrated cells were fixed with methanol for 5 min and then stained with Giemsa. The membranes of the inserts were then mounted on glass slides. Cells migrated through the membrane pores were counted in 20 random fields under Nikon Eclipse TS 100 microscope at 20× objective. FIG. 5 shows significant inhibition of migration of Compound 1 treated endothelial cells.

Example 24

Compound 1 Inhibits Endothelial Capillary Tube Formation In Vitro

In vitro capillary formation assay was performed with Human umbilical vein endothelial cells (HUVEC), cultured on 10 mg/ml basement membrane extract (BME-Cultrex®, R&D Systems, USA) bed. The protocol of in vitro endothelial tube formation assay was the same as described earlier with some modifications (Diana G et al., *J. Cell Biol.* 1995; Volume 130: 207-215.). Briefly, four hundred microliters of Cultrex was coated at 4° C. in each well of 24-well culture plate and allowed to gel at 37° C. for 1 h. HUVECs were plated at a density of $7.5 \times 10^4$ cells per well with 400 μl of DMEM supplemented with 10% fetal bovine serum and 4.5 g/l D-glucose. The cells were then treated with either DTIC or Compound 1 at desired concentration as indicated for 16 hours. Vehicle control cultures received only 0.1% DMSO. Pictures were taken under a Nikon Eclipse TS 100 microscope equipped with a Nikon Coolpix camera. Compound 1 exhibited inhibition of capillary formation in a dose dependent manner, in contrast, DTIC promoted capillary formation with human endothelial cells in in vitro culture condition (FIG. 6).

Example 25

Anti Tumor Growth Potential of Compound 1 in B16 F0 Melanoma Xenograft Model of C57B6J Mice In vivo efficacy of compound 1 against melanoma growth was evaluated in B 16 F0 melanoma xenograft model of C57B6J mice. C57B6J mice of 6 weeks age (body weight 18-22 g) were purchased from National Institute of Nutrition (NIN), Hyderabad (India). Animals study protocols were approved by Institutional Ethics Committee (IAEC). All the studies were performed in compliance with the Committee for the Purpose of Control and Supervision of Experiments on Animals (CPCSEA) guidelines and OECD guidelines. Animals were allowed free access to standard feed and provided charcoal filtered and UV exposed water ad libitum. The animals were maintained at a controlled temperature (24-26° C.), humidity (45-70%), and 12 h/12 h of light/dark cycle.

To induce the melanoma tumor formation, sub-confluent B16F0 cells were harvested by brief trypsinization and $1 \times 10^6$ cells were injected subcutaneously in 0.2 ml phosphate-buffered saline. Drug treatment was started after development of palpable tumors (3-5 days after implantation of the cells). Drugs were prepared in phosphate-buffered saline (10% DMSO, v/v) and either 75 mg/kg of DTIC or 25 mg/kg of compound 1 was administered daily through intra-peritoneal route. Vehicle treated control animals received only 10% DMSO in phosphate buffered saline. After fourteen days of treatment, the animals were sacrificed by $CO_2$ inhalation and tumors were excised and weighed. FIG. 7 shows comparative efficacy of inhibiting tumor growth by DTIC and compound 1 at various concentrations in B 16 F0 melanoma xenograft model of C57B6J mice.

Example 26

Anti Melanoma Efficacy of Compound 1 in A375 Human Melanoma Xenograft Model of Nu/Nu BALB/c Nude Mice To further substantiate the anti-melanoma efficacy of the Compound 1, this compound was tested for its anti-melanoma efficacy in A375 human melanoma xenograft model of nu/nu BALB/c nude mice. The animals of 6-8 weeks age (body weight 18-22 g) were used in this study. Animals study protocols were approved by Institutional Ethics Committee (IAEC). All the studies were performed in compliance with the Committee for the Purpose of Control and Supervision of Experiments on Animals (CPCSEA) guidelines and OECD guidelines. Animals were allowed free access to sterile standard rodent diet and provided with charcoal filtered and UV exposed water ad libitum. The animals were housed in a sterile room and were located individually in ventilated cages. The room was maintained at a controlled temperature (24-26° C.), humidity (45-70%), and 12 h/12 h of light/dark cycle.

To induce the melanoma tumor, sub-confluent A375 human melanoma cells were harvested by brief trypsinization and $1 \times 10^6$ cells were injected subcutaneously in 0.2 ml phosphate-buffered saline. Drug treatment was started after development of palpable tumors (6-7 days after implantation of the cells). At this point the tumor take rate was 100%. Compound 1 was prepared in phosphate-buffered saline containing 10% DMSO (v/v); and 25 mg/kg of compound 1 was administered daily through intra-peritoneal route. Vehicle treated control animals received only 10% DMS 0 in phosphate buffered saline. After twenty one days of treatment, the animals were sacrificed by $CO_2$ inhalation and tumors growth was measured by the following formula (Friedman H S et al., Mol Cancer Ther 2002; 1:943-948).

$$[(\text{length}) \times (\text{width})^2]/2$$

Compound 1 significantly (p=0.04322) inhibits the melanoma tumor growth in comparison with the vehicle treated group (FIG. 8). Compound 1 is able to inhibit 46.52% melanoma tumor growth in human melanoma xenograft model of nude mice. This observation substantiates its anti-melanoma efficacy and strengthens our finding that compound 1 can used as a potential therapeutic agent to treat human malignant melanoma.

The invention claimed is:
1. A compound of formula (I) having a selenophene ring or a pharmaceutically acceptable salt thereof:

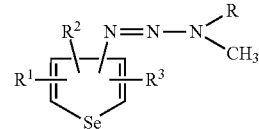

Formula I wherein:
R is selected from H, $CH_3$ and $CH_2OH$;
$R^1$, $R^2$ and $R^3$ are each independently selected from the group consisting of H, N=N—N($CH_3$)$_2$, N=N—NH$CH_3$, N=NN($CH_3$)$CH_2OH$, $CONH_2$, $CONHR^4$, $CONR^4R^5$, $CONHNH_2$, $CONHNHR^4$, $CONHNR^4R^5$, $COOCH_3$, $COOCH_2CH_3$, COON, COSH, CN, C≡CH, $SO_2NH_2$, $SO_2NHR^4$, $SO_2NR^4R^5$, $NO_2$, $CF_3$, Cl, Br, F, $CCl_3$, $CH_3$, OH, $OCH_3$, SH, $SCH_3$, $NH_2$, $NHCH_3$, $N(CH_3)_2$, alkyl, alkenyl, electron withdrawing functional groups and electron donating functional groups,
wherein $R^4$ and $R^5$ are independently selected from the group consisting of H, $CH_3$, $C_1$-$C_{10}$ alkyl, alkenyl, alkylol, alkoxy, and alkylamine;
or wherein any two of $R^1$, $R^2$ and $R^3$ are joined together to form a ring selected from the group consisting of an alicyclic, aromatic, or heterocyclic ring system which is fused to two adjacent carbon atoms in said selenophene ring.

2. The compound of claim 1, wherein any two of $R^1$, $R^2$ and $R^3$ are selected from the group consisting of said alicyclic, aromatic, or heterocyclic ring system, said ring system being a cyclopentyl ring, a cyclohexyl ring, a phenyl ring or a pyridyl ring.

3. The compound of claim 1, wherein said compound is selected from the group consisting of:
   a) 4-[(dimethylamino)diazenyl]-5-methylselenophene-2-carboxamide;
   b) 3-[(dimethylamino)diazenyl]selenophene-2,5-dicarboxamide;
   c) 3-[(dimethylamino)diazenyl]-5-phenylselenophene-2-carboxamide;
   d) 3-[(dimethylamino)diazenyl]-5-(tert-butyl)selenophene-2-carboxamide;
   e) 3-[(dimethylamino)diazenyl]-4,5,6,7-tetrahydrobenzo[1,2-b]selenophene-2-carboxamide;
   f) 3-[(dimethylamino)diazenyl]selenopheno[2,3-b]pyridine-2-carboxamide;
   g) 3-[(dimethylamino)diazenyl]-5-phenylselenophene-2-carboxylic acid;
   h) 3-[(dimethylamino)diazenyl]-5-(tert-butyl)selenophene-2-carboxylic acid;
   i) 3-[(dimethylamino)diazenyl]-4,5,6,7-tetrahydrobenzo[1,2-b]selenophene-2-carboxylic acid;
   j) 3-[(dimethylamino)diazenyl]selenopheno[2,3-b]pyridine-2-carboxylic acid; and
   k) 3-[(dimethylamino)diazenyl]-5-(tert-butyl)selenophene-2-carbonitrile.

4. A compound of formula (II) having a selenophene ring or a pharmaceutically acceptable salt thereof:

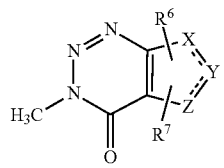

Formula II wherein:
the notation ----- represents a single bond or a double bond;
X, Y and Z are independently selected from C and Se so as to form a selenophene ring, with the proviso that a double bond is either in between X and Y or in between Y and Z;
$R^6$ and $R^7$ are either:
a) independently selected from H, N=N—N(CH$_3$)$_2$, N=N—NHCH$_3$, N=N—N(CH$_3$)CH$_2$OH, CONH$_2$, CONHR$^8$, CONR$^8$R$^9$, CONHNH$_2$, CONHNHR$^8$, CONHNR$^8$R$^9$, COOCH$_3$, COOCH$_2$CH$_3$, COOH, COSH, CN, CECH, SO$_2$NH$_2$, SO$_2$NHR$^8$, SO$_2$NR$^8$R$^9$, NO$_2$, CF$_3$, Cl, Br, F, CCl$_3$, CH$_3$, OH, OCH$_3$, SH, SCH$_3$, NH$_2$, NHCH$_3$, N(CH$_3$)$_2$, alkyl, alkenyl, electron withdrawing functional groups, and electron donating functional groups; or
b) joined together to form an alicyclic, aromatic, or heterocyclic ring system which is fused to two adjacent carbon atoms in said selenophene ring; and
$R^8$ and $R^9$ are independently selected from H, CH$_3$, C$_1$-C$_{10}$ alkyl, alkenyl, alkylol, alkoxy, and alkylamine.

5. The compound of claim 4, wherein said alicyclic, aromatic, or heterocyclic ring system is a cyclopentyl ring, a cyclohexyl ring, a phenyl ring or a pyridyl ring.

6. The compound of claim 4, wherein said compound is selected from the group consisting of:
   a) 3-methyl-6-phenylselenopheno[3,2-d]1,2,3-triazin-4-one;
   b) 6-(tert-butyl)-3-methylselenopheno[3,2-d]1,2,3-triazin-4-one;
   c) 3-methyl-6,7,8,9-tetrahydrobenzo[1,2-b]1,2,3-triazino[4,5-d]selenophen-4-one;
   d) 3-methyl-1,2,3-triazino[4',5'-5,4]selenopheno[2,3-b]pyridine-4-one; and
   e) 3-methylbenzo[b]1,2,3-triazino[4,5-d]selenophen-4-one.

7. A pharmaceutical composition comprising at least one compound of claim 1 or a pharmaceutically acceptable salt thereof, in combination with at least one selected from pharmaceutically acceptable excipient, pharmaceutically acceptable diluent, and pharmaceutically acceptable carrier.

8. A pharmaceutical composition comprising at least one compound of claim 4 or a pharmaceutically acceptable salt thereof, in combination with at least one selected from pharmaceutically acceptable excipient, pharmaceutically acceptable diluent, and pharmaceutically acceptable carrier.

9. A pharmaceutical composition according to claim 7, further comprising at least one compound of formula (II) having a selenophene ring or a pharmaceutically acceptable salt thereof:

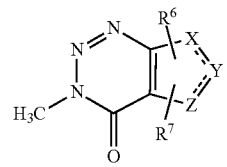

Formula II wherein:
the notation ----- represents a single bond or a double bond;
X, Y and Z are independently selected from C and Se so as to form a selenophene ring, with the proviso that a double bond is either in between X and Y or in between Y and Z;
$R^6$ and BY are either:
a) independently selected from H, N=N—N(CH$_3$)$_2$, N=N—NHCH$_3$, N=N—N(CH$_3$)CH$_2$OH, CONH$_2$, CONHR$^8$, CONR$^8$R$^9$, CONHNH$_2$, CONHNHR$^8$, CONHNR$^8$R$^9$, COOCH$_3$, COOCH$_2$CH$_3$, COOH, COSH, CN, CECH, SO$_2$NH$_2$, SO$_2$NHR$^8$, SO$_2$NR$^8$R$^9$, NO$_2$, CF$_3$, Cl, Br, F, CCl$_3$, CH$_3$, OH, OCH$_3$, SH, SCH$_3$, NH$_2$, NHCH$_3$, N(CH$_3$)$_2$, alkyl, alkenyl, electron withdrawing functional groups, and electron donating functional groups; or
b) joined together to form an alicyclic, aromatic, or heterocyclic ring system which is fused to two adjacent carbon atoms in said selenophene ring; and
$R^8$ and $R^9$ are independently selected from H, CH$_3$, C$_1$-C$_{10}$ alkyl, alkenyl, alkylol, alkoxy, and alkylamine.

10. A pharmaceutical composition comprising at least one compound of claim 1 or a pharmaceutically acceptable salt thereof, further comprising at least one chemotherapeutic agent in combination with at least one selected from pharmaceutically acceptable excipient, pharmaceutically acceptable diluent, and pharmaceutically acceptable carrier.

11. The pharmaceutical composition of claim 8, further comprising at least one chemotherapeutic agent.

12. The pharmaceutical composition of claim 9, further comprising at least one chemotherapeutic agent.

13. The composition as claimed in claim 10, wherein said chemotherapeutic agent is selected from the group consisting of 5-fluorouracil, 6-mercaptopurine, actinomycin, doxorubicin, aminoglutethimide, anastrozole, bevacizumab, bleomycin, carboplatin, cactinomycin, capecitabine, cisplatin, clodronic acid, cyclophosphamide, dactinomycin, docetaxel, doxorubicin, epirubicin, etoposide, exemestane, fluorouracil, fluoxymesterone, letrozole, leucovorin calcium, megestrol, megestrol acetate, methotrexate, mitomycin, mitoxantrone, paclitaxel, pamidronate, prednisone, tamoxifen, trastuzumab, thiotepa, vinblastine, vincristine, vinorelbine, pharmaceutically acceptable salts thereof, and mixtures thereof.

14. The composition as claimed in claim 11, wherein said chemotherapeutic agent is selected from the group consisting of 5-fluorouracil, 6-mercaptopurine, actinomycin, doxorubicin, aminoglutethimide, anastrozole, bevacizumab, bleomycin, carboplatin, cactinomycin, capecitabine, cisplatin, clodronic acid, cyclophosphamide, dactinomycin, docetaxel, doxorubicin, epirubicin, etoposide, exemestane, fluorouracil, fluoxymesterone, letrozole, leucovorin calcium, megestrol, megestrol acetate, methotrexate, mitomycin, mitoxantrone, paclitaxel, pamidronate, prednisone, tamoxifen, trastuzumab, thiotepa, vinblastine, vincristine, vinorelbine, pharmaceutically acceptable salts thereof, and mixtures thereof.

15. The composition as claimed in claim 12, wherein said chemotherapeutic agent is selected from the group consisting of 5-fluorouracil, 6-mercaptopurine, actinomycin, doxorubicin, aminoglutethimide, anastrozole, bevacizumab, bleomycin, carboplatin, cactinomycin, capecitabine, cisplatin, clodronic acid, cyclophosphamide, dactinomycin, docetaxel, doxorubicin, epirubicin, etoposide, exemestane, fluorouracil, fluoxymesterone, letrozole, leucovorin calcium, megestrol, megestrol acetate, methotrexate, mitomycin, mitoxantrone, paclitaxel, pamidronate, prednisone, tamoxifen, trastuzumab, thiotepa, vinblastine, vincristine, vinorelbine, pharmaceutically acceptable salts thereof, and mixtures thereof.

16. A pharmaceutical composition comprising at least one compound of claim 1 or a pharmaceutically acceptable salt thereof, further comprising:
   at least one agent selected from the group consisting of monoclonal antibodies, interferons, interleukins, colony stimulating factors, and TNF-α receptor blocker drugs, in combination with
   at least one component selected from pharmaceutically acceptable excipients, pharmaceutically acceptable diluents, and pharmaceutically acceptable carriers.

17. The pharmaceutical composition of claim 8, further comprising at least one agent selected from the group consisting of monoclonal antibodies, interferons, interleukins, colony stimulating factors, and TNF-α receptor blocker drugs.

18. The pharmaceutical composition of claim 9, further comprising at least one agent selected from the group consisting of monoclonal antibodies, interferons, interleukins, colony stimulating factors, and TNF-α receptor blocker drugs.

19. A method of treating a disease selected from the group consisting of melanoma, lung tumors, prostate tumors, colon cancer, and breast tumors in a warm blooded animal suffering from such disease, wherein said method comprises administering to the said warm blooded animal a therapeutically effective amount of at least one compound according to claim 1.

20. A method of treating a disease selected from the group consisting of melanoma, lung tumors, prostate tumors, colon cancer, and breast tumors in a warm blooded animal suffering from such disease, wherein said method comprises administering to the said warm blooded animal a therapeutically effective amount of at least one compound according to claim 4, alone or in combination with a compound of formula (I) having a selenophene ring or a pharmaceutically acceptable salt thereof:

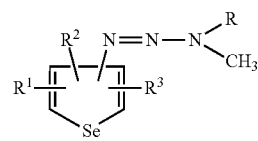

Formula I wherein:
   R is selected from H, $CH_3$ and $CH_2OH$;
   $R^1$, $R^2$ and $R^3$ are each independently selected from the group consisting of H, $N=N-N(CH_3)_2$, $N=N-NHCH_3$, $N=NN(CH_3)CH_2OH$, $CONH_2$, $CONHR^4$, $CONR^4R^5$, $CONHNH_2$, $CONHNHR^4$, $CONHNR^4R^5$, $COOCH_3$, $COOCH_2CH_3$, COOH, COSH, CN, $C\equiv CH$, $SO_2NH_2$, $SO_2NHR^4$, $SO_2NR^4R^5$, $NO_2$, $CF_3$, Cl, Br, F, $CCl_3$, $CH_3$, OH, $OCH_3$, SH, $SCH_3$, $NH_2$, $NHCH_3$, $N(CH_3)_2$, alkyl, alkenyl, electron withdrawing functional groups and electron donating functional groups,
   wherein $R^4$ and $R^5$ are independently selected from the group consisting of H, $CH_3$, $C_1$-$C_{10}$ alkyl, alkenyl, alkylol, alkoxy, and alkylamine;
   or any two of $R^1$, $R^2$ and $R^3$ are joined together to form a ring selected from the group consisting of an alicyclic, aromatic, or heterocyclic ring system which is fused to two adjacent carbon atoms in said selenophene ring.

21. A method of treating a disease selected from the group consisting of melanoma, lung tumors, prostate tumors, colon cancer, and breast tumors in a warm blooded animal suffering from such disease, wherein said method comprises administering to the said warm blooded animal a therapeutically effective amount of at least one compound according to claim 1 in combination with at least one additive selected from the group consisting of pharmaceutically acceptable excipients, pharmaceutically acceptable diluents and pharmaceutically acceptable carriers; at least one optional chemotherapeutic agent; and at least one optional agent selected from the group consisting of monoclonal antibodies, interferons, interleukins, colony stimulating factors, and TNF-α receptor blocker drugs.

22. A method of treating a disease selected from the group consisting of melanoma, lung tumors, prostate tumors, colon cancer, and breast tumors in a warm blooded animal suffering from such disease, wherein said method comprises administering to the said warm blooded animal a composition comprising a therapeutically effective amount of at least one compound according to claim 4;
   wherein said composition further comprises:
   at least one additive selected from the group consisting of pharmaceutically acceptable excipients, pharmaceutically acceptable diluents and pharmaceutically acceptable carriers;
   an optional chemotherapeutic agent;
   an optional agent selected from the group consisting of monoclonal antibodies, interferons, interleukins, colony stimulating factors, and TNF-α receptor blacker drugs; and an optional compound of formula (I) having a selenophene ring or a pharmaceutically acceptable salt thereof:

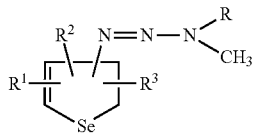

Formula I wherein:
R is selected from H, CH$_3$ and CH$_2$OH;
R$^1$, R$^2$ and R$^3$ are each independently selected from the group consisting of H, N=N—N(CH$_3$)$_2$, N=N—NHCH$_3$, N=NN(CH$_3$)CH$_2$OH, CONH$_2$, CONHR$^4$, CONR$^4$R$^5$, CONHNH$_2$, CONHNHR$^4$, CONHNHR$^4$R$^5$, COOCH$_3$, COOCH$_2$CH$_3$, COOH, COSH, CN, CECH, SO$_2$NH$_2$, SO$_2$NHR$^4$, SO$_2$NR$^4$R$^5$, NO$_2$, CF$_3$, Cl, Br, F, CCl$_3$, CH$_3$, OH, OCH$_3$, SH, SCH$_3$, NH$_2$, NHCH$_3$, N(CH$_3$)$_2$, alkyl, alkenyl, electron withdrawing functional groups and electron donating functional groups,
wherein R$^4$ and R$^5$ are independently selected from the group consisting of H, CH$_3$, C$_1$-C$_{10}$ alkyl, alkenyl, alkylol, alkoxy, and alkylamine;
or any two of R$^1$, R$^2$ and R$^3$ are joined together to form a ring selected from the group consisting of an alicyclic, aromatic, or heterocyclic ring system which is fused to two adjacent carbon atoms in said selenophene ring.

23. The method of claim 20, wherein any two of R$^1$, R$^2$ and R$^3$ are joined together to form a ring selected from the group consisting of said alicyclic, aromatic, or heterocyclic ring system, said ring system being a cyclopentyl ring, a cyclohexyl ring, a phenyl ring or a pyridyl ring.

24. A method of treating a disease selected from the group consisting of melanoma, lung tumors, prostate tumors, colon cancer, and breast tumors in a warm blooded animal suffering from such diseases, wherein the method comprises administering at least one compound or a pharmaceutically acceptable salt thereof as claimed in claim 1, in conjunction with a means of therapy selected from the group consisting of anti-angiogenesis therapy, chemotherapy, cytokine therapy, radiotherapy, gene therapy, hormonal therapy, surgery, vaccination, and a combination thereof.

25. A method of treating a disease selected from the group consisting of melanoma, lung tumors, prostate tumors, colon cancer, and breast tumors in a warm blooded animal suffering from such disease, wherein the method comprises administering at least one compound or a pharmaceutically acceptable salt thereof as claimed in claim 4, in conjunction with a means of therapy selected from the group consisting of anti-angiogenesis therapy, chemotherapy, cytokine therapy, radiotherapy, gene therapy, hormonal therapy, surgery, vaccination, and a combination thereof.

26. A method of treating a disease selected from the group consisting of melanoma, lung tumors, prostate tumors, colon cancer, and breast tumors as claimed in claim 19, wherein the said administration comprises the routes selected from the group consisting of intraperitoneal (IP), intravenous (IV), oral (PO), intramuscular (TM), intracutaneous (IC), intradermal (ID), intrauterine, intratumoral and intrarectal.

27. A method of treating a disease selected from the group consisting of melanoma, lung tumors, prostate tumors, colon cancer, and breast tumors as claimed in claim 20, wherein the said administration comprises the routes selected from the group consisting of intraperitoneal (IP), intravenous (IV), oral (PO), intramuscular (IM), intracutaneous (IC), intradermal (ID), intrauterine, intratumoral and intrarectal.

28. A method of treating a disease selected from the group consisting of melanoma, lung tumors, prostate tumors, colon cancer, and breast tumors as claimed in claim 19, wherein the said administration comprises administering the compounds through a dosage form selected from Liposome-based, Polymeric surfactant-based, Biodegradable block copolymers, Microencapsulation and Nanoparticles to said warm blooded animal.

29. A method of treating a disease selected from the group consisting of melanoma, lung tumors, prostate tumors, colon cancer, and breast tumors as claimed in claim 20, wherein the said administration comprises administering the compounds through a dosage form selected from Liposome-based, Polymeric surfactant-based, Biodegradable block copolymers, Microencapsulation and Nanoparticles to said warm blooded animal.

30. A method of treating a disease selected from the group consisting of melanoma, lung tumors, prostate tumors, colon cancer, and breast tumors in a warm blooded animal suffering from such disease, wherein said method comprises administering to the said warm blooded animal a therapeutically effective amount of at least one compound selected from the group consisting of:
a) 4-[(dimethylamino)diazenyl]-5-methylselenophene-2-carboxamide;
b) 3-[(dimethylamino)diazenyl]selenophene-2,5-dicarboxamide;
c) 3-[(dimethylamino)diazenyl]-5-phenylselenophene-2-carboxamide;
d) 3-[(dimethylamino) diazenyl]-5-(tert-butyl) selenophene-2-carboxamide;
e) 3-[(dimethylamino)diazenyl]-4,5,6,7-tetrahydrobenzo[1,2-b]selenophene-2-carboxamide;
f) 3-[(dimethylamino) diazenyl]selenopheno [2,3-b]pyridine-2-carboxamide
g) 3-[(dimethylamino)diazenyl]-5-phenylselenophene-2-carboxylic acid;
h) 3-[(dimethylamino)diazenyl]-5-(tert-butyl)selenophene-2-carboxylic acid;
i) 3-[(dimethylamino)diazenyl]-4,5,6,7-tetrahydrobenzo[1,2-b]selenophene-2-carboxylic acid;
j) 3-[(dimethylamino)diazenyl]selenopheno[2,3-b]pyridine-2-carboxylic acid;
k) 3-[(dimethylamino)diazenyl]-5-(tert-butyl)selenophene-2-carbonitrile;
l) 3-methyl-6-phenylselenopheno[3,2-d]1,2,3-triazin-4-one;
m) 6-(tert-butyl)-3-methylselenopheno[3,2-d]1,2,3-triazin-4-one;
n) 3-methyl-6,7,8,9-tetrahydrobenzo[1,2-b]1,2,3-triazino[4,5-d]selenophen-4-one;
o) 3-methyl-1,2,3-triazino[4',5'-5,4]selenopheno[2,3-b]pyridine-4-one; and
p) 3-methylbenzo[b]1,2,3-triazino[4,5-d]selenophen-4-one.

31. A method of treating a disease selected from the group consisting of melanoma, lung tumors, prostate tumors, colon cancer, and breast tumors in a warm blooded animal suffering from such disease in need thereof, wherein said method comprises administering to the said warm blooded animal, a composition comprising a therapeutically effective amount of at least one compound according to claim 30 or a pharmaceutically acceptable salt thereof, in combination with at least one selected from pharmaceutically acceptable excipients, pharmaceutically acceptable diluents and pharmaceutically acceptable carriers, optionally comprising at least one chemotherapeutic agent, further optionally comprising at least one biologic response, agent selected from the group consisting of monoclonal antibodies, interferons, interleukins, colony stimulating factors and TNF-α receptor for blocker drugs.

* * * * *